(12) United States Patent
Kim et al.

(10) Patent No.: US 11,952,435 B2
(45) Date of Patent: Apr. 9, 2024

(54) HIGHLY CRYSTALLINE ALPHA-1,3-GLUCAN

(71) Applicant: NUTRITION & BIOSCIENCES USA 4, INC., Rochester, NY (US)

(72) Inventors: Kyle Hyun Chang Kim, Wilmington, DE (US); Yefim Brun, Wilmington, DE (US); Lucia Daniela Ionescu, Oegstgeest (NL); Juan David Londono, Bear, DE (US); Jorge Mok, Wilmington, DE (US); James Joshua Ohane, West Chester, PA (US); Lemuel Tong, Kingston (CA)

(73) Assignee: NUTRITION & BIOSCIENCES USA 4, INC., Rochester, NY (US)

( * ) Notice: Subject to any disclaimer, the term of this patent is extended or adjusted under 35 U.S.C. 154(b) by 0 days.

(21) Appl. No.: 18/184,845

(22) Filed: Mar. 16, 2023

(65) Prior Publication Data
US 2023/0383014 A1   Nov. 30, 2023

Related U.S. Application Data

(63) Continuation of application No. 17/089,817, filed on Nov. 5, 2020, now Pat. No. 11,608,388.
(Continued)

(51) Int. Cl.
| | |
|---|---|
| *C08B 37/00* | (2006.01) |
| *A23B 7/154* | (2006.01) |
| *A23B 7/16* | (2006.01) |
| *A23L 3/349* | (2006.01) |
| *A61K 8/73* | (2006.01) |

(Continued)

(52) U.S. Cl.
CPC ......... *C08B 37/0009* (2013.01); *A23B 7/154* (2013.01); *A23B 7/16* (2013.01); *A23L 3/349* (2013.01); *A61K 8/73* (2013.01); *A61K 47/36* (2013.01); *A61Q 17/04* (2013.01); *C08L 7/00* (2013.01); *C08L 75/04* (2013.01); *C09D 7/65* (2018.01); *C09D 175/04* (2013.01); *D21H 17/24* (2013.01); *D21H 19/12* (2013.01); *A23V 2002/00* (2013.01); *A61K 2800/10* (2013.01)

(58) Field of Classification Search
None
See application file for complete search history.

(56) References Cited

U.S. PATENT DOCUMENTS 5,687,090 A * 11/1997 Chen ................... B01J 19/0006
703/12

FOREIGN PATENT DOCUMENTS

WO   WO-2018081263 A1 * 5/2018 ............... B60C 1/00

OTHER PUBLICATIONS

Ogawa, K. et al., Crystal Structure of (1→3)-α-D-Glucan, Fiber Diffraction Methods, 1149 (1980) pp. 353-362. (Year: 1980).*
(Continued)

*Primary Examiner* — Dominic Lazaro

(57) ABSTRACT

Disclosed herein are compositions comprising insoluble alpha-glucan particles having a high degree of crystallinity and small particle size. For example, the alpha-glucan particles can have a degree of crystallinity of at least about 0.65, and/or an average size of less than a micron. At least 50% of the glycosidic linkages of the insoluble alpha-glucan in the disclosed particles are alpha-1,3 glycosidic linkages. Further disclosed are methods of producing insoluble alpha-glucan particles, as well as their use in various applications and products.

14 Claims, 9 Drawing Sheets

Related U.S. Application Data

(60) Provisional application No. 63/084,036, filed on Sep. 28, 2020, provisional application No. 63/035,978, filed on Jun. 8, 2020, provisional application No. 62/931,242, filed on Nov. 6, 2019, provisional application No. 62/931,239, filed on Nov. 6, 2019.

(51) Int. Cl.
| | |
|---|---|
| *A61K 47/36* | (2006.01) |
| *A61Q 17/04* | (2006.01) |
| *C08L 7/00* | (2006.01) |
| *C08L 75/04* | (2006.01) |
| *C09D 7/65* | (2018.01) |
| *C09D 175/04* | (2006.01) |
| *D21H 17/24* | (2006.01) |
| *D21H 19/12* | (2006.01) |

(56) References Cited

OTHER PUBLICATIONS

Degree of Polymerization, Wikipedia, accessed, Jan. 27, 2023 at https://en.wikipedia.org/wiki/Degree_of_polymerization. (Year: 2023).*

* cited by examiner

Electron Micrographs of Insoluble Alpha-1,3-Glucan
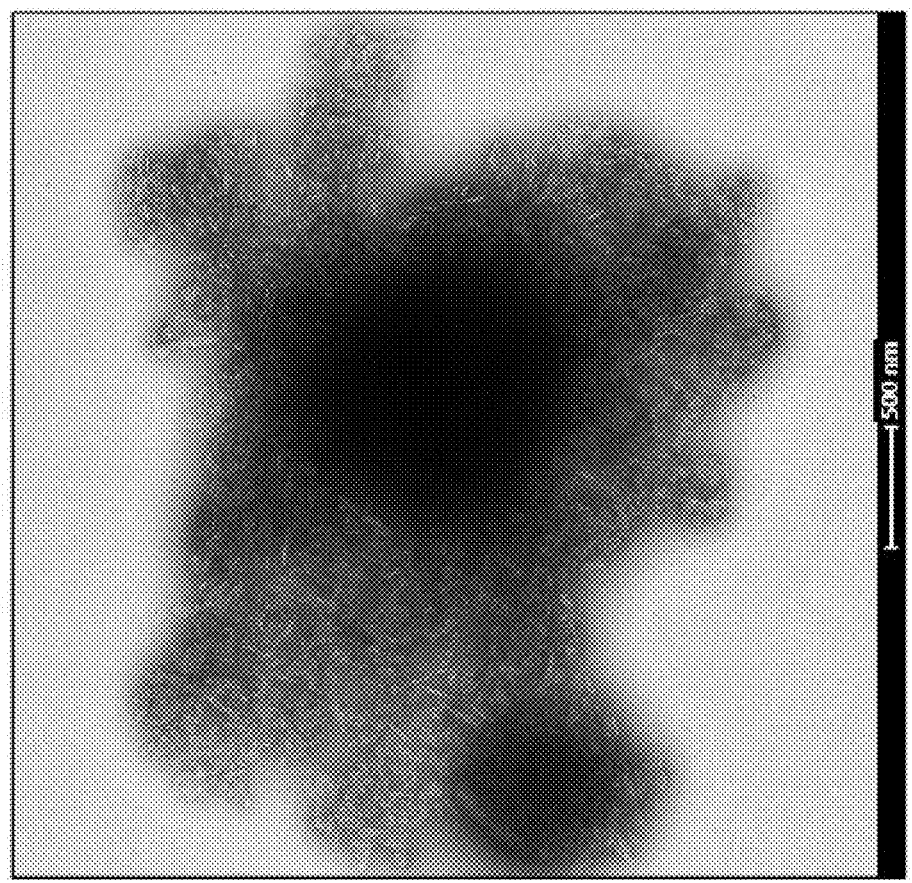
FIG. 3B Hydrolyzed (DPw 50)
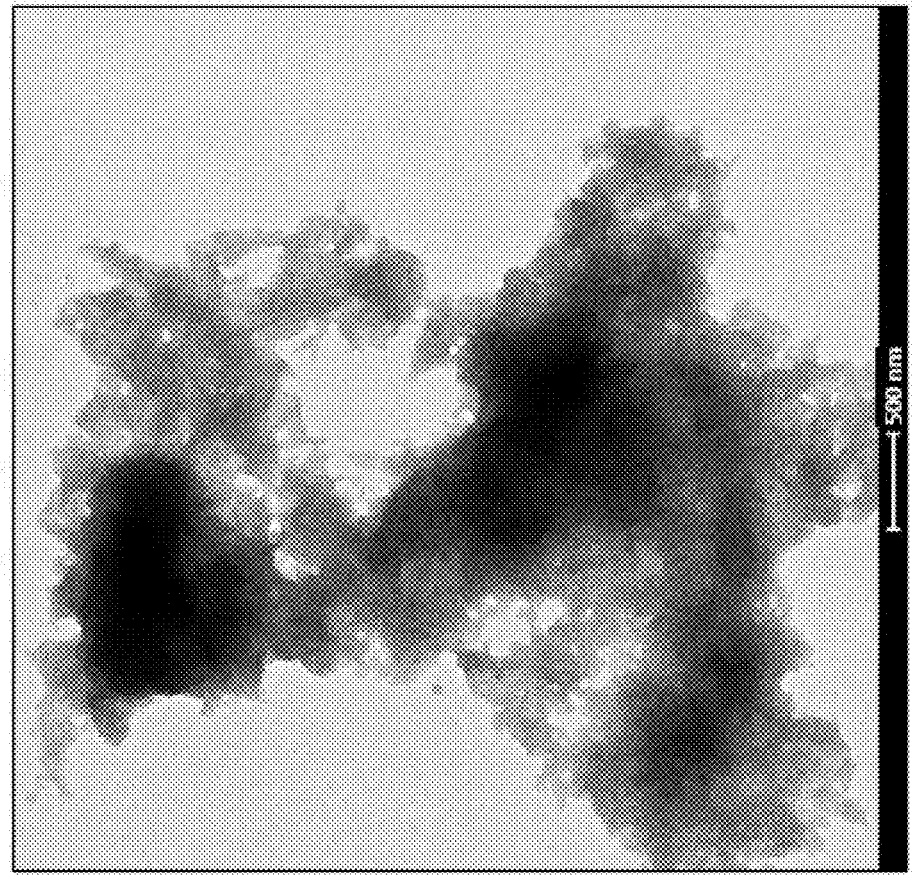
FIG. 3A Non-Hydrolyzed (DPw ~800)

Electron Micrographs of Insoluble Alpha-1,3-Glucan

Hydrolyzed (DPw 50)

Non-Hydrolyzed (DPw ~800)

HIGHLY CRYSTALLINE ALPHA-1,3-GLUCAN

This application is a divisional of application Ser. No. 17/089,817 (filed Nov. 5, 2020) (now U.S. patent Ser. No. 11/608,388), which claims the benefit of U.S. Provisional Application Nos. 62/931,242 (filed Nov. 6, 2019), 62/931,239 (filed Nov. 6, 2019), 63/035,978 (filed Jun. 8, 2020), and 63/084,036 (filed Sep. 28, 2020), the disclosures of which prior applications are all incorporated herein by reference in their entirety.

FIELD

The present disclosure is in the field of polysaccharides. For example, the disclosure pertains to crystalline alpha-1,3-glucan, methods of its production, and use of this material in various applications.

BACKGROUND

Driven by a desire to use polysaccharides in various applications, researchers have explored for polysaccharides that are biodegradable and that can be made economically from renewably sourced feedstocks. One such polysaccharide is alpha-1,3-glucan, an insoluble glucan polymer characterized by having alpha-1,3-glycosidic linkages. This polymer has been prepared, for example, using a glucosyltransferase enzyme isolated from *Streptococcus salivarius* (Simpson et al., Microbiology 141:1451-1460, 1995). Also for example, U.S. Pat. No. 7,000,000 disclosed the preparation of a spun fiber from enzymatically produced alpha-1,3-glucan. Various other glucan materials have also been studied for developing new or enhanced applications. For example, U.S. Patent Appl. Publ. No. 2015/0232819 discloses enzymatic synthesis of several insoluble glucans having mixed alpha-1,3 and -1,6 linkages.

New forms of insoluble alpha-glucan are desired to enhance the economic value and performance characteristics of this material in various applications. Addressing this need, described herein is insoluble alpha-1,3-glucan having high crystallinity and controlled particle size.

SUMMARY

In one embodiment, the present disclosure concerns a composition comprising insoluble alpha-glucan particles having a degree of crystallinity of at least about 0.65, wherein the insoluble alpha-glucan has a weight-average degree of polymerization (DPw) of at least 15, and at least 50% of the glycosidic linkages of the insoluble alpha-glucan are alpha-1,3 glycosidic linkages.

In another embodiment, the present disclosure concerns a composition comprising insoluble alpha-glucan particles, wherein at least 80 wt % of the particles are in the form of plates and at least 50% of the glycosidic linkages of the insoluble alpha-glucan are alpha-1,3 glycosidic linkages, and: (i) at least 70% by weight of the insoluble alpha-glucan particles have a diameter of less than 1.0 micron, and/or (ii) 45-55% by weight of the insoluble alpha-glucan particles have a diameter of less than 0.35 micron.

In another embodiment, the present disclosure concerns a method of producing insoluble alpha-glucan particles herein. Such a method comprises: (a) providing insoluble alpha-glucan as produced in an enzymatic reaction comprising at least water, sucrose and a glucosyltransferase enzyme that synthesizes the insoluble alpha-glucan, wherein the insoluble alpha-glucan has a weight-average degree of polymerization (DPw) of at least about 200 and at least 50% of the glycosidic linkages of the insoluble alpha-glucan are alpha-1,3 glycosidic linkages, (b) hydrolyzing the insoluble alpha-glucan to insoluble alpha-glucan particles with a DPw of about 35 to about 100, wherein the hydrolyzing is performed under aqueous conditions at a pH of 2.0 or less, and (c) optionally isolating the insoluble alpha-glucan particles produced in step (b).

BRIEF DESCRIPTION OF THE DRAWINGS

FIGS. 3A-D: Shown are electron micrographs of hydrolyzed (DPw 50) (FIGS. 3B and 3D) and non-hydrolyzed (DPw~800) (FIGS. 3A and 3C) alpha-1,3-glucan. Reference bars (500, 200, or 100 nm) are provided under each micrograph. Refer to Example 1.

DETAILED DESCRIPTION

Figure 1:
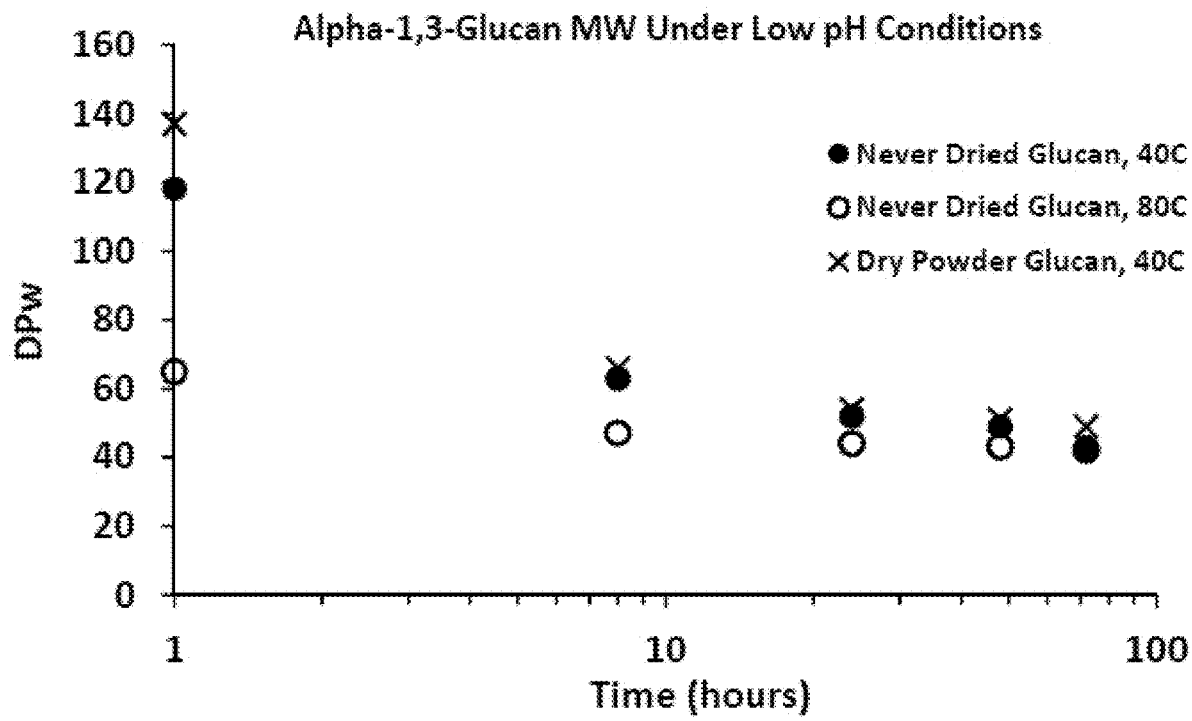
FIG. 1: Shown is the molecular weight (DPw) of alpha-1,3-glucan over time during treatment under low pH hydrolysis conditions. The legend shows that either never-dried or dried alpha-1,3-glucan were entered into hydrolysis reactions at 40 or 80° C. Refer to Example 1.

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" (i.e., 1-5) is recited, the recited range should be construed as including ranges "1 to 4", "1 to 3", "1-2", "1-2 & 4-5", "1-3 & 5", and the like.

The terms "alpha-glucan", "alpha-glucan polymer" and the like are used interchangeably herein. An alpha-glucan is a polymer comprising glucose monomeric units linked together by alpha-glycosidic linkages. In typical embodiments, an alpha-glucan herein comprises 100% alpha-glycosidic linkages, or at least about 80%, 81%, 82%, 83%, 84%, 85%, 86%, 87%, 88%, 89%, 90%, 91%, 92%, 93%, 94%, 95%, 96%, 97%, 98%, or 99% alpha-glycosidic linkages. Examples of alpha-glucan polymers herein include alpha-1,3-glucan.

The terms "poly alpha-1,3-glucan", "alpha-1,3-glucan", "alpha-1,3-glucan polymer" and the like are used interchangeably herein. Alpha-1,3-glucan is a polymer comprising glucose monomeric units linked together by glycosidic linkages, wherein at least about 50% of the glycosidic linkages are alpha-1,3. Alpha-1,3-glucan in certain embodiments comprises at least 90% or 95% alpha-1,3 glycosidic linkages. Most or all of the other linkages in alpha-1,3-glucan herein typically are alpha-1,6, though some linkages may also be alpha-1,2 and/or alpha-1,4.

The term "copolymer" herein refers to a polymer comprising at least two different types of alpha-glucan, such as dextran and alpha-1,3-glucan. The terms "graft copolymer", "branched copolymer" and the like herein generally refer to a copolymer comprising a "backbone" (or "main chain") and side chains branching from the backbone. The side chains are structurally distinct from the backbone. Examples of graft copolymers herein comprise a dextran backbone (or dextran backbone that has been modified with about 1%-35% alpha-1,2 branches, e.g.), and at least one side chain of alpha-1,3-glucan comprising at least about 50% alpha-1,3 glycosidic linkages. An alpha-1,3-glucan side chain herein can have a linkage and molecular weight of alpha-1,3-glucan as disclosed herein, for example. In some aspects, a dextran backbone can have an alpha-1,3-glucan extension, since the non-reducing end(s) of dextran can prime alpha-1,3-glucan synthesis by a glucosyltransferase enzyme.

The terms "dextran", "dextran polymer", "dextran molecule" and the like in some aspects herein refer to a water-soluble alpha-glucan comprising at least 50%, 60%, 70%, 80%, 90%, 95%, 96%, 97%, 98%, 99%, or 99.5% alpha-1,6 glycosidic linkages (with the balance of the linkages typically being all or mostly alpha-1,3). Enzymes capable of synthesizing dextran from sucrose may be described as "dextransucrases" (EC 2.4.1.5). As used herein, the term "dextranase" (alpha-1,6-glucan-6-glucanohydrolase; EC 3.2.1.11) refers to an enzyme capable of endohydrolysing 1,6-alpha glycosidic linkages.

The terms "glycosidic linkage", "glycosidic bond", "linkage" and the like are used interchangeably herein and refer to the covalent bonds connecting the sugar monomers within a saccharide compound (oligosaccharides and/or polysaccharides). The term "alpha-1,3-glycosidic linkage" as used herein refers to the type of covalent bond that joins alpha-D-glucose molecules to each other through carbons 1 and 3 on adjacent alpha-D-glucose rings. The term "alpha-1,6-glycosidic linkage" as used herein refers to the covalent bond that joins alpha-D-glucose molecules to each other through carbons 1 and 6 on adjacent alpha-D-glucose rings. The glycosidic linkages of a glucan polymer herein can also be referred to as "glucosidic linkages". Herein, "alpha-D-glucose" will be referred to as "glucose".

The glycosidic linkage profile of an alpha-glucan herein can be determined using any method known in the art. For example, a linkage profile can be determined using methods using nuclear magnetic resonance (NMR) spectroscopy (e.g., $^{13}$C NMR and/or $^1$H NMR). These and other methods that can be used are disclosed in, for example, *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, FL, 2005), which is incorporated herein by reference.

The "molecular weight" of alpha-glucan polymers herein can be represented as weight-average molecular weight (Mw) or number-average molecular weight (Mn), the units of which are in Daltons (Da) or grams/mole. Alternatively, the molecular weight of alpha-glucan polymers can be represented as DPw (weight average degree of polymerization) or DPn (number average degree of polymerization). The molecular weight of smaller alpha-glucan polymers such as oligosaccharides can optionally be provided as "DP" (degree of polymerization), which simply refers to the number of glucoses comprised within the alpha-glucan; "DP" can also characterize the molecular weight of a polymer on an individual molecule basis. Various means are known in the art for calculating these various molecular weight measurements such as with high-pressure liquid chromatography (HPLC), size exclusion chromatography (SEC), or gel permeation chromatography (GPC).

As used herein, Mw can be calculated as Mw=$\Sigma$NiMi$^2$/$\Sigma$NiMi; where Mi is the molecular weight of an individual chain i and Ni is the number of chains of that molecular weight. Besides SEC, the Mw of a polymer can be determined by other techniques such as static light scattering, mass spectrometry, MALDI-TOF (matrix-assisted laser desorption/ionization time-of-flight), small angle X-ray or neutron scattering, or ultracentrifugation. As used herein, Mn can be calculated as Mn=$\Sigma$NiMi/$\Sigma$Ni where Mi is the molecular weight of a chain i and Ni is the number of chains of that molecular weight. Besides SEC, the Mn of a polymer can be determined by various colligative property methods such as vapor pressure osmometry, end-group determination by spectroscopic methods such as proton NMR, proton FTIR, or UV-Vis. As used herein, DPn and DPw can be calculated from Mw and Mn, respectively, by dividing them by molar mass of the one monomer unit $M_1$. In the case of unsubstituted glucan polymer, $M_1$=162. In the case of a substituted (derivatized) glucan polymer, $M_1$=162+$M_f$×DoS, where $M_f$ is molar mass of the substituting group, and DoS is degree of substitution (average number of substituted groups per one glucose unit of the glucan polymer).

The terms "crystalline", "crystalline solid", "crystal" and like terms herein refer to a solid material whose constituents are arranged in a regularly ordered structure forming a lattice; such material typically is a portion of a larger composition having both crystalline and amorphous regions. An "amorphous" material is non-crystalline in that its constituents are not organized in a definite lattice pattern, but rather are randomly organized. Crystalline materials, but not amorphous materials, usually have a characteristic geometric shape (e.g., plate). The terms "crystallinity", "crystallinity index" (CI), "degree of crystallinity" and the like herein refer to the fractional amount (mass fraction or volume fraction) of an insoluble alpha-glucan that is crystalline, and can be referred to in decimal or percentage form (e.g., a crystallinity of 0.65 corresponds to a crystallinity of 65%). This fractional amount is of a total amount or volume that includes the amorphous content of the insoluble alpha-glucan. Crystallinity herein can be as measured using techniques such as differential scanning calorimetry (DSC), X-ray diffraction (XRD), small angle X-ray scattering (SAXS), infrared spectroscopy, and/or density measurements according to, for example, Struszczyk et al. (1987, *J. Appl. Polym. Sci.* 33:177-189), U.S. Patent Appl. Publ. Nos. 2015/0247176, 2010/0233773, or 2015/0152196, and/or International Patent Appl. Publ. No. WO2018/081263, which are all incorporated herein by reference. In some aspects, the crystallinity of insoluble alpha-1,3-glucan herein can be as determined according to the methodology disclosed in the below Examples.

The terms "particle", "particulate" and like terms are interchangeably used herein, and refers to the smallest identifiable unit in a particulate system. A particle of insoluble alpha-glucan in some aspects has an average size of about 0.05-1.0 micron (micrometer). The term "particulated" and like terms can be used to characterize particles of insoluble alpha-glucan herein; particulated insoluble alpha-glucan in typical aspects of the present disclosure is as this material exists when dispersed under aqueous conditions. Particle size in some aspects can refer to particle diameter and/or the length of the longest particle dimension. The average size can be based on the average of diameters and/or longest particle dimensions of at least 50, 100, 500, 1000, 2500, 5000, or 10000 or more particles, for example. Particles herein can be in plate form, for instance.

Figure 3D:
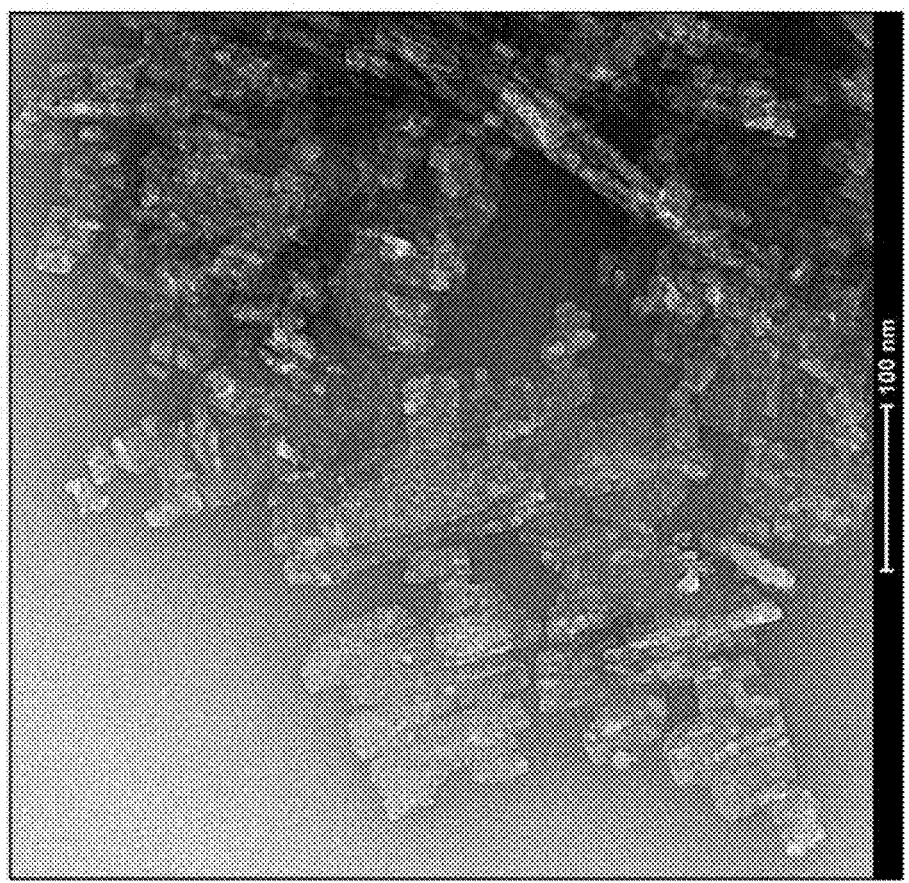

The terms "plate", "platy", "plate-like", "flakey" and like terms herein characterize the shape of insoluble alpha-glucan particles in some aspects. Particles having this shape herein generally are flat (more two-dimensional than three-dimensional), as opposed to being spherical, cylindrical, fibrillar, fibrous, rod-like, cubic, acicular, spongey/porous, lamellar, or of some other shape. Examples of plate shape with respect to particles herein are shown in FIGS. 3B and 3D. Particles herein can optionally be referred to as "plates", "platelets", and like terms, and/or collectively as "microcrystalline glucan" and like terms.

The term "sucrose" herein refers to a non-reducing disaccharide composed of an alpha-D-glucose molecule and a beta-D-fructose molecule linked by an alpha-1,2-glycosidic bond. Sucrose is known commonly as table sugar. Sucrose can alternatively be referred to as "alpha-D-glucopyranosyl-(1→2)-beta-D-fructofuranoside". "Alpha-D-glucopyranosyl" and "glucosyl" are used interchangeably herein.

The terms "glucosyltransferase", "glucosyltransferase enzyme", "GTF", "glucansucrase" and the like are used interchangeably herein. The activity of a glucosyltransferase herein catalyzes the reaction of the substrate sucrose to make the products alpha-glucan and fructose. Other products (by-products) of a GTF reaction can include glucose, various soluble gluco-oligosaccharides, and leucrose. Wild type forms of glucosyltransferase enzymes generally contain (in the N-terminal to C-terminal direction) a signal peptide (which is typically removed by cleavage processes), a variable domain, a catalytic domain, and a glucan-binding domain. A glucosyltransferase herein is classified under the glycoside hydrolase family 70 (GH70) according to the CAZy (Carbohydrate-Active EnZymes) database (Cantarel et al., *Nucleic Acids Res.* 37:D233-238, 2009).

The term "glucosyltransferase catalytic domain" herein refers to the domain of a glucosyltransferase enzyme that provides alpha-glucan-synthesizing activity to a glucosyltransferase enzyme. A glucosyltransferase catalytic domain typically does not require the presence of any other domains to have this activity.

The terms "enzymatic reaction", "glucosyltransferase reaction", "glucan synthesis reaction", "reaction composition", "reaction formulation" and the like are used interchangeably herein and generally refer to a reaction that initially comprises water, sucrose, at least one active glucosyltransferase enzyme, and optionally other components. Components that can be further present in a glucosyltransferase reaction typically after it has commenced include fructose, glucose, leucrose, soluble gluco-oligosaccharides (e.g., DP2-DP7) (such may be considered as products or by-products, depending on the glucosyltransferase used), and/or insoluble alpha-glucan product(s) of DP8 or higher (e.g., DP100 and higher). It would be understood that certain glucan products, such as alpha-1,3-glucan with a degree of polymerization (DP) of at least 8 or 9, are water-insoluble and thus not dissolved in a glucan synthesis reaction, but rather may be present out of solution (e.g., by virtue of having precipitated from the reaction). It is in a glucan synthesis reaction where the step of contacting water, sucrose and a glucosyltransferase enzyme is performed. The term "under suitable reaction conditions" as used herein refers to reaction conditions that support conversion of sucrose to alpha-glucan product(s) and fructose via glucosyltransferase enzyme activity. It is during such a reaction that glucosyl groups originally derived from the input sucrose are enzymatically transferred and used in alpha-glucan polymer synthesis; glucosyl groups as involved in this process can thus optionally be referred to as the glucosyl component or moiety (or like terms) of a glucosyltransferase reaction. Insoluble alpha-glucan produced by a glycosyltranferase reaction herein can in turn be used to prepare insoluble alpha-glucan of the present disclosure, such as through a hydrolysis procedure.

The "yield" of insoluble alpha-glucan product in a glucosyltransferase reaction in some aspects herein represents the molar yield based on the converted sucrose. The molar yield of an alpha-glucan product can be calculated based on the moles of insoluble alpha-glucan product divided by the moles of the sucrose converted. Moles of converted sucrose can be calculated as follows: (mass of initial sucrose−mass of final sucrose)/molecular weight of sucrose [342 g/mol]. This molar yield calculation can be considered as a measure of selectivity of the reaction toward the insoluble alpha-glucan. In some aspects, the "yield" of insoluble alpha-glucan product in a glucosyltransferase reaction can be based on the glucosyl component of the reaction. Such a yield (yield based on glucosyl) can be measured using the following formula:

$$\text{Insoluble Alpha-Glucan Yield} = ((IS/2 - (FS/2 + LE/2 + GL + SO))/(IS/2 - FS/2)) \times 100\%.$$

The fructose balance of a glucosyltransferase reaction can be measured to ensure that HPLC data, if applicable, are not out of range (90-110% is considered acceptable). Fructose balance can be measured using the following formula:

$$\text{Fructose Balance} = ((180/342 \times (FS + LE) + FR)/(180/342 \times IS)) \times 100\%.$$

In the above two formulae, IS is [Initial Sucrose], FS is [Final Sucrose], LE is [Leucrose], GL is [Glucose], SO is [Soluble Oligomers] (gluco-oligosaccharides), and FR is [Fructose]; the concentrations of each foregoing substrate/product provided in double brackets are in units of grams/L and as measured by HPLC, for example.

A "cake" of insoluble alpha-glucan herein refers to a preparation in condensed, compacted, packed, squeezed, and/or compressed form that comprises at least (i) about 50%-90% by weight water or an aqueous solution, and (ii) about 10%-50% by weight insoluble alpha-glucan. A cake in some aspects can be referred to as a "filter cake" or a "wet cake". A cake herein typically has a soft, solid-like consistency.

A composition herein comprising insoluble alpha-glucan that is "dry" or "dried" typically has less than 6, 5, 4, 3, 2, 1, 0.5, or 0.1 wt % water comprised therein.

The term "hydrolysis" and like terms herein refer to the decomposition of insoluble alpha-glucan to smaller (lower molecular weight), but still insoluble, alpha-glucan, where water is consumed in cleaving glycosidic linkages of the insoluble alpha-glucan. A "hydrolysis reaction", "hydrolysis reaction composition", or like term herein typically refers to a reaction that initially comprises at least an aqueous liquid, insoluble alpha-glucan, and a hydrolyzing agent (e.g., chemical, catalyst/enzyme). An acid hydrolysis reaction as referred to herein comprises acid as a hydrolyzing agent, the pH of an acid hydrolysis reaction herein can be 4.0 or below, for example.

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The terms "weight/volume percent", "w/v %" and the like are used interchangeably herein. Weight/volume percent can be calculated as: ((mass [g] of material)/(total volume [mL] of the material plus the liquid in which the material is placed))×100%. The material can be insoluble in the liquid (i.e., be a solid phase in a liquid phase, such as with a dispersion), or soluble in the liquid (i.e., be a solute dissolved in the liquid).

The term "pigment volume concentration" (PVC) herein refers to the ratio of the volume of a pigment to the volume of total nonvolatile material present in a coating, and is typically expressed as a percentage. The formula for calculating PVC is: ((pigment volume)/(pigment volume+binder volume+other solids volume))×100. A "pigment" herein can refer to, for example, any organic and/or inorganic entity whose solubility in water is less than 0.01 wt % at 20° C. (e.g., less than 0.0001 wt %), and which exhibits light absorption at a wavelength ranging from 350 nm to 700 nm, such as absorption with one maximum.

The terms "aqueous liquid", "aqueous fluid", "aqueous conditions", "aqueous reaction conditions", "aqueous setting", "aqueous system" and the like as used herein can refer to water or an aqueous solution. An "aqueous solution" herein can comprise one or more dissolved salts, where the maximal total salt concentration can be about 3.5 wt % in some embodiments. Although aqueous liquids herein typically comprise water as the only solvent in the liquid, an aqueous liquid can optionally comprise one or more other solvents (e.g., polar organic solvent) that are miscible in water. Thus, an aqueous solution can comprise a solvent having at least about 10 wt % water.

An "aqueous composition" herein has a liquid component that comprises about, or at least about, 10, 20, 30, 40, 50, 60, 70, 80, 90, 95, 99, or 100 wt % water, for example. Examples of aqueous compositions include mixtures, solutions, dispersions (e.g., colloidal dispersions), suspensions and emulsions, for example.

As used herein, the term "colloidal dispersion" refers to a heterogeneous system having a dispersed phase and a dispersion medium, i.e., microscopically dispersed insoluble particles are suspended throughout another substance (e.g., an aqueous composition such as water or aqueous solution).

An example of a colloidal dispersion herein is a hydrocolloid. All, or a portion of, the particles of a colloidal dispersion such as a hydrocolloid can comprise insoluble alpha-1,3-glucan as presently disclosed. The terms "dispersant" and "dispersion agent" are used interchangeably herein to refer to a material that promotes the formation and/or stabilization of a dispersion. "Dispersing" herein refers to the act of preparing a dispersion of a material in an aqueous liquid. As used herein, the term "latex" (and like terms) refers to a dispersion of one or more types of polymer particles in water or aqueous solution; typically, at least insoluble alpha-glucan particles are in a latex composition as a dispersed polymer component. In some aspects, a latex is an emulsion that comprises a dispersion of at least insoluble alpha-glucan particles. An "emulsion" herein is a dispersion of minute droplets of one liquid in another liquid in which the droplets are not soluble or miscible (e.g., a non-polar substance such as oil or other organic liquid such as an alkane, in a polar liquid such as water or aqueous solution). An emulsion can further comprise dispersed alpha-glucan particles herein, for example, which optionally can stabilize the emulsion. In some aspects, however, an emulsion herein can be a "dry emulsion". A dry emulsion is typically produced by removing all or most (e.g. >95%, >99%, or >99.5%) of the water of a liquid emulsion, such as by freeze-drying or spray-drying. Insoluble alpha-glucan particles of the present disclosure can provide stability to a dispersion or emulsion, for example. The "stability" (or the quality of being "stable") of a dispersion or emulsion herein is, for example, the ability of dispersed particles of a dispersion, or liquid droplets dispersed in another liquid (emulsion), to remain dispersed (e.g., about, or at least about, 70, 75, 80, 85, 90, 95, 96, 97, 98, 99, or 100 wt % of the particles of the dispersion or liquid droplets of the emulsion are in a dispersed state) for a period of about, or at least about, 2, 4, 6, 9, 12, 18, 24, 30, or 36 months following initial preparation of the dispersion or emulsion. A stable dispersion or emulsion can resist total creaming, sedimentation, flocculation, and/or coalescence of dispersed/emulsified material.

An alpha-glucan that is "insoluble", "aqueous-insoluble", "water-insoluble" (and like terms) (e.g., alpha-1,3-glucan with a DP of 8 or higher) herein does not dissolve (or does not appreciably dissolve) in water or other aqueous conditions, optionally where the aqueous conditions are further characterized to have a pH of 0-9 (e.g., pH 6-8) and/or temperature of about 1 to 130° C. (e.g., 20-25° C.). In some aspects, less than 1.0 gram (e.g., no detectable amount) of an aqueous-insoluble graft copolymer or derivative thereof dissolves in 1000 milliliters of such aqueous conditions (e.g., water at 23° C.). In contrast, glucans such as certain oligosaccharides herein that are "soluble", "aqueous-soluble", "water-soluble" and the like (e.g., alpha-1,3-glucan with a DP less than 8) appreciably dissolve under these conditions.

The term "viscosity" as used herein refers to the measure of the extent to which a fluid (aqueous or non-aqueous) resists a force tending to cause it to flow. Various units of viscosity that can be used herein include centipoise (cP, cps) and Pascal-second (Pa-s), for example. A centipoise is one one-hundredth of a poise; one poise is equal to 0.100 $kg \cdot m^{-1} \cdot s^{-1}$.

The terms "crosslink", "crosslinked" and the like herein refer to one or more bonds (typically covalent) that connect polymers such as insoluble alpha-glucan particles as presently disclosed. A crosslink having multiple bonds typically comprises one or more atoms that are part of a crosslinking agent that was used to form the crosslink. The terms "crosslinking agent", "crosslinker" and the like herein refer to an atom or compound that can create crosslinks. The term "crosslinking reaction" and like terms (e.g., "crosslinking composition", "crosslinking preparation") herein typically refer to a reaction comprising at least a solvent, a crosslinking agent, insoluble alpha-glucan particles and optionally another polymer, a reaction can be in the context of preparing a film or coating, for example. A crosslinking reaction in some aspects comprises an aqueous solvent such as water, whereas in other aspects the solvent is non-aqueous.

The terms "household care product", "home care" and the like typically refer to products, goods and services relating to the treatment, cleaning, caring and/or conditioning of a home and its contents. The foregoing include, for example, chemicals, compositions, products, or combinations thereof having application in such care.

The terms "fiber", "fibers" and the like herein refer to staple fibers (staple length fibers) and continuous fibers, in some aspects. Fibers herein can comprise alpha-1,3-glucan, natural fiber (e.g., cellulose, cotton, wool, silk), or synthetic fiber (e.g., polyester), or any other type of material disclosed herein that can form a fiber.

The terms "fabric", "textile", "cloth" and the like are used interchangeably herein to refer to a woven material having a network of natural and/or artificial fibers. Such fibers can be in the form of thread or yarn, for example.

The terms "non-woven", "non-woven product", "non-woven web" and the like herein refer to a web of individual fibers or filaments that are interlaid, typically in a random or unidentifiable manner. This contrasts with a knitted or woven fabric, which has an identifiable network of fibers or filaments. In some aspects, a non-woven product comprises a non-woven web that is bound or attached to another material such as a substrate or backing. A non-woven in some aspects can further contain a binder or adhesive (strengthening agent) that binds adjacent non-woven fibers together. A non-woven binder or adhesive agent can be applied to the non-woven in the form of a dispersion/latex, solution, or solid, for example, and then the treated non-woven is typically dried.

A "fabric care composition", "laundry care composition", and like terms refer to any composition suitable for treating fabric, non-wovens, and/or any similar material in some manner. Examples of such a composition include laundry detergents and fabric softeners.

A "detergent composition" herein typically comprises at least a surfactant (detergent compound) and/or a builder. A "surfactant" herein refers to a substance that tends to reduce the surface tension of a liquid in which the substance is dissolved. A surfactant may act as a detergent, wetting agent, emulsifier, foaming agent, and/or dispersant, for example.

The term "personal care product" and like terms typically refer to products, goods and services relating to the treatment, cleaning, cleansing, caring or conditioning of a person. The foregoing include, for example, chemicals, compositions, products, or combinations thereof having application in such care.

The terms "ingestible product", "ingestible composition" and the like refer to any substance that, either alone or together with another substance, may be taken orally (i.e., by mouth), whether intended for consumption or not. Thus, an ingestible product includes food/beverage products. "Food/beverage products" refer to any edible product intended for consumption (e.g., for nutritional purposes) by humans or animals, including solids, semi-solids, or liquids. A "food" herein can optionally be referred to as a "foodstuff", "food product", or other like term, for example. "Non-edible products" ("non-edible compositions") refer to any composition that can be taken by the mouth for purposes other than food or beverage consumption. Examples of non-edible products herein include supplements, nutraceuticals, functional food products, pharmaceutical products, oral care products (e.g., dentifrices, mouthwashes), and cosmetic products such as sweetened lip balms. A "pharmaceutical product", "medicine", "medication", "drug" or like term herein refers to a composition used to treat disease or injury, and can be administered enterally or parenterally.

The terms "film", "sheet" and like terms herein refer to a generally thin, visually continuous material. A film can be comprised as a layer or coating on a material, or can be alone (e.g., not attached to a material surface, free-standing). A "coating" (and like terms) as used herein refers to a layer covering a surface of a material. The term "uniform thickness" as used to characterize a film or coating herein can refer to a contiguous area that (i) is at least 20% of the total film/coating area, and (ii) has a standard deviation of thickness of less than about 50 nm, for example. The term "continuous layer" means a layer of a composition applied to at least a portion of a substrate, wherein a dried layer of the composition covers ≥99% of the surface to which it has been applied and having less than 1% voids in the layer that expose the substrate surface. The ≥99% of the surface to which the layer has been applied excludes any area of the substrate to which the layer has not been applied. A coating herein can make a continuous layer in some aspects. A coating composition (and like terms) herein refers to all the solid components that form a layer on a substrate, such as insoluble alpha-glucan particles herein and, optionally, pigment, surfactant, dispersing agent, binder, crosslinking agent, and/or other additives.

The term "paint" (and like terms) herein is a type of coating composition that is a dispersion of a pigment in a suitable liquid (e.g., aqueous liquid) that can be used to form an adherent coating when spread on a surface in a thin coat. Paint as applied to a surface can provide coloration/decoration, protection, and/or treatment (e.g., primer) to the surface. A paint herein, by virtue of further comprising dispersed insoluble alpha-1,3-glucan (i.e., a dispersed polymer), can optionally be characterized as a latex or latex paint.

A "composite" herein comprises two or more components including insoluble alpha-glucan particles of the present disclosure. Typically, the components of a composite resist separation and one or more of the components display enhanced and/or different properties as compared to its properties alone, outside the composite (i.e., a composite is not simply an admixture, which generally is easily separable to its original components). A composite herein generally is a solid material, and can be made via an extrusion or molding process, for example.

The terms "sequence identity", "identity" and the like as used herein with respect to a polypeptide amino acid sequence (e.g., that of a glucosyltransferase) are as defined and determined in U.S. Patent Appl. Publ. No. 2017/0002336, which is incorporated herein by reference.

The term "isolated" means a substance (or process) in a form or environment that does not occur in nature. A non-limiting example of an isolated substance includes any non-naturally occurring substance such as some forms of insoluble alpha-1,3-glucan herein (as well as the enzymatic reactions and other processes used to prepare it). It is believed that the embodiments disclosed herein are synthetic/man-made (could not have been made except for human intervention/involvement), and/or have properties that are not naturally occurring.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein.

New forms of insoluble alpha-glucan are desired to enhance the economic value and performance characteristics of this material in various applications. Compositions comprising insoluble alpha-1,3-glucan having high crystallinity and controlled particle size are presently disclosed to address this need.

Some embodiments of the present disclosure concern a composition comprising insoluble alpha-glucan particles having a degree of crystallinity of at least about 0.65, wherein the insoluble alpha-glucan has a weight-average degree of polymerization (DPw) of at least 15, and at least 50% of the glycosidic linkages of the insoluble alpha-glucan are alpha-1,3 glycosidic linkages. Yet some embodiments of the present disclosure concern a composition comprising insoluble alpha-glucan particles, wherein at least about 70 wt % of the particles are in the form of plates and at least 50% of the glycosidic linkages of the insoluble alpha-glucan are alpha-1,3 glycosidic linkages, and wherein: (i) at least 80% by weight of the insoluble alpha-glucan particles have a diameter of less than 1.0 micron, and/or (ii) 40-60% by weight of the insoluble alpha-glucan particles have a diameter of less than 0.35 micron. Insoluble alpha-glucan particles as presently disclosed have several advantageous features, such as, in some aspects, being stable under low pH conditions (e.g., stability of molecular weight and/or viscosity of an aqueous dispersion of the particles), having unique optical characteristics (e.g., high optical clarity, translucent), having enhanced viscosity profiles (e.g., higher viscosity compared with higher DPw insoluble alpha-glucan, retaining viscosity capacity after being dried), and/or having enhanced pigment extender function in paint.

Typically, at least about 50% of the glycosidic linkages of the insoluble alpha-glucan of the presently disclosed compositions are alpha-1,3 glycosidic linkages. Insoluble alpha-glucan in some aspects can comprise about, or at least about, 40%, 50%, 60%, 70%, 80%, 85%, 90%, 91%, 92%, 93%, 94%, 95%, 96%, 97%, 98%, 99%, 99.5%, or 100% alpha-1,3 glycosidic linkages. In some aspects, accordingly, insoluble alpha-glucan has less than about 60%, 50%, 40%, 30%, 20%, 15%, 10%, 9%, 8%, 7%, 6%, 5%, 4%, 3%, 2%, 1%, 0.5%, or 0% glycosidic linkages that are not alpha-1,3. In general, the glycosidic linkages that are not alpha-1,3 are mostly or entirely alpha-1,6. In certain embodiments, insoluble alpha-glucan has no branch points or less than about 5%, 4%, 3%, 2%, or 1% branch points as a percent of the glycosidic linkages in the glucan. In aspects in which alpha-glucan comprises 50% alpha-1,3 glycosidic linkages, such glucan does not comprise alternan (alternating alpha-1,3 and -1,6 linkages).

In some aspects, the DPw or DPn of insoluble alpha-glucan is at least about 15. The DPw or DPn of insoluble alpha-glucan in some aspects can be about, or at least about, or less than about, 15, 20, 25, 30, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 125, 150, 175, 200, 15-100, 25-100, 35-100, 15-80, 25-80, 35-80, 15-60, 25-60, 35-60, 15-55, 25-55, 25-50, 35-55, 35-50, 35-45, 35-40, 40-100, 40-80, 40-60, 40-55, 40-50, 45-60, 45-55, or 45-50, for example.

Insoluble alpha-glucan particles in some aspects of the present disclosure have a degree of crystallinity (crystallinity index) of at least about 0.65. The degree of crystallinity of particles can be about, or at least about, 0.55, 0.60, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.60-0.83, 0.65-0.83, 0.67-0.83, 0.69-0.83, 0.60-0.81, 0.65-0.81, 0.67-0.81, 0.69-0.81, 0.60-0.78, 0.65-0.78, 0.67-0.78, 0.69-0.78, 0.60-0.76, 0.65-0.76, 0.67-0.76, or 0.69-0.76, for example. In general, that portion of insoluble alpha-glucan herein that is not crystalline is amorphous. Flowing from the foregoing crystallinity values, the wt % of particles that is amorphous is about, or less than about, 45%, 40%, 35%, 30%, 25%, 20%, or 15%, for example. The degree of crystallinity of alpha-glucan particles herein can be as when measured according to any suitable method (e.g., as listed above or in the below Examples), such as follows. A sample of insoluble alpha-glucan herein is dried for at least about 2 hours (e.g., 8-12 hours) in a vacuum oven set at about 55-65° C. (e.g., 60° C.). The sample is then be packed into a stainless steel holder with a well of about 1-2 cm wide by 3-5 cm long by 3-5 mm deep, after which the holder is loaded into a suitable diffractometer (e.g., X'PERT MPD POWDER diffractometer, PANalytical B.V., The Netherlands) set in reflection mode to measure the X-ray diffraction pattern of the sample. The X-ray source is a Cu X-ray tube line source with an optical focusing mirror and a ~1/16° narrowing slit. X-rays are detected with a 1-D detector and an anti-scatter slit set at ~1/8°. Data are collected in the range of about 4 to 60 degrees of two-theta at about 0.1 degrees per step. The resulting X-ray pattern is then analyzed by subtracting a linear baseline from about 7.2 to 30.5 degrees, subtracting the XRD pattern of a known amorphous alpha-1,3-glucan sample that has been scaled to fit the data, and then fitting the remaining crystal peaks in that range with a series of Gaussian curves corresponding to known dehydrated alpha-1,3-glucan crystal reflections. The area corresponding to the crystal peaks is then divided by the total area under the baseline-subtracted curve to yield a crystallinity index.

Figure 3C:
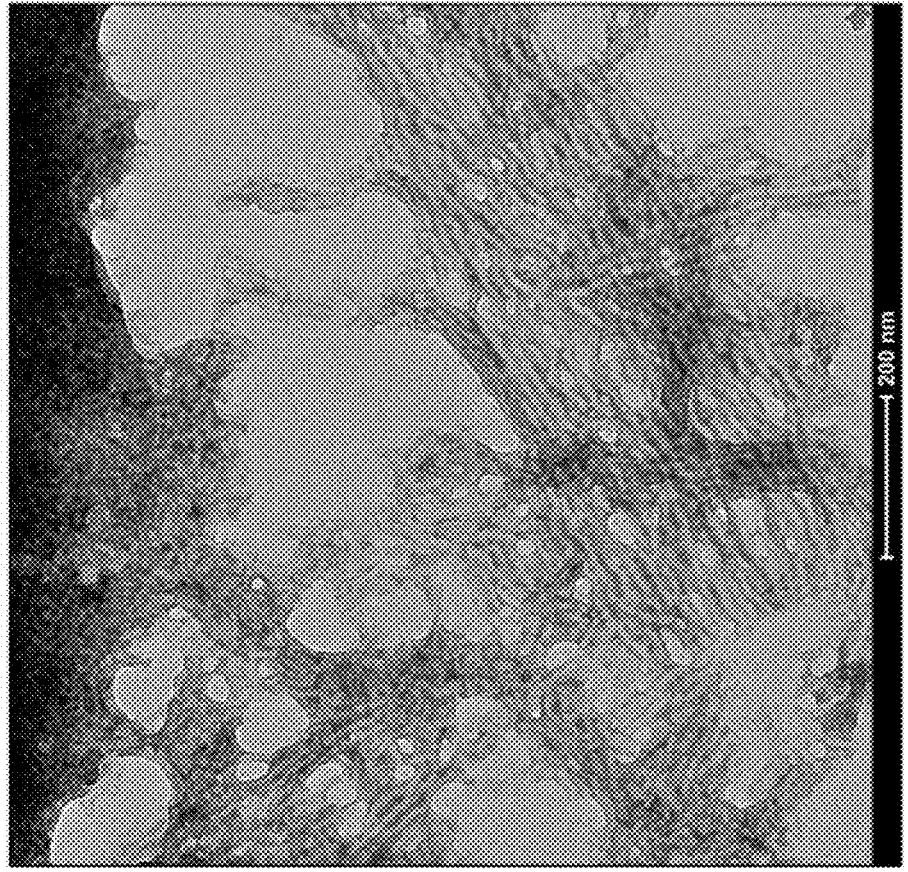

At least about 80 wt % of the particles of insoluble alpha-glucan in a composition herein are in the form of plates, for example. In some aspects, about, or at least about, 60, 65, 70, 75, 80, 81, 82, 83, 84, 85, 86, 87, 88, 89, 90, 91, 92, 93, 94, 95, 96, 97, 98, 99, 60-85, 60-80, 60-75, 60-70, 65-85, 65-80, 65-75, 65-70, 70-85, 70-80, or 70-75 wt % of the particles of insoluble alpha-glucan are in the form of plates. Plates of insoluble alpha-1,3-glucan herein can visually be the same as, or similar to, the particles shown in FIGS. 3B and 3D (e.g., when viewed by electron microscopy such as TEM or SEM). Typically, the balance of the particles of insoluble alpha-glucan in the composition are of non-plate form, such as what is shown in FIG. 3C. In some aspects, the balance of the particles that are of non-plate form can be characterized as being fibrillar and/or striated in appearance. However, in some aspects, about, or at least about, 10, 20, 30, 40, 50, 60, or 70 wt % of the particles of insoluble alpha-glucan in a composition herein are in the form of plates.

In some aspects of the present disclosure, at least about 70% by weight of the insoluble alpha-glucan particles of a composition have a diameter of less than 1.0 micron. Yet, in some aspects, about, or at least about, 65%, 70%, 75%, 80%, 85%, 90%, 95%, 65-95%, 70-95%, 75-95%, 80-95%, 85-95%, 65-90%, 70-90%, 75-90%, 80-90%, 85-90%, 65-85%, 70-85%, 75-85%, or 80-85% by weight of the insoluble alpha-glucan particles of a composition have a diameter of less than about 1.0 micron. In some aspects, about 40-60%, 40-55%, 45-60%, 45-55%, 47-53%, 48-52%, 49-51%, or 50% by weight of the insoluble alpha-glucan particles have a diameter of about, or less than about, 1.0, 0.9, 0.8, 0.7, 0.6, 0.5, 0.4, 0.35, 0.34, 0.32, 0.30, 0.28, 0.26, 0.25, 0.24, 0.23, 0.22, 0.21, 0.20, 0.19, 0.18, 0.17, 0.16, 0.15, 0.14, 0.13, 0.12, 0.11, 0.10, 0.10-1.0, 0.10-0.80, 0.10-0.60, 0.10-0.40, 0.10-0.35, 0.10-0.30, 0.10-0.25, 0.10-0.20, 0.15-0.35, 0.15-0.30, 0.15-0.25, or 0.15-0.20 micron; these foregoing micron values can optionally be considered to be a "D50" (diameter-50) value. Alpha-glucan particles in some aspects can have a thickness of about 0.010, 0.015, 0.020, 0.025, 0.030, or 0.010-0.030 micron; such a thickness can be in conjunction with any of the foregoing diameter aspects. Particle size herein can be measured by a process comprising light scattering or electrical impedance change (e.g., using a Coulter Counter), as described in any of U.S. Pat. Nos. 6,091,492, 6,741,350 and 9,297,737 (all incorporated herein by reference), and/or as disclosed in the below Examples, for example. Particle size and/or distributions can be as measured for particles comprised in an aqueous dispersion, and/or as measured using a light scatter technique, for example.

Alpha-glucan particles in some aspects have a polydispersity index (PDI) of about, or less than about, 1.13, 1.17, 1.2, 1.23, 1.27, 1.3, 1.13-1.3, 1.13-1.27, 1.13-1.23, 1.17-1.3, 1.17-1.27, 1.17-1.23, or 1.18-1.22.

Alpha-glucan herein is insoluble in aqueous systems that are not highly alkaline, such as a system with a pH≤10 or 11. In general, the solubility of a glucan polymer in aqueous settings herein is related to its linkage profile, molecular weight, and/or degree of branching. For example, alpha-1, 3-glucan with ≥95% 1,3 linkages is generally insoluble at a DP of 8 and above in aqueous conditions at 20° C. In general, as molecular weight increases, the percentage of alpha-1,3 linkages required for alpha-1,3-glucan insolubility decreases.

Insoluble alpha-glucan particles herein can be as produced by a hydrolysis method disclosed herein, for example. Typically, insoluble alpha-glucan particles herein and/or any precursors thereof do not have any chemical derivatization (e.g., etherification, esterification, phosphorylation, sulfation) (e.g., no substitution of hydrogens of glucan hydroxyl groups with a non-sugar chemical group). Insoluble alpha-glucan used for preparing particles herein typically is enzymatically derived in an inert vessel (typically under cell-free conditions), and is not derived from a cell wall (e.g., fungal cell wall).

Some embodiments of the present disclosure concern a method of producing insoluble alpha-glucan particles herein. Such a method can comprise the following steps, for example: (a) providing insoluble alpha-glucan (precursor) as produced in an enzymatic reaction comprising at least water, sucrose and a glucosyltransferase enzyme that synthesizes the insoluble alpha-glucan, wherein the insoluble alpha-glucan has a DPw or DPn of at least about 200 and at least 50% of the glycosidic linkages of the insoluble alpha-glucan are alpha-1,3 glycosidic linkages, (b) hydrolyzing the insoluble alpha-glucan (precursor) to insoluble alpha-glucan particles with a DPw or DPn, for example, of about 35 to about 100 (or, e.g., up to about 200), wherein said hydrolyzing is performed under aqueous conditions at a pH of 2.0 or less, and (c) optionally isolating the insoluble alpha-glucan particles produced in step (b). Step (b) of this method can optionally be characterized as an "acid hydrolysis" method or reaction.

Step (a) of a method of producing insoluble alpha-glucan particles herein concerns providing an insoluble alpha-glucan precursor, which is then entered into hydrolysis step (b). Insoluble "alpha-glucan precursor" herein is itself insoluble alpha-glucan, but has a molecular weight that is greater than that of the insoluble alpha-glucan produced by the acid hydrolysis method. An insoluble alpha-glucan precursor can have a glycosidic linkage profile as disclosed above (e.g., at least about 50%, 60%, 70%, 80%, 90%, 95%, 99%, or 100% alpha-1,3 glycosidic linkages) and a DPw or DPn of about, or at least about 200, 300, 400, 500, 600, 700, 800, 900, 1000, 1100, 1200, 1300, 1400, 1500, 1600, 1650, 200-1650, 300-1650, 400-1650, 500-1650, 600-1650, 700-1650, 200-1250, 300-1250, 400-1250, 500-1250, 600-1250, 700-1250, 200-1000, 300-1000, 400-1000, 500-1000, 600-1000, 700-1000, 200-900, 300-900, 400-900, 500-900, 600-900, or 700-900, for example.

An insoluble alpha-glucan precursor herein is produced by an enzymatic reaction comprising at least water, sucrose and a glucosyltransferase enzyme that synthesizes the insoluble alpha-glucan. Glucosyltransferases, reaction conditions, and/or processes contemplated to be useful for producing insoluble alpha-glucan precursor herein are disclosed in U.S. Pat. Nos. 7,000,000, 8,871,474, 10,301,604 and 10,260,053, U.S. Patent Appl. Publ. Nos. 2019/0112456, 2019/0078062, 2019/0078063, 2018/0340199, 2018/0021238, 2018/0273731, 2017/0002335 and 2015/0064748, and Int. Patent Appl. Publ. No. WO2017/079595, for example, all of which are incorporated herein by reference.

In some aspects, a glucosyltransferase enzyme for producing an insoluble alpha-glucan precursor can comprise an amino acid sequence that is 100% identical to, or at least 90%, 91%, 92%, 93%, 94%, 95%, 96%, 97%, 98%, 98.5%, 99%, or 99.5% identical to, SEQ ID NO:2, 4, 6, 8, 10, 12, 14, 16, 18, 20, 26, 28, 30, 34, or 59, or amino acid residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20, and have glucosyltransferase activity, these amino acid sequences are disclosed in U.S. Patent Appl. Publ. No. 2019/0078063, which is incorporated herein by reference. It is noted that a glucosyltransferase enzyme comprising SEQ ID NO:2, 4, 8, 10, 14, 20, 26, 28, 30, 34, or amino acid residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20, can synthesize insoluble alpha-glucan comprising at least about 90% (~100%) alpha-1,3 linkages. Any of the foregoing glucosyltransferase enzyme amino acid sequences can be modified as described below to increase product yield.

A glucosyltransferase enzyme for producing an insoluble alpha-glucan precursor can, in some aspects, synthesize insoluble alpha-glucan at a yield of at least about 40%. The yield of insoluble alpha-glucan by a glucosyltransferase enzyme in some aspects can be about, or at least about, 40%, 45%, 50%, 55%, 60%, 65%, 70%, 75%, 80%, 85%, 90%, 91%, 92%, 93%, 94%, 95%, or 96%. Yield in some aspects can be measured based on the glucosyl component of the reaction. Yield in some aspects can be measured using HPLC or NIR spectroscopy. Yield can be achieved in a reaction conducted for about 16-24 hours (e.g., ~20 hours), for example. Examples of such a glucosyltransferase enzyme are those having an amino acid sequence modified such that the enzyme produces more products (insoluble alpha-glucan precursor and fructose), and less by-products (e.g., glucose, oligosaccharides such as leucrose), from a given amount of sucrose substrate. For example, one, two, three, four, or more amino acid residues of the catalytic domain of a glucosyltransferase herein can be modified/ substituted to obtain an enzyme that produces more products. Examples of a suitable modified glucosyltransferase enzyme are disclosed in Tables 3-7 of U.S. Patent Appl. Publ. No. 2019/0078063. A modified glucosyltransferase enzyme, for example, can comprise one or more amino acid substitutions corresponding with those in Tables 3-7 (ibid.) that is/are associated with an insoluble alpha-glucan yield of at least 40% (the position numbering of such at least one substitution corresponds with the position numbering of SEQ ID NO:62 as disclosed in U.S. Patent Appl. Publ. No. 2019/0078063). A set of amino acid modifications as listed in Tables 6 or 7 (ibid.) can be used, for example.

In some aspects, an alpha-glucan precursor can be a graft copolymer such as disclosed in Int. Patent Appl. Publ. No. WO2017/079595 or U.S. Patent Appl. Publ. No. 2019/0185893, which are incorporated herein by reference. Such a graft copolymer comprises dextran (as backbone) and alpha-1,3-glucan (as side chain[s]), where the latter component has been grafted onto the former component, typically, this graft copolymer is produced by using dextran, or alpha-1,2-branched dextran, as a primer for alpha-1,3-glucan synthesis by an alpha-1,3-glucan-producing glucosyltransferase as described above. In some aspects, a graft copolymer comprises about, at least about, or less than about, 10%, 20%, 30%, 35%, 40%, 45%, 50%, 55%, 60%, 65%, 70%, 35-65%, 35-60%, 35-55%, 40-65%, 40-60%, 40-55%, 45-65%, 45-60%, 45-55%, 50-65%, 50-60%, or 50-55% by weight of a dextran backbone, where the balance of the graft copolymer is of alpha-1,3-glucan side chain(s). Alpha-1,3-glucan side chain(s) of an alpha-glucan graft copolymer herein can be alpha-1,3-glucan as presently disclosed. Dextran backbone of an alpha-glucan graft copolymer herein can comprise about 100% alpha-1,6 glycosidic linkages (i.e., completely linear dextran backbone), or about, or at least about, 90%, 95%, 96%, 97%, 98%, 99%, or 99.5% alpha-1,6 glycosidic linkages (i.e., substantially linear dextran backbone), and/or have a DP or DPw of about, at least about, or less than about, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 85, 90, 95, 100, 105, 110, 150, 200, 250, 300, 400, 500, 8-20, 8-30, 8-100, 8-500, 3-4, 3-5, 3-6, 3-7, 3-8, 4-5, 4-6, 4-7, 4-8, 5-6, 5-7, 5-8, 6-7, 6-8, 7-8, 90-120, 95-120, 100-120, 105-120, 110-120, 115-120, 90-115, 95-115, 100-115, 105-115, 110-115, 90-110, 95-110, 100-110, 105-110, 90-105, 95-105, 100-105, 90-100, 95-100, 90-95, 85-95, or 85-90, for example. In some aspects, a dextran backbone (before being integrated into a graft copolymer) has been alpha-1,2-branched; the percent alpha-1,2 branching of a backbone of a graft copolymer herein can be about, at least about, or less than about, 1%, 2%, 3%, 4%, 5%. 6%, 7%, 8%, 9%, 10%, 11%, 12%, 13%, 14%, 15%, 16%, 17%, 18%, 19%, 20%, 21%, 22%, 23%, 24%, 25%, 2-25%, 2-20%, 2-15%, 2-10%, 5-25%, 5-20%, 5-15%, 5-10%, 7-13%, 8-12%, 9-11%, 10-25%, 10-20%, or 10-15%, for example. In some aspects, dextran backbone of an alpha-glucan graft copolymer can comprise (A) (i) about 87-91.5 wt % glucose linked only at positions 1 and 6; (ii) about 0.1-1.2 wt % glucose linked only at positions 1 and 3; (iii) about 0.1-0.7 wt % glucose linked only at positions 1 and 4; (iv) about 7.7-8.6 wt % glucose linked only at positions 1, 3 and 6; and (v) about 0.4-1.7 wt % glucose linked only at: (a) positions 1, 2 and 6, or (b) positions 1, 4 and 6; or (B) (i) about 89.5-90.5 wt % glucose linked only at positions 1 and 6; (ii) about 0.4-0.9 wt % glucose linked only at positions 1 and 3; (iii) about 0.3-0.5 wt % glucose linked only at positions 1 and 4; (iv) about 8.0-8.3 wt % glucose linked only at positions 1, 3 and 6; and (v) about 0.7-1.4 wt % glucose linked only at: (a) positions 1, 2 and 6, or (b) positions 1, 4 and 6. The molecular weight of such a dextran backbone (or any other dextran backbone herein) can be about, or at least about, 0.1, 0.125, 0.15, 0.175, 0.2, 0.24, 0.25, 0.5, 0.75, 1, 2, 3, 4, 5, 6, 7, 8, 9, 10, 20, 30, 40, 50, 60, 70, 80, 90, 100, 110, 120, 130, 140, 150, 160, 170, 180, 190, 200, 0.1-0.2, 0.125-0.175, 0.13-0.17, 0.135-0.165, 0.14-0.16, 0.145-0.155, 10-80, 20-70, 30-60, 40-50, 50-200, 60-200, 70-200, 80-200, 90-200, 100-200, 110-200, 120-200, 50-180, 60-180, 70-180, 80-180, 90-180, 100-180, 110-180, 120-180, 50-160, 60-160, 70-160, 80-160, 90-160, 100-160, 110-160, 120-160, 50-140, 60-140, 70-140, 80-140, 90-140, 100-140, 110-140, 120-140, 50-120, 60-120, 70-120, 80-120, 90-120, 90-110, 100-120, 110-120, 50-110, 60-110, 70-110, 80-110, 90-110, 100-110, 50-100, 60-100, 70-100, 80-100, 90-100, or 95-105 million Daltons, for example. Prior to entering a graft copolymer herein into hydrolysis step (b), a graft copolymer can be either soluble, partly soluble, or insoluble. In some aspects, a graft copolymer is first treated with a dextranase (e.g., any as disclosed in U.S. Patent Appl. Publ. No. 2017/0218093, which is incorporated herein by reference) to remove some of, or all of, the dextran backbone of the copolymer (e.g., about, or at least about, 20%, 40%, 60%, 70%, 80%, 90%, 95%, or 99% by weight of the backbone is removed) before entering the graft copolymer into hydrolysis step (b). Optionally, this step can be conducted following hydrolysis step (b).

The temperature of an enzymatic reaction for producing an insoluble alpha-glucan precursor can be controlled, if desired, and can be about 5-50° C., 20-40° C., 30-40° C., 20-30° C., 20-25° C., 20° C., 25° C., 30° C., 35° C., or 40° C., for example. An enzymatic reaction can be conducted for about, at least about, or up to about, 1, 1.5, 2, 2.5, 3, 3.5, 4, 6, 8, 10, 12, 14, 16, 18, 20, 22, 24, 36, 48, 60, 72, 96, 120, 144, 168, 1-4, 1-3.5, 1-3, 1.5-4, 1.5-3.5, 1.5-3, 2-4, 2-3.5, or 2-3 hours, for example. The pH of an enzymatic reaction in some aspects can be about 4.0, 4.5, 5.0, 5.5, 6.0, 6.5, 7.0, 7.5, 8.0, 4.0-9.0, 4.0-8.5, 4.0-8.0, 5.0-8.0, 5.5-7.5, or 5.5-6.5.

The initial concentration of sucrose in an enzymatic reaction for producing an insoluble alpha-glucan precursor can be about, at least about, or less than about, 10, 15, 20, 25, 30, 40, 45, 50, 55, 60, 80, 90, 95, 100, 105, 110, 125, 150, 200, 300, 400, 500, 600, 10-50, 10-40, 10-30, 10-25, 15-50, 15-40, 15-30, or 15-25 g/L, or a range between any two of these values. "Initial concentration of sucrose" refers to the sucrose concentration in a reaction composition just after all the reaction components have been added/combined (e.g., at least water, sucrose, glucosyltransferase enzyme).

In some aspects, an enzymatic reaction for producing an insoluble alpha-glucan precursor can further comprise soluble gluco-oligosaccharide byproducts from a previously performed enzymatic reaction that produced insoluble alpha-glucan with at least 50% alpha-1,3-linkages. For example, soluble fraction (e.g., filtrate, precipitate) obtained from an enzymatic reaction that produced insoluble alpha-glucan with at least 50% (e.g., ≥95 or 99%) alpha-1,3-linkages can be added to an enzymatic reaction herein for producing an insoluble alpha-glucan precursor; such soluble fraction contains soluble gluco-oligosaccharide byproducts. Various ways to apply this approach herein are disclosed in U.S. Patent Appl. Publ. No. 2018/0340199, which is incorporated herein by reference.

Insoluble alpha-glucan precursor can optionally be isolated after its enzymatic production (above), prior to conducting hydrolysis step (b). In some aspects, isolating insoluble alpha-glucan precursor can include at least conducting a step of centrifugation, filtration, fractionation, chromatographic separation, dialysis, evaporation, or dilution. Isolation of insoluble alpha-glucan precursor can include at least conducting a step of preparing a cake of insoluble alpha-glucan precursor. Cake preparation can include at least conducting a step of centrifugation (cake is pelleted alpha-glucan) and/or filtration (cake is filtered alpha-glucan), for example. Isolation can optionally further comprise washing the centrifuged and/or filtered insoluble alpha-glucan precursor one, two, or more times with water or other aqueous liquid. A wash volume can optionally be at least about 10-100% of the volume of the reaction composition used to produce the alpha-glucan precursor. Washing can be done by various modes, as desired, such as by displacement or re-slurry washing. In some aspects, the aqueous portion of the resulting cake has no (detectable) dissolved sugars, or about, or less than about, 0.1-1.5, 0.1-1.25, 0.1-1.0, 0.1-0.75, 0.1-0.5, 0.2-0.6, 0.3-0.5, 0.3-0.4, 0.2, 0.3, 0.4, 0.5, or 0.6 wt % dissolved sugars. Such dissolved sugars can include sucrose, fructose, glucose, leucrose, and/or soluble gluco-oligosaccharides, for example. A cake of insoluble alpha-glucan precursor herein can remain wet ("never-dried"), for example, and in some aspects comprise (i) about 50%-90% by weight water or aqueous solution, and (ii) about 10%-50% by weight insoluble alpha-glucan precursor. A cake in some aspects can comprise about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 10-50, 10-40, 10-30, 10-20, 20-50, 20-40, 20-30, 30-50, 30-40, 40-50, 30-45, 35-45, 37.5-42.5, 35-40, or 40-45 wt % insoluble alpha-glucan precursor, for example (with water or aqueous solution adding up to 100 wt %). In some aspects, the aqueous portion of a cake has a solute and/or pH profile according to that as described for an aqueous solution herein.

Isolation herein can optionally further comprise drying alpha-glucan precursor, and/or preparing a dispersion of alpha-glucan precursor. An isolated insoluble alpha-glucan precursor herein as provided in a dry/dried form (optional) can comprise about, or no more than about, 12, 10, 8, 6, 5, 4, 3, 2, 1.5, 1.0, 0.5, 0.25, 0.10, 0.05, or 0.01 wt % water, for example. Drying can be done using an oven, freeze drying, spray drying, and/or by agitated air drying (e.g., agitated filter/film drying such as that under vacuum, fluidized bed drying, rotary drying such as drum drying). Drying in some aspects can be at a temperature of about, or at least about, 20, 25, 30, 40, 50, 60, 70, 80, 90, 100, 110, 120, 130, 140, 20-140, 20-130, 30-50, 35-45, 90-110, or 95-105° C., for example. A dispersion herein can comprise about 0.1, 0.25, 0.4, 0.5, 0.75, 1.0, 1.25, 1.5, 1.75, 2.0, 2.25, 2.5, 3.0, 4.0, 5.0, 6.0, 7.0, 8.0, 9.0, 10, 0.5-10, 1-10, 2-10, 3-10, 4-10, or 5-10 wt % insoluble alpha-glucan precursor in water or aqueous liquid, for example, and can be a dispersion of either never-dried or dried alpha-glucan precursor.

Step (b) of a method of producing insoluble alpha-glucan particles herein concerns hydrolyzing insoluble alpha-glucan precursor (above) to insoluble alpha-glucan particles under aqueous conditions at a pH of typically 2.0 or less. Dried or never-dried alpha-glucan precursor (above) can be entered into a hydrolysis reaction. In some aspects, a dispersion herein is first prepared, after which its pH is lowered accordingly to commence hydrolysis of insoluble alpha-glucan precursor to insoluble alpha-glucan of lower molecular weight.

The pH of a hydrolysis reaction herein can be 2.0 or less, for instance. In some aspects, the pH can be about, or less than about, 3.5, 3.0, 2.5, 2.0, 1.5, 1.0, 0.8, 0.6, 0.5, 0.4, 0.3, 0.2, 0.1, 0.05, 0.03, 0.01, 0.0, 0.0-2.0, 0.0-1.0, 0.0-0.5, 0.05-2.0, 0.05-1.0, 0.05-0.5, 0.1-2.0, 0.1-1.0, or 0.1-0.5. A strong mineral acid such as hydrochloric acid, nitric acid, sulfuric acid, hydrobromic acid, hydroiodic acid, or perchloric acid, can be used accordingly to achieve a low pH as disclosed in the foregoing. For example, mineral acid can be added to a dispersion of insoluble alpha-glucan precursor until a desired pH is reached, thereby initiating a hydrolysis reaction. A hydrolysis reaction herein typically is performed under aqueous conditions, where the liquid of the reaction comprises a solvent that is water or an aqueous solution comprising at least about 60, 70, 80, 90, 95, 98, or 99 wt % water. However, in some alternative aspects, a hydrolysis reaction herein can be conducted by exposing dry or moistened insoluble alpha-glucan precursor to hydrochloric gas (e.g., at a pressure of about or up to about 100 kPa).

The temperature of a hydrolysis reaction herein can be about, at least about, or less than about, 15, 20, 25, 30, 35, 40, 45, 50, 55, 60, 65, 70, 75, 80, 85, 90, 95, 100, 105, 110, 115, 120, 125, 130, 20-25, 20-30, 40-130, 40-125, 40-120, 70-130, 70-125, 70-120, 80-130, 80-125, 80-120, 60-100, 60-90, 70-100, 70-90, 75-100, 75-90, or 75-85° C., for example.

A hydrolysis reaction herein can proceed for about, at least about, or up to about, 1, 1.5, 2, 4, 6, 8, 10, 12, 14, 16, 18, 20, 22, 24, 30, 36, 42, 48, 60, 72, 96, 120, 144, 168, 192, 1-192, 1-120, 1-72, 6-192, 6-120, 6-72, 8-192, 8-120, 8-72, 20-192, 20-120, or 20-72 hours, for example. In some aspects, a hydrolysis reaction herein can proceed until the DPw of the hydrolyzed insoluble alpha-glucan is about 35-100 (e.g., 35-60, 40-60, 40-100), after which time the DPw no longer decreases (e.g., does not go below DPw 35 or 40). Typically, a hydrolysis reaction is agitated (e.g., stirred, shaken).

As desired, the pH of a hydrolysis reaction can be neutralized (e.g., brought to pH 6-8) or otherwise raised above pH 2, 3, 4, 5, or 6 following completion of the reaction. Neutralization typically can be accomplished by adding a base such as a hydroxide (e.g., NaOH) or bicarbonate (e.g., $NaHCO_3$).

Insoluble alpha-glucan particle products of the reaction optionally can be isolated (step c) (e.g., washed, dispersed, and/or dried) following any of the above procedures regarding isolating/processing of enzymatically synthesized insoluble alpha-glucan precursor. In some aspects, insoluble alpha-glucan particles that have been isolated (optionally characterized as "purified") can be present in a composition at a wt % (dry weight basis) of at least about 50%, 60%, 70%, 80%, 85%, 90%, 91%, 92%, 93%, 94%, 95%, 96%, 97%, 98%, 98.5%, 99%, 99.5%, 99.8%, or 99.9%. Such isolated insoluble alpha-glucan particles can be used as an ingredient/component in a product/application, for example.

The DPw or DPn of an insoluble alpha-glucan product of a hydrolysis reaction herein can be about 35-100, for example (or up to about 100, for example). In some aspects, its DPw or DPn can be about 35-100, 35-90, 35-80, 35-70, 35-60, 35-55, 35-50, 40-100, 40-90, 40-80, 40-70, 40-60, 40-55, 40-50, 45-100, 45-90, 45-80, 45-70, 45-60, 45-55, or 45-50.

Any of the features disclosed herein for insoluble alpha-glucan particles (e.g., glycosidic linkage profile, crystallinity, plate characteristics and wt % content of plates, diameter, dispersion stability, dispersion viscosity, optical clarity, pigment extender capacity) can likewise characterize an insoluble alpha-glucan product of a hydrolysis method of the present disclosure.

Some embodiments of the present disclosure concern a method of providing an aqueous composition that comprises insoluble alpha-glucan particles. Such a method typically comprises (a) providing insoluble alpha-glucan particles as presently disclosed, and (b) dispersing the particles into an aqueous liquid, thereby producing an aqueous composition that comprises insoluble alpha-glucan particles. This method can optionally be characterized as a dispersion method.

Insoluble alpha-glucan particles provided in step (a) of a dispersion method herein can be dry/dried or wet. A dry form of alpha-glucan particles can comprise about, or no more than about, 12, 10, 8, 6, 5, 4, 3, 2, 1.5, 1.0, 0.5, 0.25, 0.10, 0.05, or 0.01 wt % water, for example. A wet form of alpha-glucan particles can be a cake (filter cake, wet cake) in some aspects. A cake of insoluble alpha-glucan particles herein can remain wet ("never-dried"), for example, and in some aspects comprise (i) about 50%-90% by weight water or aqueous solution, and (ii) about 10%-50% by weight insoluble alpha-glucan particles. A cake in some aspects can comprise about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 10-50, 10-40, 10-30, 10-20, 20-50, 20-40, 20-30, 30-50, 30-40, 40-50, 30-45, 35-45, 37.5-42.5, 35-40, or 40-45 wt % insoluble alpha-glucan particles, for example (with water or aqueous solution adding up to 100 wt %). In some aspects, the aqueous portion of a cake has a solute and/or pH profile according to that as described for an aqueous solution herein.

Any suitable method can be employed to perform step (b) of dispersing insoluble alpha-glucan particles. In some aspects, such dispersal can be performed by applying high shear and/or other forms of mixing/agitation. High shear can be of about, or at least about, 8, 9, 10, 11, or 12 kJ/kg in specific energy, and/or can comprise mixing at about, or up to about, 3000, 4000, 6000, 8000, 10000, 12000, 14000, or 15000 rpm, for example. High shear and/or mixing/agitation can be applied for about 1, 2, 3, 4, 5, 6, 8, or 10 minutes, or 2-4 minutes, for example. Suitable means for shearing/mixing/agitating include, for example, a disperser, sonicator (e.g., ultrasonicator) (e.g., 40-60 W, ~50 W), homomixer, homogenizer (e.g., rotary or piston, rotar-stator), microfluidizer, planetary mixer, colloid mill, jet mill, vortex, and/or any methodology as described in International Patent Appl. Publ. No. WO2016/030234, U.S. Pat. Nos. 5,767,176, 6,139,875 and 8,722,092, and U.S. Patent Appl. Publ. Nos. 2017/0055540 and 2018/0021238, which are all incorporated herein by reference. In some aspects, high shear mixing (such as applied by any of the foregoing means) is not used to disperse insoluble alpha-glucan particles to achieve elevated viscosity; gentle mixing/agitation such at a low rpm/frequency (e.g., less than about 100, 50, or 30 rpm) is used to disperse the insoluble alpha-glucan particles in such aspects. A dispersion produced herein can optionally be a colloidal dispersion.

An aqueous composition produced by a dispersion method herein can comprise about, at least about, or less than about, 0.1, 0.25, 0.4, 0.5, 0.75, 1.0, 1.25, 1.5, 1.75, 2.0, 2.25, 2.5, 3.0, 4.0, 5.0, 6.0, 7.0, 8.0, 9.0, 10.0, 0.5-10, 1-10, 2-10, 3-10, 4-10, or 5-10 wt % insoluble alpha-glucan particles, for example.

In some aspects, the viscosity of the aqueous composition produced in step (b) of a dispersion method is at least about 10%, 50%, 75%, 100%, 500%, 1000%, 10000%, 100000%, or 1000000% (or any integer between 10% and 100000%) higher than the viscosity of the aqueous liquid as it existed before step (b) of dispersing. Very large percent increases in viscosity can be obtained with the disclosed method when the aqueous liquid has little to no viscosity before step (b). The viscosity of an aqueous composition comprising insoluble alpha-glucan particles herein can be about, or at least about, 2.5, 5, 10, 100, 200, 300, 400, 500, 600, 700, 1000, 2000, 3000, 4000, 5000, 6000, 7000, 8000, 9000, 10000, or 15000 centipoise (cps), for example. Viscosity can be as measured with an aqueous composition at any temperature between about 3° C. to about 80° C., for example (e.g., 4-30° C., 15-30° C., 15-25° C.). Viscosity typically is as measured at atmospheric pressure (about 760 torr) or a pressure that is ±10% thereof. Viscosity can be measured using a viscometer or rheometer, for example, and can optionally be as measured at a shear rate (rotational shear rate) of about 0.1, 0.5, 1.0, 1.667, 2, 5, 10, 50, 100, 500, 1000, 0.1-500, 0.1-100, 1.0-500, 1.0-1000, or 1.0-100 $s^{-1}$ (1/s), for example. Viscosity can optionally be measured following the procedure outlined in the below Examples.

It is notable that dispersions of insoluble alpha-glucan particles herein typically have enhanced viscosity (at any given shear rate) compared to insoluble alpha-glucan (e.g., non-hydrolyzed) of DPw>200 (e.g., DPw~700 or ~800), crystallinity <0.65 (e.g., ≤0.60), and/or D50 diameter of 5-50 microns (where each polymer is provided in the same amount). Such viscosity enhancement can be about, or at least about, a 10-fold, 25-fold, 50-fold, 75-fold, 100-fold, or 125-fold increase in viscosity (at any given shear rate). It is notable that dispersions of insoluble alpha-glucan particles herein, whether at a neutral pH (e.g., pH 6-8) or a low pH (e.g., pH≤2 or 3), typically retain the same or similar (e.g., ±10%) viscosity profile/level (where polymer is provided in the same amount).

It is notable that dry insoluble alpha-glucan particles (e.g., dried at least once following synthesis in hydrolysis reaction) and never-dried wet insoluble alpha-glucan particles (never dried following synthesis in hydrolysis reaction) herein are typically both able to increase viscosity to the same or similar extent when dispersed in aqueous conditions (e.g., within about 10, 20, 30, 40, or 50% of the viscosity of the never-dried glucan dispersion), whereas insoluble alpha-glucan (e.g., non-hydrolyzed) of DPw>200 (e.g., DPw≥~700 or ~800), crystallinity <0.65 (e.g., ≤0.60), and/or D50 diameter of 5-50 microns typically does not exhibit this beneficial feature. When the latter alpha-glucan is dried at least once, it typically is not capable of increasing viscosity to the same or similar extent as its never-dried wet form (e.g., viscosity of dried glucan dispersion can be less than 10%, 5%, 2.5%, 1%, 0.5%, or 0.1% of viscosity of never-dried glucan dispersion).

It is notable that aqueous dispersions of insoluble alpha-glucan particles herein typically have enhanced stability in that the particles are able to remain dispersed following formation of the dispersion. For example, in an aqueous dispersion comprising insoluble alpha-glucan particles herein, the particles are dispersed through about, or at least about, 80%, 85%, 90%, 95%, 98%, 99%, or 100% of the volume of the dispersion. In some aspects, such a level of dispersion is contemplated to be for a time (typically beginning from initial preparation of the dispersion) of about, at least about, or up to about, 0.5, 1, 2, 4, 6, 8, 10, 20, 30, 60, 90, 120, 150, 180, 210, 240, 270, 300, 330, or 360 days, or 1, 2, or 3 years, optionally at a temperature of about, or up to about, 15, 20, 25, 30, 35, 40, 50, 60, 70, or 80° C., and/or at a pH of about, or up to about, 0, 1, 2, 3, 4, 5, 6, 7, 8, or 9 (any of these volume parameters and/or conditions can optionally also apply to stable dispersions and stable emulsions as defined above). In some aspects, stability can additionally or alternatively refer to the particles having an enhanced ability to provide viscosity to an aqueous composition (e.g., any of the above viscosity levels, optionally for any of the above time periods), and/or maintain a molecular weight (DPw) as disclosed above. In some aspects, dispersion of insoluble alpha-glucan particles in an emulsion confers stability to the emulsion; for example, any of the above dispersal-volume percentages and/or times of such stability can likewise characterize dispersed/emulsified droplets. In some aspects, stability can additionally or alternatively characterize an emulsion in which the average emulsion droplet size is relatively small (e.g., about, or less than about, 40, 38, 36, 34, 32, 30, 28, 26, 26-34, 26-32, 26-30, 28-34, 28-32, or 28-30 microns in diameter) and typically uniform in size (e.g., standard deviation of average size about, or less than about, 12, 11, 10, 9, 8, 7, 6, 5, 4, 5-10, 5-8, 6-10, 6-8). A small average droplet size equates to an elevated total droplet surface area. In some aspects, stability can additionally or alternatively characterize an emulsion having an average storage modulus (Avg. G') (also referred to as elastic modulus) of about, or at least about, 40, 50, 60, 70, 80, 90, 100, 125, 150, 40-150, 40-125, 40-100, 50-150, 50-125, or 50-100 Pascals. The storage modulus of an emulsion herein can be measured according to the below Examples, or as disclosed in Varanasi et al. (2018, *Frontiers Chem.* 6:1-9, Article 409, incorporated herein by reference), for example. Based on the foregoing emulsion stabilizing effects of insoluble alpha-glucan particles herein, it is contemplated that the particles can be used in an application/product in which emulsion stabilization improves the performance of the application/product (though such is not a requirement for the particles to be used in the application/product). Examples of such applications/products can be as disclosed herein, such as milk/dairy products (e.g., yogurt, ice cream, cream), mayonnaise, salad dressings, beverages/tonics as carriers for delivering non-polar bioactive ingredients, cosmetic or pharmaceutical lotions/creams, waterborne/latex paints, defoaming formulations, rolling oils for metal working, mining explosives, agrochemical formulations, downhole fluids such as for enhanced oil recovery operations, or pharmaceutical carrier or encapsulation systems.

An emulsion comprising insoluble alpha-glucan particles in some aspects can further comprise fibrids comprising alpha-glucan comprising alpha-1,3 linkages. The linkage and/or molecular weight profile of the alpha-glucan of fibrids herein can be as disclosed herein for the insoluble alpha-glucan particles. Alpha-glucan fibrids can be as disclosed in U.S. Pat. Appl. Publ. No. 2018/0119357, for example, which is incorporated herein by reference. In some aspects, including fibrids in an emulsion can have a synergistic effect with the insoluble particles on emulsion stability. The concentration of fibrids in an emulsion of the disclosure can be any concentration as disclosed herein for insoluble alpha-glucan particles in an aqueous composition.

In some aspects, insoluble alpha-glucan particles as dispersed in a liquid such as water or an aqueous solution have a light-scattering effect on the liquid. For example, visible light can be scattered by about, at least about, or up to about, 0.1, 0.25, 0.5, 0.75, 1.0, 1.25, 1.5, 1.75, 2.0, 2.25, 2.5, 2.75, or 3.0 arbitrary units (a.u.). Visible light in some aspects can have a wave-length of about 380-750, 380-700, 380-650, 380-600, 380-550, 425-750, 425-700, 425-650, 425-600, 425-550, 450-550, or 475-525 nm. The concentration of the insoluble alpha-glucan particles as dispersed in a liquid for light scattering can be any concentration as disclosed herein, for example, be at about, or at least about, 0.05-10, 0.1-10, 1-10, 0.05-8, 0.1-8, or 1-8 wt %. In additional or other aspects, insoluble alpha-glucan particles as dispersed in a liquid do not absorb, or absorb very little (e.g., <1%, <0.1%), visible light that is radiated on the dispersion.

Insoluble alpha-glucan particles of the present disclosure can be present in a composition, such as an aqueous composition (e.g., dispersion such as colloidal dispersion) or dry composition, at about, at least about, or less than about, 0.01, 0.05, 0.1, 0.2, 0.25, 0.3, 0.4, 0.5, 0.6, 0.7, 0.75, 0.8, 0.9, 1.0, 1.2, 1.25, 1.4, 1.5, 1.6, 1.75, 1.8, 2.0, 2.25, 2.5, 3.0, 3.5, 4.0, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 wt % or w/v %, for example, or a range between any two of these values. The liquid component of an aqueous composition can be an aqueous fluid such as water or aqueous solution, for instance. The solvent of an aqueous solution typically is water, or can comprise about, or at least about, 10, 20, 30, 40, 50, 60, 70, 80, 90, 95, 98, or 99 wt % water, for example.

An aqueous solution of an aqueous composition in some aspects has no (detectable) dissolved sugars, or about 0.1-1.5, 0.1-1.25, 0.1-1.0, 0.1-0.75, 0.1-0.5, 0.2-0.6, 0.3-0.5, 0.2, 0.3, 0.4, 0.5, or 0.6 wt % dissolved sugars. Such dissolved sugars can include sucrose, fructose, leucrose, and/or soluble gluco-oligosaccharides, for example. An aqueous solution of an aqueous composition in some aspects can have one or more salts/buffers (e.g., Na$^+$, Cl$^-$, NaCl, phosphate, tris, citrate) (e.g., ≤0.1, 0.5, 1.0, 2.0, or 3.0 wt %) and/or a pH of about, or less than about, 0.0, 0.01, 0.03, 0.05, 0.1, 0.2, 0.3, 0.4, 0.5, 0.6, 0.8, 1.0, 1.5, 2.0, 2.5, 3.0, 3.5, 4.0, 4.5, 5.0, 5.5, 6.0, 6.5, 7.0, 7.5, 8.0, 8.5, 0.0-1.0, 0.0-2.0, 0.0-3.0, 0.0-4.0, 0.0-5.0, 9.0, 4.0-9.0, 4.0-8.5, 4.0-8.0, 5.0-9.0, 5.0-8.5, 5.0-8.0, 6.0-9.0, 6.0-8.5, or 6.0-8.0, for example. In some aspects, an aqueous composition comprising insoluble alpha-glucan particles herein can be an acid hydrolysis reaction as presently disclosed; the aqueous portion of the reaction has a correspondingly low pH (as above).

An aqueous composition comprising insoluble alpha-glucan particles herein (e.g., an aqueous dispersion) can have a viscosity of about, or at least about, 2.5, 5, 10, 100, 200, 300, 400, 500, 600, 700, 1000, 2000, 3000, 4000, 5000, 6000, 7000, 8000, 9000, 10000, or 15000 centipoise (cps), for example. Viscosity can be measured as disclosed above or in the below Examples. Typically, insoluble alpha-glucan particles in an aqueous dispersion are dispersed through about, or at least about, 80%, 85%, 90%, 95%, 98%, 99%, or 100% of the volume of the dispersion.

The temperature of a composition comprising insoluble alpha-glucan particles herein (e.g., aqueous composition) can be about, or up to about, 0, 5, 10, 15, 20, 25, 30, 35, 40, 45, 50, 55, 60, 65, 70, 75, 80, 85, 90, 95, 100, 105, 110, 115, 120, 125, 130, 5-50, 20-25, 20-30, 20-40, 30-40, 40-130, 40-125, 40-120, 70-130, 70-125, 70-120, 80-130, 80-125, 80-120, 60-100, 60-90, 70-100, 70-90, 75-100, 75-90, or 75-85° C., for example.

A composition comprising insoluble alpha-glucan particles herein can, in some aspects, be non-aqueous (e.g., a dry composition). Examples of such embodiments include powders, granules, microcapsules, flakes, or any other form of particulate matter. Other examples include larger compositions such as pellets, bars, kernels, beads, tablets, sticks, or other agglomerates. A non-aqueous or dry composition typically has about, or no more than about, 12, 10, 8, 6, 5, 4, 3, 2, 1.5, 1.0, 0.5, 0.25, 0.10, 0.05, or 0.01 wt % water comprised therein. In some aspects (e.g., those directed to laundry or dish washing detergents), a dry composition herein can be provided in a sachet or pouch.

A composition comprising insoluble alpha-glucan particles herein can, in some aspects, comprise one or more salts such as a sodium salt (e.g., NaCl, $Na_2SO_4$). Other non-limiting examples of salts include those having (i) an aluminum, ammonium, barium, calcium, chromium (II or III), copper (I or II), iron (II or III), hydrogen, lead (II), lithium, magnesium, manganese (II or III), mercury (I or II), potassium, silver, sodium strontium, tin (II or IV), or zinc cation, and (ii) an acetate, borate, bromate, bromide, carbonate, chlorate, chloride, chlorite, chromate, cyanamide, cyanide, dichromate, dihydrogen phosphate, ferricyanide, ferrocyanide, fluoride, hydrogen carbonate, hydrogen phosphate, hydrogen sulfate, hydrogen sulfide, hydrogen sulfite, hydride, hydroxide, hypochlorite, iodate, iodide, nitrate, nitrite, oxalate, oxide, perchlorate, permanganate, peroxide, phosphate, phosphide, phosphite, silicate, stannate, stannite, sulfate, sulfide, sulfite, tartrate, or thiocyanate anion. Thus, any salt having a cation from (i) above and an anion from (ii) above can be in a composition, for example. A salt can be present in an aqueous composition herein at a wt % of about, or at least about, 0.01, 0.025, 0.05, 0.075, 0.1, 0.25, 0.5, 0.75, 1.0, 1.25, 1.5, 1.75, 2.0, 2.5, 3.0, 3.5, 0.01-3.5, 0.5-3.5, 0.5-2.5, or 0.5-1.5 wt % (such wt % values typically refer to the total concentration of one or more salts), for example.

A composition comprising insoluble alpha-glucan particles herein can optionally contain one or more active enzymes. Examples of suitable enzymes include proteases, cellulases, hemicellulases, peroxidases, lipolytic enzymes (e.g., metallolipolytic enzymes), xylanases, lipases, phospholipases, esterases (e.g., arylesterase, polyesterase), perhydrolases, cutinases, pectinases, pectate lyases, mannanases, keratinases, reductases, oxidases (e.g., choline oxidase), phenoloxidases, lipoxygenases, ligninases, pullulanases, tannases, pentosanases, malanases, beta-glucanases, arabinosidases, hyaluronidases, chondroitinases, laccases, metalloproteinases, amadoriases, glucoamylases, arabinofuranosidases, phytases, isomerases, transferases, nucleases, and amylases. If an enzyme(s) is included, it may be comprised in a composition herein at about 0.0001-0.1 wt % (e.g., 0.01-0.03 wt %) active enzyme (e.g., calculated as pure enzyme protein), for example. In fabric care applications, an enzyme (e.g., any of the above such as cellulase) can be present in an aqueous composition in which a fabric is treated (e.g., wash liquor) at a concentration that is minimally about 0.01-0.1 ppm total enzyme protein, or about 0.1-10 ppb total enzyme protein (e.g., less than 1 ppm), to maximally about 100, 200, 500, 1000, 2000, 3000, 4000, or 5000 ppm total enzyme protein, for example.

A composition comprising insoluble alpha-glucan particles herein, such as an aqueous composition or a non-aqueous composition (above), can be in the form of a household care product, personal care product, industrial product, ingestible product (e.g., food product), or pharmaceutical product, for example. Examples of such products can be as described in any of U.S. Patent Appl. Publ. Nos. 2018/0022834, 2018/0237816, 2018/0230241, 20180079832, 2016/0311935, 2016/0304629, 2015/0232785, 2015/0368594, 2015/0368595, 2016/0122445, 2019/0309096, or 2019/0202942, or International Patent Appl. Publ. Nos. WO2016/133734 and WO2017/218391, which are all incorporated herein by reference. In some aspects, a composition comprising insoluble alpha-glucan particles can comprise at least one component/ingredient of a household care product, personal care product, industrial product, pharmaceutical product, or ingestible product (e.g., food product) as disclosed in any of the foregoing publications and/or as presently disclosed.

Insoluble alpha-glucan particles disclosed herein are believed to be useful for providing one or more of the following physical properties to a personal care product, pharmaceutical product, household product, industrial product, or ingestible product (e.g., food product): thickening, freeze/thaw stability, lubricity, moisture retention and release, texture, consistency, shape retention, emulsification, binding, suspension, dispersion, gelation, reduced mineral hardness, for example. Examples of a concentration or amount of insoluble alpha-glucan particles in a product can be any of the weight percentages provided herein, for example.

Personal care products herein are not particularly limited and include, for example, skin care compositions, cosmetic compositions, antifungal compositions, and antibacterial compositions. Personal care products herein may be in the form of, for example, lotions, creams, pastes, balms, ointments, pomades, gels, liquids, combinations of these and the like. The personal care products disclosed herein can include at least one active ingredient, if desired. An active ingredient is generally recognized as an ingredient that causes an intended cosmetic or pharmacological effect.

In certain embodiments, a skin care product can be applied to skin for addressing skin damage related to a lack of moisture. A skin care product may also be used to address the visual appearance of skin (e.g., reduce the appearance of flaky, cracked, and/or red skin) and/or the tactile feel of the skin (e.g., reduce roughness and/or dryness of the skin while improved the softness and subtleness of the skin). A skin care product typically may include at least one active ingredient for the treatment or prevention of skin ailments, providing a cosmetic effect, or for providing a moisturizing benefit to skin, such as zinc oxide, petrolatum, white petrolatum, mineral oil, cod liver oil, lanolin, dimethicone, hard fat, vitamin A, allantoin, calamine, kaolin, glycerin, or colloidal oatmeal, and combinations of these. A skin care product may include one or more natural moisturizing factors such as ceramides, hyaluronic acid, glycerin, squalane, amino acids, cholesterol, fatty acids, triglycerides, phospholipids, glycosphingolipids, urea, linoleic acid, glycosaminoglycans, mucopolysaccharide, sodium lactate, or sodium pyrrolidone carboxylate, for example. Other ingredients that may be included in a skin care product include, without limitation, glycerides, apricot kernel oil, canola oil, squalane, squalene, coconut oil, corn oil, jojoba oil, jojoba wax, lecithin, olive oil, safflower oil, sesame oil, shea butter, soybean oil, sweet almond oil, sunflower oil, tea tree oil, shea butter, palm oil, cholesterol, cholesterol esters, wax esters, fatty acids, aloe vera, and orange oil.

A personal care product herein can also be in the form of makeup, lipstick, mascara, rouge, foundation, blush, eyeliner, lip liner, lip gloss, other cosmetics, sunscreen, sun block, nail polish, nail conditioner, bath gel, shower gel, body wash, face wash, lip balm, skin conditioner, cold cream, moisturizer, body spray, soap, body scrub, exfoliant, astringent, scruffing lotion, depilatory, permanent waving solution, antidandruff formulation, antiperspirant composition, deodorant, shaving product, pre-shaving product, after-shaving product, cleanser, skin gel, rinse, dentifrice composition, toothpaste, or mouthwash, for example. An example of a personal care product (e.g., a cleanser, soap, scrub, cosmetic) comprises a carrier or exfoliation agent (e.g., jojoba beads [jojoba ester beads]) (e.g., about 1-10, 3-7, 4-6, or 5 wt %); such an agent may optionally be dispersed within the product.

A personal care product in some aspects can be a hair care product. Examples of hair care products herein include shampoo, hair conditioner (leave-in or rinse-out), cream rinse, hair dye, hair coloring product, hair shine product, hair serum, hair anti-frizz product, hair split-end repair product, mousse, hair spray, and styling gel. A hair care product can be in the form of a liquid, paste, gel, solid, or powder in some embodiments. A hair care product as presently disclosed typically comprises one or more of the following ingredients, which are generally used to formulate hair care products: anionic surfactants such as polyoxyethylenelauryl ether sodium sulfate; cationic surfactants such as stearyltrimethylammonium chloride and/or distearyltrimethylammonium chloride; nonionic surfactants such as glyceryl monostearate, sorbitan monopalmitate and/or polyoxyethylenecetyl ether; wetting agents such as propylene glycol, 1,3-butylene glycol, glycerin, sorbitol, pyroglutamic acid salts, amino acids and/or trimethylglycine; hydrocarbons such as liquid paraffins, petrolatum, solid paraffins, squalane and/or olefin oligomers; higher alcohols such as stearyl alcohol and/or cetyl alcohol; superfatting agents; antidandruff agents; disinfectants; anti-inflammatory agents; crude drugs; water-soluble polymers such as methyl cellulose, hydroxycellulose and/or partially deacetylated chitin; antiseptics such as paraben; ultra-violet light absorbers; pearling agents; pH adjustors; perfumes; and pigments.

A pharmaceutical product herein can be in the form of an emulsion, liquid, elixir, gel, suspension, solution, cream, or ointment, for example. Also, a pharmaceutical product herein can be in the form of any of the personal care products disclosed herein, such as an antibacterial or antifungal composition. A pharmaceutical product can further comprise one or more pharmaceutically acceptable carriers, diluents, and/or pharmaceutically acceptable salts. Insoluble alpha-glucan particles disclosed herein can also be used in capsules, beads, pastilles, encapsulants, tablets, tablet coatings, and as an excipients for medicaments and drugs.

A composition herein comprising insoluble alpha-glucan particles can be an encapsulant, for instance. An encapsulant can be used for controlling the release of, and/or protecting, the material and/or active agent(s)/compound(s) held within the encapsulant, for instance. An encapsulant herein can encapsulate a fragrance (e.g., any as disclosed in U.S. Pat. No. 7,196,049, which is incorporated herein by reference), ingestible product (e.g., food, beverage, a flavor such as disclosed in U.S. Pat. No. 7,022,352, which is incorporated herein by reference), pharmaceutical or health product (e.g., liquid drug, prebiotic, probiotic), personal care product (e.g., toothpaste, mouth wash, face/body cream), household care product (e.g., dry or liquid detergent, bleach). Any suitable composition/product disclosed elsewhere herein (with or without alpha-glucan particles), or as disclosed in U.S. Patent Appl. Publ. Nos. 2009/0209661 or 2007/0148105 (each incorporated herein by reference, e.g., consumer product) can be encapsulated, for example. In some aspects, an encapsulant herein can encapsulate a hydrophobic or non-polar composition; a hydrophobic or non-polar composition can comprise a lipid (e.g., oil, essential oil, fat, wax, free fatty acids, glycerol, phospholipids, sterols, triglycerides, diglycerides, monoglycerides), alkane, alkene/olefin, a hydrophobic aromatic or cyclic compound, a hydrophobic aroma compound, and/or a hydrophobic flavorant or nutrient, for example. An encapsulated product herein can be in a dry form in some aspects. An encapsulant in some cases can have a composition/formulation, and/or thickness, that is the same as, or similar to, that of a film or coating herein, where such film or coating is suitable for use as an encapsulant. An encapsulant can comprise about, or at least about, 50, 60, 70, 80, 90, 91, 92, 93, 94, 95, 96, 97, 98, 99, or 100 wt % insoluble alpha-glucan particles, for example. This and/or other encapsulants herein can further comprise, in some aspects, polyurethane, poly acrylate, poly lactic acid, polysaccharide (in addition to the alpha-glucan particles), gelatin, melamine, and/or formaldehyde. One or more additional additives can optionally be included that alter the mechanical, thermal, and/or degradation profile of an encapsulant herein.

In some aspects, an encapsulated composition as presently disclosed can be produced by a method comprising: (a) providing a liquid emulsion comprising at least insoluble alpha-1,3-glucan herein, water and a liquid/compound that is immiscible in water (e.g., any hydrophobic or non-polar substance disclosed herein), and (b) removing all or most (≥88%, 90%, 95%, 98%, 99%, 99.5%, 99.9% by weight) of the water from the emulsion. Such removal can comprise drying such as by freeze-drying or spray-drying. A liquid emulsion can be provided in an encapsulation method, for example, by mixing and/or homogenizing the foregoing emulsion components. In some aspects, the temperature of the mixture to be emulsified is increased to aid emulsification. For example, the temperature can be raised in order to liquify/melt a non-water component (immiscible component), such as a component that is solid at room temperature (e.g., the temperature is raised at least 1 or 2° C. above the melting point of the immiscible component), thereby providing the liquid/compound that is immiscible in water. The increased temperature of the emulsification is typically maintained until the point of entering the emulsification to the drying step. In an encapsulation method herein, it should be understood that, regarding the product of the method, the liquid/compound (or solid, as the case may be, depending on melting point) that is immiscible in water is encapsulated by a composition comprising insoluble alpha-1,3-glucan. Conditions (e.g., temperature, pressure, time, and/or air flow rate) for preparing an encapsulated product herein, such as by freeze-drying or spray-drying, can be the same as, or similar to (e.g., within 5%, 10%, 15%, or 20% of the stated values), the values disclosed below in Example 7, for example. In some alternative aspects of an encapsulation method of the present disclosure, the alpha-1,3-glucan can be in the form of an alpha-glucan precursor herein.

A household and/or industrial product herein can be in the form of drywall tape-joint compounds; mortars; grouts; cement plasters; spray plasters; cement stucco; adhesives; pastes; wall/ceiling texturizers; binders and processing aids for tape casting, extrusion forming, injection molding and ceramics; spray adherents and suspending/dispersing aids for pesticides, herbicides, and fertilizers; fabric care products such as fabric softeners and laundry detergents; hard surface cleaners; air fresheners; polymer emulsions; latex; gels such as water-based gels; surfactant solutions; paints such as water-based paints; protective coatings; adhesives; sealants and caulks; inks such as water-based ink; metalworking fluids; films or coatings; or emulsion-based metal cleaning fluids used in electroplating, phosphatizing, galvanizing and/or general metal cleaning operations, for example.

Examples of ingestible products herein include a food, beverage, animal feed, an animal health and/or nutrition product, and/or pharmaceutical product. The intended use of insoluble alpha-glucan particles as presently disclosed in an ingestible product can be to provide texture, add volume, and/or thicken, for example.

Further examples of using insoluble alpha-glucan particles of the present disclosure for ingestible products include use as: a bulking, binding and/or coating ingredient; a carrier for coloring agents, flavors/fragrances, and/or high intensity sweeteners; a spray drying adjunct; a bulking, bodying, dispersing and/or emulsification agent; and an ingredient for promoting moisture retention (humectant). Illustrative examples of products that can be prepared having insoluble alpha-glucan particles herein include food products, beverage products, pharmaceutical products, nutritional products, and sports products. Examples of beverage products herein include concentrated beverage mixes, carbonated beverages, non-carbonated beverages, fruit-flavored beverages, fruit juices, teas, coffee, milk nectars, powdered drinks, liquid concentrates, milk drinks, ready-to-drink (RTD) products, smoothies, alcoholic beverages, flavored waters and combinations thereof. Examples of food products herein include baked goods (e.g., breads), confectioneries, frozen dairy products, meats, artificial/synthetic/cultured meat, cereal products (e.g., breakfast cereals), dairy products (e.g., yogurt), condiments (e.g., mustard, ketchup, mayonnaise), snack bars, soups, dressings, mixes, prepared foods, baby foods, diet preparations, peanut butter, syrups, sweeteners, food coatings, pet food, animal feed, animal health and nutrition products, dried fruit, sauces, gravies, jams/jellies, dessert products, spreads, batters, breadings, spice mixes, frostings and the like. In some aspects, insoluble alpha-glucan particles can provide or enhance the foaming of beverages such as dairy beverages, non-dairy alternative beverages (e.g., "vegan" milk such as soy milk, almond milk, or coconut milk), dairy creamers, and/or non-dairy creamers (e.g., for a hot beverage such as coffee [e.g., cappuccino], tea [e.g., chai tea]).

Insoluble alpha-glucan particles disclosed herein can be comprised in a personal care product, pharmaceutical product, household product, industrial product, or ingestible product (e.g., food product) in an amount that provides a desired degree of thickening and/or dispersion, for example. Examples of a concentration or amount of insoluble alpha-glucan particles in a product are any of the weight percentages provided above.

Compositions disclosed herein can be in the form of a detergent composition such as a fabric care composition. A fabric care composition herein can be used for hand wash, machine wash and/or other purposes such as soaking and/or pretreatment of fabrics, for example. A fabric care composition may take the form of, for example, a laundry detergent; fabric conditioner; any wash-, rinse-, or dryer-added product; unit dose or spray. Fabric care compositions in a liquid form may be in the form of an aqueous composition as disclosed herein. In other aspects, a fabric care composition can be in a dry form such as a granular detergent or dryer-added fabric softener sheet. Other non-limiting examples of fabric care compositions herein include: granular or powder-form all-purpose or heavy-duty washing agents; liquid, gel or paste-form all-purpose or heavy-duty washing agents; liquid or dry fine-fabric (e.g. delicates) detergents; cleaning auxiliaries such as bleach additives, "stain-stick", or pre-treatments; substrate-laden products such as dry and wetted wipes, pads, or sponges; sprays and mists.

A detergent composition herein may be in any useful form, e.g., as powders, granules, pastes, bars, unit dose, or liquid. A liquid detergent may be aqueous, typically containing up to about 70 wt % of water and 0 wt % to about 30 wt % of organic solvent. It may also be in the form of a compact gel type containing only about 30 wt % water.

A detergent composition herein typically comprises one or more surfactants, wherein the surfactant is selected from nonionic surfactants, anionic surfactants, cationic surfactants, ampholytic surfactants, zwitterionic surfactants, semi-polar nonionic surfactants and mixtures thereof. In some embodiments, the surfactant is present at a level of from about 0.1% to about 60%, while in alternative embodiments the level is from about 1% to about 50%, while in still further embodiments the level is from about 5% to about 40%, by weight of the detergent composition. A detergent will usually contain 0 wt % to about 50 wt % of an anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. In addition, a detergent composition may optionally contain 0 wt % to about 40 wt % of a nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO92/06154, which is incorporated herein by reference).

A detergent composition herein typically comprises one or more detergent builders or builder systems. In some aspects, oxidized alpha-1,3-glucan can be included as a co-builder, in which it is used together with one or more additional builders such as any disclosed herein. Oxidized alpha-1,3-glucan compounds for use herein are disclosed in U.S. Patent Appl. Publ. No. 2015/0259439. In some embodiments incorporating at least one builder, the cleaning compositions comprise at least about 1%, from about 3% to about 60%, or even from about 5% to about 40%, builder by weight of the composition. Builders (in addition to oxidized alpha-1,3-glucan) include, but are not limited to, alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present disclosure. Additional examples of a detergent builder or complexing agent include zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst).

In some embodiments, builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present disclosure, including those known in the art (See, e.g., EP2100949).

In some embodiments, suitable builders can include phosphate builders and non-phosphate builders. In some embodiments, a builder is a phosphate builder. In some embodiments, a builder is a non-phosphate builder. A builder can be used in a level of from 0.1% to 80%, or from 5% to 60%, or from 10% to 50%, by weight of the composition. In some embodiments, the product comprises a mixture of phosphate and non-phosphate builders. Suitable phosphate builders include mono-phosphates, di-phosphates, tri-polyphosphates or oligomeric-polyphosphates, including the alkali metal salts of these compounds, including the sodium salts. In some embodiments, a builder can be sodium tripolyphosphate (STPP). Additionally, the composition can comprise carbonate and/or citrate, preferably citrate that helps to achieve a neutral pH composition. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include ammonium and/or alkali metal salts, i.e., lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

A detergent composition herein can comprise at least one chelating agent. Suitable chelating agents include, but are not limited to copper, iron and/or manganese chelating agents and mixtures thereof. In embodiments in which at least one chelating agent is used, the composition comprises from about 0.1% to about 15%, or even from about 3.0% to about 10%, chelating agent by weight of the composition.

A detergent composition herein can comprise at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

A detergent composition herein can comprise one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. Additional dye transfer inhibiting agents include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-di-amine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetraacetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethyl ethylenediaminetriacetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP) and derivatives thereof, which can be used alone or in combination with any of the above. In embodiments in which at least one dye transfer inhibiting agent is used, a composition herein may comprise from about 0.0001% to about 10%, from about 0.01% to about 5%, or even from about 0.1% to about 3%, by weight of the composition.

A detergent composition herein can comprise silicates. In some of these embodiments, sodium silicates (e.g., sodium disilicate, sodium metasilicate, and/or crystalline phyllosilicates) find use. In some embodiments, silicates are present at a level of from about 1% to about 20% by weight of the composition. In some embodiments, silicates are present at a level of from about 5% to about 15% by weight of the composition.

A detergent composition herein can comprise dispersants. Suitable water-soluble organic materials include, but are not limited to the homo- or co-polymeric acids or their salts, in which the polycarboxylic acid comprises at least two carboxyl radicals separated from each other by not more than two carbon atoms.

A detergent composition herein may additionally comprise one or more enzymes as disclosed above, for example. In some aspects, a detergent composition can comprise one or more enzymes, each at a level from about 0.00001% to about 10% by weight of the composition and the balance of cleaning adjunct materials by weight of composition. In some other aspects, a detergent composition can also comprise each enzyme at a level of about 0.0001% to about 10%, about 0.001% to about 5%, about 0.001% to about 2%, or about 0.005% to about 0.5%, by weight of the composition. Enzymes comprised in a detergent composition herein may be stabilized using conventional stabilizing agents, e.g., a polyol such as propylene glycol or glycerol; a sugar or sugar alcohol; lactic acid; boric acid or a boric acid derivative (e.g., an aromatic borate ester).

A detergent composition in some aspects may comprise one or more other types of polymer in addition to insoluble alpha-glucan particles as disclosed herein. Examples of other types of polymers useful herein include carboxymethyl cellulose (CMC), dextran, poly(vinylpyrrolidone) (PVP), polyethylene glycol (PEG), poly(vinyl alcohol) (PVA), polycarboxylates such as polyacrylates, maleic/acrylic acid copolymers and lauryl methacrylate/acrylic acid copolymers.

A detergent composition herein may contain a bleaching system. For example, a bleaching system can comprise an $H_2O_2$ source such as perborate or percarbonate, which may be combined with a peracid-forming bleach activator such as tetraacetylethylenediamine (TAED) or nonanoyloxybenzenesulfonate (NOBS). Alternatively, a bleaching system may comprise peroxyacids (e.g., amide, imide, or sulfone type peroxyacids). Alternatively still, a bleaching system can be an enzymatic bleaching system comprising perhydrolase, for example, such as the system described in WO2005/056783.

A detergent composition herein may also contain conventional detergent ingredients such as fabric conditioners, clays, foam boosters, suds suppressors, anti-corrosion agents, soil-suspending agents, anti-soil redeposition agents, dyes, bactericides, tarnish inhibiters, optical brighteners, or perfumes. The pH of a detergent composition herein (measured in aqueous solution at use concentration) is usually neutral or alkaline (e.g., pH of about 7.0 to about 11.0).

It is believed that insoluble alpha-glucan particles herein can be included as an anti-redeposition agent and/or clay soil removal agent in a detergent composition such as a fabric care composition, if desired (such agents can optionally be characterized as whiteness maintenance agents in certain aspects). Examples of other suitable anti-redeposition and/or clay soil removal agents herein include polyethoxy zwitterionic surfactants, water-soluble copolymers of acrylic or methacrylic acid with acrylic or methacrylic acid-ethylene oxide condensates (e.g., U.S. Pat. No. 3,719,647), cellulose derivatives such as carboxymethylcellulose and hydroxypropylcellulose (e.g., U.S. Pat. Nos. 3,597,416 and 3,523, 088), and mixtures comprising nonionic alkyl polyethoxy surfactant, polyethoxy alkyl quaternary cationic surfactant and fatty amide surfactant (e.g., U.S. Pat. No. 4,228,044). Non-limiting examples of other suitable anti-redeposition and clay soil removal agents are disclosed in U.S. Pat. Nos. 4,597,898 and 4,891,160, and International Patent Appl. Publ. No. WO95/32272, all of which are incorporated herein by reference.

Particular forms of detergent compositions that can be adapted for purposes disclosed herein are disclosed in, for example, US20090209445A1, US20100081598A1, U.S. Pat. No. 7,001,878B2, EP1504994B1, WO2001085888A2, WO2003089562A1, WO2009098659A1, WO2009098660A1, WO2009112992A1, WO2009124160A1, WO2009152031A1, WO2010059483A1, WO2010088112A1, WO2010090915A1, WO2010135238A1, WO2011094687A1, WO2011094690A1, WO2011127102A1, WO2011163428A1, WO2008000567A1, WO2006045391A1, WO200600791 A1, WO2012027404A1, EP1740690B1, WO2012059336A1, U.S. Pat. No. 6,730,646B1, WO2008087426A1, WO2010116139A1, and WO2012104613A1, all of which are incorporated herein by reference.

Laundry detergent compositions herein can optionally be heavy duty (all purpose) laundry detergent compositions. Exemplary heavy duty laundry detergent compositions comprise a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof), and optionally non-ionic surfactant (selected from a group of linear or branched or random chain, substituted or unsubstituted alkyl alkoxylated alcohol, e.g., C8-C18 alkyl ethoxylated alcohols and/or C6-C12 alkyl phenol alkoxylates), where the weight ratio of anionic detersive surfactant (with a hydrophilic index (Hic) of from 6.0 to 9) to non-ionic detersive surfactant is greater than 1:1. Suitable detersive surfactants also include cationic detersive surfactants (selected from a group of alkyl pyridinium compounds, alkyl quaternary ammonium compounds, alkyl quaternary phosphonium compounds, alkyl ternary sulphonium compounds, and/or mixtures thereof); zwitterionic and/or amphoteric detersive surfactants (selected from a group of alkanolamine sulpho-betaines); ampholytic surfactants; semi-polar non-ionic surfactants and mixtures thereof.

A detergent herein such as a heavy duty laundry detergent composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated C1-C6 carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: C4-C25 alkyl group, polypropylene, polybutylene, vinyl ester of a saturated C1-C6 mono-carboxylic acid, C1-C6 alkyl ester of acrylic or methacrylic acid, and mixtures thereof.

A detergent herein such as a heavy duty laundry detergent composition may optionally include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example REPEL-O-TEX SF, SF-2 AND SRP6, TEXCARE SRA100, SRA300, SRN100, SRN170, SRN240, SRN300 AND SRN325, MARLOQUEST SL), anti-redeposition agent(s) herein (0.1 wt % to 10 wt %), include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); and polymeric carboxylate (such as maleate/acrylate random copolymer or polyacrylate homopolymer).

A detergent herein such as a heavy duty laundry detergent composition may optionally further include saturated or unsaturated fatty acids, preferably saturated or unsaturated C12-C24 fatty acids (0 wt % to 10 wt %); deposition aids (examples for which include polysaccharides, cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic starch, cationic polyacrylamides, and mixtures thereof.

A detergent herein such as a heavy duty laundry detergent composition may optionally further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N-disuccinic acid (EDDS), methyl glycine diacetic acid (MGDA), diethylene triamine penta acetic acid (DTPA), propylene diamine tetraacetic acid (PDTA), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetriacetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

A detergent herein such as a heavy duty laundry detergent composition may optionally include silicone or fatty-acid based suds suppressors; hueing dyes, calcium and magnesium cations, visual signaling ingredients, anti-foam (0.001 wt % to about 4.0 wt %), and/or a structurant/thickener (0.01 wt % to 5 wt %) selected from the group consisting of diglycerides and triglycerides, ethylene glycol distearate, microcrystalline cellulose, microfiber cellulose, biopolymers, xanthan gum, gellan gum, and mixtures thereof). Such structurant/thickener would be, in some aspects, in addition to the insoluble alpha-glucan particles comprised in the detergent. A structurant can also be referred to as a structural agent.

A detergent herein can be in the form of a heavy duty dry/solid laundry detergent composition, for example. Such a detergent may include: (i) a detersive surfactant, such as any anionic detersive surfactant disclosed herein, any non-ionic detersive surfactant disclosed herein, any cationic detersive surfactant disclosed herein, any zwitterionic and/or amphoteric detersive surfactant disclosed herein, any ampholytic surfactant, any semi-polar non-ionic surfactant, and mixtures thereof; (ii) a builder, such as any phosphate-free builder (e.g., zeolite builders in the range of 0 wt % to less than 10 wt %), any phosphate builder (e.g., sodium tri-polyphosphate in the range of 0 wt % to less than 10 wt %), citric acid, citrate salts and nitrilotriacetic acid, any silicate salt (e.g., sodium or potassium silicate or sodium meta-silicate in the range of 0 wt % to less than 10 wt %); any carbonate salt (e.g., sodium carbonate and/or sodium bicarbonate in the range of 0 wt % to less than 80 wt %), and mixtures thereof; (iii) a bleaching agent, such as any photobleach (e.g., sulfonated zinc phthalocyanines, sulfonated aluminum phthalocyanines, xanthenes dyes, and mixtures thereof), any hydrophobic or hydrophilic bleach activator (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, nonanoyloxybenzene sulfonate-NOBS, nitrile quats, and mixtures thereof), any source of hydrogen peroxide (e.g., inorganic perhydrate salts, examples of which include mono or tetra hydrate sodium salt of perborate, percarbonate, persulfate, perphosphate, or persilicate), any preformed hydrophilic and/or hydrophobic peracids (e.g., percarboxylic acids and salts, percarbonic acids and salts, perimidic acids and salts, peroxymonosulfuric acids and salts, and mixtures thereof); and/or (iv) any other components such as a bleach catalyst (e.g., imine bleach boosters examples of which include iminium cations and polyions, iminium zwitterions, modified amines, modified amine oxides, N-sulphonyl imines, N-phosphonyl imines, N-acyl imines, thiadiazole dioxides, perfluoroimines, cyclic sugar ketones, and mixtures thereof), and a metal-containing bleach catalyst (e.g., copper, iron, titanium, ruthenium, tungsten, molybdenum, or manganese cations along with an auxiliary metal cations such as zinc or aluminum and a sequestrate such as EDTA, ethylenediaminetetra(methylenephosphonic acid).

A detergent herein such as that for fabric care (e.g., laundry) can be comprised in a unit dose (e.g., sachet or pouch), for example. A unit dose form can comprise a water-soluble outer film that completely envelopes a liquid or solid detergent composition. A unit dose can comprise a single compartment, or at least two, three, or more (multiple) compartments. Multiple compartments can be arranged in a superposed orientation or a side-by-side orientation. A unit dose herein is typically a closed structure of any form/shape suitable for holding and protecting its contents without allowing contents release prior to contact with water.

Compositions disclosed herein can be in the form of a dishwashing detergent composition, for example. Examples of dishwashing detergents include automatic dishwashing detergents (typically used in dishwasher machines) and hand-washing dish detergents. A dishwashing detergent composition can be in any dry or liquid/aqueous form as disclosed herein, for example. Components that may be included in certain embodiments of a dishwashing detergent composition include, for example, one or more of a phosphate; oxygen- or chlorine-based bleaching agent; non-ionic surfactant; alkaline salt (e.g., metasilicates, alkali metal hydroxides, sodium carbonate); any active enzyme disclosed herein; anti-corrosion agent (e.g., sodium silicate); anti-foaming agent; additives to slow down the removal of glaze and patterns from ceramics; perfume; anti-caking agent (in granular detergent); starch (in tablet-based detergents); gelling agent (in liquid/gel based detergents); and/or sand (powdered detergents).

Dishwashing detergents such as an automatic dishwasher detergent or liquid dishwashing detergent can comprise (i) a non-ionic surfactant, including any ethoxylated non-ionic surfactant, alcohol alkoxylated surfactant, epoxy-capped poly(oxyalkylated) alcohol, or amine oxide surfactant present in an amount from 0 to 10 wt %; (ii) a builder, in the range of about 5-60 wt %, including any phosphate builder (e.g., mono-phosphates, di-phosphates, tri-polyphosphates, other oligomeric-polyphosphates, sodium tripolyphosphate-STPP), any phosphate-free builder (e.g., amino acid-based compounds including methyl-glycine-diacetic acid [MGDA] and salts or derivatives thereof, glutamic-N,N-diacetic acid [GLDA] and salts or derivatives thereof, iminodisuccinic acid (IDS) and salts or derivatives thereof, carboxy methyl inulin and salts or derivatives thereof, nitrilotriacetic acid [NTA], diethylene triamine penta acetic acid [DTPA], B-alaninediacetic acid [B-ADA] and salts thereof), homopolymers and copolymers of poly-carboxylic acids and partially or completely neutralized salts thereof, monomeric polycarboxylic acids and hydroxycarboxylic acids and salts thereof in the range of 0.5 wt % to 50 wt %, or sulfonated/carboxylated polymers in the range of about 0.1 wt % to about 50 wt %; (iii) a drying aid in the range of about 0.1 wt % to about 10 wt % (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds thereof, particularly of the reactive cyclic carbonate and urea type); (iv) a silicate in the range from about 1 wt % to about 20 wt % (e.g., sodium or potassium silicates such as sodium disilicate, sodium meta-silicate and crystalline phyllosilicates); (v) an inorganic bleach (e.g., perhydrate salts such as perborate, percarbonate, perphosphate, persulfate and persilicate salts) and/or an organic bleach (e.g., organic peroxyacids such as diacyl- and tetraacylperoxides, especially diperoxydodecanedioic acid, diperoxytetradecanedioic acid, and diperoxyhexadecanedioic acid); (vi) a bleach activator (e.g., organic peracid precursors in the range from about 0.1 wt % to about 10 wt %) and/or bleach catalyst (e.g., manganese triazacyclononane and related complexes; Co, Cu, Mn, and Fe bispyridylamine and related complexes; and pentamine acetate cobalt(III) and related complexes); (vii) a metal care agent in the range from about 0.1 wt % to 5 wt % (e.g., benzatriazoles, metal salts and complexes, and/or silicates); and/or (viii) any active enzyme disclosed herein in the range from about 0.01 to 5.0 mg of active enzyme per gram of automatic dishwashing detergent composition, and an enzyme stabilizer component (e.g., oligosaccharides, polysaccharides, and inorganic divalent metal salts).

A detergent herein such as that for dish care can be comprised in a unit dose (e.g., sachet or pouch), for example, and can be as described above for a fabric care detergent, but rather comprise a suitable dish detergent composition.

Compositions disclosed herein can be in the form of an oral care composition, for example. Examples of oral care compositions include dentifrices, toothpaste, mouth wash, mouth rinse, chewing gum, and edible strips that provide some form of oral care (e.g., treatment or prevention of cavities [dental caries], gingivitis, plaque, tartar, and/or periodontal disease). An oral care composition can also be for treating an "oral surface", which encompasses any soft or hard surface within the oral cavity including surfaces of the tongue, hard and soft palate, buccal mucosa, gums and dental surfaces. A "dental surface" herein is a surface of a natural tooth or a hard surface of artificial dentition including a crown, cap, filling, bridge, denture, or dental implant, for example.

An oral care composition herein can comprise about 0.01-15.0 wt % (e.g., ~0.1-10 wt % or ~0.1-5.0 wt %, ~0.1-2.0 wt %) of insoluble alpha-glucan particles as disclosed herein, for example. Insoluble alpha-glucan particles comprised in an oral care composition can sometimes be provided therein as a thickening agent and/or dispersion agent, which may be useful to impart a desired consistency and/or mouth feel to the composition. One or more other thickening or dispersion agents can also be provided in an oral care composition herein, such as a carboxyvinyl polymer, carrageenan (e.g., L-carrageenan), natural gum (e.g., karaya, xanthan, gum arabic, tragacanth), colloidal magnesium aluminum silicate, or colloidal silica, for example.

An oral care composition herein may be a toothpaste or other dentifrice, for example. Such compositions, as well as any other oral care composition herein, can additionally comprise, without limitation, one or more of an anticaries agent, antimicrobial or antibacterial agent, anticalculus or tartar control agent, surfactant, abrasive, pH-modifying agent, foam modulator, humectant, flavorant, sweetener, pigment/colorant, whitening agent, and/or other suitable components. Examples of oral care compositions to which insoluble alpha-glucan particles can be added are disclosed in U.S. Patent Appl. Publ. Nos. 2006/0134025, 2002/0022006 and 2008/0057007, which are incorporated herein by reference.

An anticaries agent herein can be an orally acceptable source of fluoride ions. Suitable sources of fluoride ions include fluoride, monofluorophosphate and fluorosilicate salts as well as amine fluorides, including olaflur (N'-octadecyltrimethylendiamine-N,N,N'-tris(2-ethanol)-dihydrofluoride), for example. An anticaries agent can be present in an amount providing a total of about 100-20000 ppm, about 200-5000 ppm, or about 500-2500 ppm, fluoride ions to the composition, for example. In oral care compositions in which sodium fluoride is the sole source of fluoride ions, an amount of about 0.01-5.0 wt %, about 0.05-1.0 wt %, or about 0.1-0.5 wt %, sodium fluoride can be present in the composition, for example.

An antimicrobial or antibacterial agent suitable for use in an oral care composition herein includes, for example, phenolic compounds (e.g., 4-allylcatechol; p-hydroxybenzoic acid esters such as benzylparaben, butylparaben, ethylparaben, methylparaben and propylparaben; 2-benzylphenol; butylated hydroxyanisole; butylated hydroxytoluene; capsaicin; carvacrol; creosol; eugenol; guaiacol; halogenated bisphenolics such as hexachlorophene and bromochlorophene; 4-hexylresorcinol; 8-hydroxyquinoline and salts thereof; salicylic acid esters such as menthyl salicylate, methyl salicylate and phenyl salicylate; phenol; pyrocatechol; salicylanilide; thymol; halogenated diphenylether compounds such as triclosan and triclosan monophosphate), copper (II) compounds (e.g., copper (II) chloride, fluoride, sulfate and hydroxide), zinc ion sources (e.g., zinc acetate, citrate, gluconate, glycinate, oxide, and sulfate), phthalic acid and salts thereof (e.g., magnesium monopotassium phthalate), hexetidine, octenidine, sanguinarine, benzalkonium chloride, domiphen bromide, alkylpyridinium chlorides (e.g. cetylpyridinium chloride, tetradecylpyridinium chloride, N-tetradecyl-4-ethylpyridinium chloride), iodine, sulfonamides, bisbiguanides (e.g., alexidine, chlorhexidine, chlorhexidine digluconate), piperidino derivatives (e.g., delmopinol, octapinol), magnolia extract, grapeseed extract, rosemary extract, menthol, geraniol, citral, eucalyptol, antibiotics (e.g., augmentin, amoxicillin, tetracycline, doxycycline, minocycline, metronidazole, neomycin, kanamycin, clindamycin), and/or any antibacterial agents disclosed in U.S. Pat. No. 5,776,435, which is incorporated herein by reference. One or more antimicrobial agents can optionally be present at about 0.01-10 wt % (e.g., 0.1-3 wt %), for example, in the disclosed oral care composition.

An anticalculus or tartar control agent suitable for use in an oral care composition herein includes, for example, phosphates and polyphosphates (e.g., pyrophosphates), polyaminopropanesulfonic acid (AMPS), zinc citrate trihydrate, polypeptides (e.g., polyaspartic and polyglutamic acids), polyolefin sulfonates, polyolefin phosphates, diphosphonates (e.g.,azacycloalkane-2,2-diphosphonates such as azacycloheptane-2,2-diphosphonic acid), N-methyl azacyclopentane-2,3-diphosphonic acid, ethane-1-hydroxy-1,1-diphosphonic acid (EHDP), ethane-1-amino-1,1-diphosphonate, and/or phosphonoalkane carboxylic acids and salts thereof (e.g., their alkali metal and ammonium salts). Useful inorganic phosphate and polyphosphate salts include, for example, monobasic, dibasic and tribasic sodium phosphates, sodium tripolyphosphate, tetrapolyphosphate, mono-, di-, tri- and tetra-sodium pyrophosphates, disodium dihydrogen pyrophosphate, sodium trimetaphosphate, sodium hexametaphosphate, or any of these in which sodium is replaced by potassium or ammonium. Other useful anticalculus agents in certain embodiments include anionic polycarboxylate polymers (e.g., polymers or copolymers of acrylic acid, methacrylic, and maleic anhydride such as polyvinyl methyl ether/maleic anhydride copolymers). Still other useful anticalculus agents include sequestering agents such as hydroxycarboxylic acids (e.g., citric, fumaric, malic, glutaric and oxalic acids and salts thereof) and aminopolycarboxylic acids (e.g., EDTA). One or more anticalculus or tartar control agents can optionally be present at about 0.01-50 wt % (e.g., about 0.05-25 wt % or about 0.1-15 wt %), for example, in the disclosed oral care composition.

A surfactant suitable for use in an oral care composition herein may be anionic, non-ionic, or amphoteric, for example. Suitable anionic surfactants include, without limitation, water-soluble salts of $C_{8-20}$ alkyl sulfates, sulfonated monoglycerides of $C_{8-20}$ fatty acids, sarcosinates, and taurates. Examples of anionic surfactants include sodium lauryl sulfate, sodium coconut monoglyceride sulfonate, sodium lauryl sarcosinate, sodium lauryl isoethionate, sodium laureth carboxylate and sodium dodecyl benzenesulfonate.

Suitable non-ionic surfactants include, without limitation, poloxamers, polyoxyethylene sorbitan esters, fatty alcohol ethoxylates, alkylphenol ethoxylates, tertiary amine oxides, tertiary phosphine oxides, and dialkyl sulfoxides. Suitable amphoteric surfactants include, without limitation, derivatives of $C_{8-20}$ aliphatic secondary and tertiary amines having an anionic group such as a carboxylate, sulfate, sulfonate, phosphate or phosphonate. An example of a suitable amphoteric surfactant is cocoamidopropyl betaine. One or more surfactants are optionally present in a total amount of about 0.01-10 wt % (e.g., about 0.05-5.0 wt % or about 0.1-2.0 wt %), for example, in the disclosed oral care composition.

An abrasive suitable for use in an oral care composition herein may include, for example, silica (e.g., silica gel, hydrated silica, precipitated silica), alumina, insoluble phosphates, calcium carbonate, and resinous abrasives (e.g., a urea-formaldehyde condensation product). Examples of insoluble phosphates useful as abrasives herein are orthophosphates, polymetaphosphates and pyrophosphates, and include dicalcium orthophosphate dihydrate, calcium pyrophosphate, beta-calcium pyrophosphate, tricalcium phosphate, calcium polymetaphosphate and insoluble sodium polymetaphosphate. One or more abrasives are optionally present in a total amount of about 5-70 wt % (e.g., about 10-56 wt % or about 15-30 wt %), for example, in the disclosed oral care composition. The average particle size of an abrasive in certain embodiments is about 0.1-30 microns (e.g., about 1-20 microns or about 5-15 microns).

An oral care composition in certain embodiments may comprise at least one pH-modifying agent. Such agents may be selected to acidify, make more basic, or buffer the pH of a composition to a pH range of about 2-10 (e.g., pH ranging from about 2-8, 3-9, 4-8, 5-7, 6-10, or 7-9). Examples of pH-modifying agents useful herein include, without limitation, carboxylic, phosphoric and sulfonic acids; acid salts (e.g., monosodium citrate, disodium citrate, monosodium malate); alkali metal hydroxides (e.g. sodium hydroxide, carbonates such as sodium carbonate, bicarbonates, sesquicarbonates); borates; silicates; phosphates (e.g., monosodium phosphate, trisodium phosphate, pyrophosphate salts); and imidazole.

A foam modulator suitable for use in an oral care composition herein may be a polyethylene glycol (PEG), for example. High molecular weight PEGs are suitable, including those having an average molecular weight of about 200000-7000000 (e.g., about 500000-5000000 or about 1000000-2500000), for example. One or more PEGs are optionally present in a total amount of about 0.1-10 wt % (e.g. about 0.2-5.0 wt % or about 0.25-2.0 wt %), for example, in the disclosed oral care composition.

An oral care composition in certain embodiments may comprise at least one humectant. A humectant in certain embodiments may be a polyhydric alcohol such as glycerin, sorbitol, xylitol, or a low molecular weight PEG. Most suitable humectants also may function as a sweetener herein. One or more humectants are optionally present in a total amount of about 1.0-70 wt % (e.g., about 1.0-50 wt %, about 2-25 wt %, or about 5-15 wt %), for example, in the disclosed oral care composition.

A natural or artificial sweetener may optionally be comprised in an oral care composition herein. Examples of suitable sweeteners include dextrose, sucrose, maltose, dextrin, invert sugar, mannose, xylose, ribose, fructose, levulose, galactose, corn syrup (e.g., high fructose corn syrup or corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, and cyclamates. One or more sweeteners are optionally present in a total amount of about 0.005-5.0 wt %, for example, in the disclosed oral care composition.

A natural or artificial flavorant may optionally be comprised in an oral care composition herein. Examples of suitable flavorants include vanillin; sage; marjoram; parsley oil; spearmint oil; cinnamon oil; oil of wintergreen (methylsalicylate); peppermint oil; clove oil; bay oil; anise oil; eucalyptus oil; citrus oils; fruit oils; essences such as those derived from lemon, orange, lime, grapefruit, apricot, banana, grape, apple, strawberry, cherry, or pineapple; bean- and nut-derived flavors such as coffee, cocoa, cola, peanut, or almond; and adsorbed and encapsulated flavorants. Also encompassed within flavorants herein are ingredients that provide fragrance and/or other sensory effect in the mouth, including cooling or warming effects. Such ingredients include, without limitation, menthol, menthyl acetate, menthyl lactate, camphor, eucalyptus oil, eucalyptol, anethole, eugenol, cassia, oxanone, Irisone©, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), and menthone glycerol acetal (MGA). One or more flavorants are optionally present in a total amount of about 0.01-5.0 wt % (e.g., about 0.1-2.5 wt %), for example, in the disclosed oral care composition.

An oral care composition in certain embodiments may comprise at least one bicarbonate salt. Any orally acceptable bicarbonate can be used, including alkali metal bicarbonates such as sodium or potassium bicarbonate, and ammonium bicarbonate, for example. One or more bicarbonate salts are optionally present in a total amount of about 0.1-50 wt % (e.g., about 1-20 wt %), for example, in the disclosed oral care composition.

An oral care composition in certain embodiments may comprise at least one whitening agent and/or colorant. A suitable whitening agent is a peroxide compound such as any of those disclosed in U.S. Pat. No. 8,540,971, which is incorporated herein by reference. Suitable colorants herein include pigments, dyes, lakes and agents imparting a particular luster or reflectivity such as pearling agents, for example. Specific examples of colorants useful herein include talc; mica; magnesium carbonate; calcium carbonate; magnesium silicate; magnesium aluminum silicate; silica; titanium dioxide; zinc oxide; red, yellow, brown and black iron oxides; ferric ammonium ferrocyanide; manganese violet; ultramarine; titaniated mica; and bismuth oxychloride. One or more colorants are optionally present in a total amount of about 0.001-20 wt % (e.g., about 0.01-10 wt % or about 0.1-5.0 wt %), for example, in the disclosed oral care composition.

Additional components that can optionally be included in an oral composition herein include one or more enzymes (above), vitamins, and anti-adhesion agents, for example. Examples of vitamins useful herein include vitamin C, vitamin E, vitamin B5, and folic acid. Examples of suitable anti-adhesion agents include solbrol, ficin, and quorum-sensing inhibitors.

The present disclosure also concerns a method of treating a material. This method comprises contacting a material with an aqueous composition comprising insoluble alpha-glucan particles as disclosed herein.

A material contacted with an aqueous composition in a contacting method herein can comprise a fabric in some aspects. A fabric herein can comprise natural fibers, synthetic fibers, semi-synthetic fibers, or any combination thereof. A semi-synthetic fiber herein is produced using naturally occurring material that has been chemically derivatized, an example of which is rayon. Non-limiting examples of fabric types herein include fabrics made of (i) cellulosic fibers such as cotton (e.g., broadcloth, canvas, chambray, chenille, chintz, corduroy, cretonne, damask, denim, flannel, gingham, jacquard, knit, matelassé, oxford, percale, poplin, plissé, sateen, seersucker, sheers, terry cloth, twill, velvet), rayon (e.g., viscose, modal, lyocell), linen, and Tencel®; (ii) proteinaceous fibers such as silk, wool and related mammalian fibers; (iii) synthetic fibers such as polyester, acrylic, nylon, and the like; (iv) long vegetable fibers from jute, flax, ramie, coir, kapok, sisal, henequen, abaca, hemp and sunn; and (v) any combination of a fabric of (i)-(iv). Fabric comprising a combination of fiber types (e.g., natural and synthetic) include those with both a cotton fiber and polyester, for example. Materials/articles containing one or more fabrics herein include, for example, clothing, curtains, drapes, upholstery, carpeting, bed linens, bath linens, tablecloths, sleeping bags, tents, car interiors, etc. Other materials comprising natural and/or synthetic fibers include, for example, non-woven fabrics, paddings, paper, and foams.

An aqueous composition that is contacted with a fabric can be, for example, a fabric care composition (e.g., laundry detergent, fabric softener). Thus, a treatment method in certain embodiments can be considered a fabric care method or laundry method if employing a fabric care composition therein. A fabric care composition herein is contemplated to effect one or more of the following fabric care benefits (i.e., surface substantive effects): wrinkle removal, wrinkle reduction, wrinkle resistance, fabric wear reduction, fabric wear resistance, fabric pilling reduction, extended fabric life, fabric color maintenance, fabric color fading reduction, reduced dye transfer, fabric color restoration, fabric soiling reduction, fabric soil release, fabric shape retention, fabric smoothness enhancement, anti-redeposition of soil on fabric, anti-greying of laundry, improved fabric hand/handle, and/or fabric shrinkage reduction.

Examples of conditions (e.g., time, temperature, wash/rinse volumes) for conducting a fabric care method or laundry method herein are disclosed in WO1997/003161 and U.S. Pat. Nos. 4,794,661, 4,580,421 and 5,945,394, which are incorporated herein by reference. In other examples, a material comprising fabric can be contacted with an aqueous composition herein: (i) for at least about 5, 10, 20, 30, 40, 50, 60, 70, 80, 90, 100, 110, or 120 minutes; (ii) at a temperature of at least about 10, 15, 20, 25, 30, 35, 40, 45, 50, 55, 60, 65, 70, 75, 80, 85, 90, or 95° C. (e.g., for laundry wash or rinse: a "cold" temperature of about 15-30° C., a "warm" temperature of about 30-50° C., a "hot" temperature of about 50-95° C.); (iii) at a pH of about 2, 3, 4, 5, 6, 7, 8, 9, 10, 11, or 12 (e.g., pH range of about 2-12, or about 3-11); (iv) at a salt (e.g., NaCl) concentration of at least about 0.5, 1.0, 1.5, 2.0, 2.5, 3.0, 3.5, or 4.0 wt %; or any combination of (i)-(iv).

The contacting step in a fabric care method or laundry method can comprise any of washing, soaking, and/or rinsing steps, for example. Contacting a material or fabric in still further embodiments can be performed by any means known in the art, such as dissolving, mixing, shaking, spraying, treating, immersing, flushing, pouring on or in, combining, painting, coating, applying, affixing to, and/or communicating an effective amount of insoluble alpha-glucan particles herein with the fabric or material. In still further embodiments, contacting may be used to treat a fabric to provide a surface substantive effect. As used herein, the term "fabric hand" or "handle" refers to a person's tactile sensory response towards fabric which may be physical, physiological, psychological, social or any combination thereof. In one embodiment, the fabric hand may be measured using a PhabrOmeter® System for measuring relative hand value (available from Nu Cybertek, Inc. Davis, CA) (American Association of Textile Chemists and Colorists [AATCC test method "202-2012, Relative Hand Value of Textiles: Instrumental Method"]).

In some aspects of treating a material comprising fabric, insoluble alpha-glucan particle components of the aqueous composition adsorb to the fabric. This feature is believed to render insoluble alpha-glucan particles herein useful as anti-redeposition agents and/or anti-greying agents in fabric care compositions disclosed (in addition to their viscosity-modifying effect). An anti-redeposition agent or anti-greying agent herein helps keep soil from redepositing onto clothing in wash water after the soil has been removed. It is further contemplated that adsorption of insoluble alpha-glucan particles herein to a fabric enhances mechanical properties of the fabric.

Adsorption of insoluble alpha-glucan particles to a fabric herein can be measured using a colorimetric technique (e.g., Dubois et al., 1956, *Anal. Chem.* 28:350-356; Zemljic et al., 2006, *Lenzinger Berichte* 85:68-76; both incorporated herein by reference), for example, or any other method known in the art.

Other materials that can be contacted in the above treatment method include surfaces that can be treated with a dish detergent (e.g., automatic dishwashing detergent or hand dish detergent). Examples of such materials include surfaces of dishes, glasses, pots, pans, baking dishes, utensils and flatware made from ceramic material, china, metal, glass, plastic (e.g., polyethylene, polypropylene, polystyrene, etc.) and wood (collectively referred to herein as "tableware"). Thus, the treatment method in certain embodiments can be considered a dishwashing method or tableware washing method, for example. Examples of conditions (e.g., time, temperature, wash volume) for conducting a dishwashing or tableware washing method herein are disclosed in U.S. Pat. No. 8,575,083, which is incorporated herein by reference. In other examples, a tableware article can be contacted with an aqueous composition herein under a suitable set of conditions such as any of those disclosed above with regard to contacting a fabric-comprising material.

Other materials that can be contacted in the above treatment method include oral surfaces such as any soft or hard surface within the oral cavity including surfaces of the tongue, hard and soft palate, buccal mucosa, gums and dental surfaces (e.g., natural tooth or a hard surface of artificial dentition such as a crown, cap, filling, bridge, denture, or dental implant). Thus, a treatment method in certain embodiments can be considered an oral care method or dental care method, for example. Conditions (e.g., time, temperature) for contacting an oral surface with an aqueous composition herein should be suitable for the intended purpose of making such contact. Other surfaces that can be contacted in a treatment method also include a surface of the integumentary system such as skin, hair or nails.

Thus, certain embodiments of the present disclosure concern material (e.g., fabric) that comprises insoluble alpha-glucan particles herein. Such material can be produced following a material treatment method as disclosed herein, for example. A material may comprise insoluble alpha-glucan particles in some aspects if the compound is adsorbed to, or otherwise in contact with, the surface of the material.

Some aspects of a method of treating a material herein further comprise a drying step, in which a material is dried after being contacted with the aqueous composition. A drying step can be performed directly after the contacting step, or following one or more additional steps that might follow the contacting step (e.g., drying of a fabric after being rinsed, in water for example, following a wash in an aqueous composition herein). Drying can be performed by any of several means known in the art, such as air drying (e.g., ~20-25° C.), or at a temperature of at least about 30, 40, 50, 60, 70, 80, 90, 100, 120, 140, 160, 170, 175, 180, or 200° C., for example. A material that has been dried herein typically has less than 3, 2, 1, 0.5, or 0.1 wt % water comprised therein. Fabric is a preferred material for conducting an optional drying step.

An aqueous composition used in a treatment method herein can be any aqueous composition disclosed herein. Examples of aqueous compositions include detergents (e.g., laundry detergent or dish detergent), fabric softeners, and water-containing dentifrices such as toothpaste.

In some aspects, a material that can be treated with an liquid composition comprising insoluble alpha-glucan particles herein is a non-woven product. This treatment, which can involve application of an aqueous or non-aqueous composition (e.g., dispersion) comprising insoluble alpha-glucan particles herein (at any concentration as disclosed herein) typically followed by a drying step (e.g., air drying, heated drying, vacuum drying; drying temperature can be any suitable temperature disclosed herein, for example), can strengthen (i.e., act as a binder for) a non-woven product. In some aspects, insoluble alpha-glucan particles can increase the dry or wet tensile strength (measured in N/5 cm) of a non-woven by about, or at least about, 1000%, 10000%, 100000%, or 1000000%, for example. Thus, further provided herein are non-woven products containing a binder/strengthening agent that comprises insoluble alpha-glucan particles herein. Optionally, such insoluble alpha-glucan particles can be crosslinked; any crosslinking agent and/or procedure disclosed herein can be used (e.g., glyoxal, citric acid, PAE) to prepare crosslinked glucan particles before applying them to the non-woven product. In some aspects, the dry or wet tensile strength of a non-woven comprising an alpha-glucan binder herein can be about, or at least about, 10, 15, 20, 25, 50, 75, 100, 125, 130, 135, 140, 145, 150, 10-150, 15-150, 20-150, 25-150, 10-140, 15-140, 20-140, or 25-140 N/5 cm. On a basis of the total weight of non-woven material and alpha-glucan binder in a non-woven product, the content of the alpha-glucan therein can be about 5, 10, 15, 20, 25, 5-25, 5-20, 10-25, or 10-20 wt %. In aspects in which a crosslinker is used, such can be about 1, 2, 3, 4, 5, 6, 2-6, 2-5, 3-6, or 3-5 wt % of the total weight of a non-woven product. A non-woven product herein can be, for example, air-laid, dry-laid, wet-laid, carded, electrospun, spun-lace, spun-bind, or melt-blown. In some aspects, a non-woven product can be an abrasive or scouring sheet, agricultural covering, agricultural seed strip, apparel lining, automobile headliner or upholstery, bib, cheese wrap, civil engineering fabric, coffee filter, cosmetic remover or applicator, detergent pouch/sachet, fabric softener sheet, envelope, face mask, filter, garment bag, heat or electricity conductive fabric, household care wipe (e.g., for floor care, hard surface cleaning, pet care etc.), house wrap, hygiene product (e.g., sanitary pad/napkin, under-pad), insulation, label, laundry aid, medical care or personal injury care product (e.g., bandage, cast padding or cover, dressing, pack, sterile overwrap, sterile packaging, surgical drape, surgical gown, swab), mop, napkin or paper towel, paper, personal wipe or baby wipe, reusable bag, roofing undercovering, table linen, tag, tea or coffee bag, upholstery, vacuum cleaning bag, or wallcovering. The fiber of a non-woven product can comprise cellulose and/or alpha-1,3-glucan in some aspects, or can comprise one or more other materials disclosed herein that can be used to form a fiber. Examples of non-woven products herein, non-woven product materials, and/or methods of production of non-woven products and materials, can be as disclosed in Int. Pat. Appl. Publ. No. WO2019055397 or U.S. Pat. Appl. Publ. Nos. 2018/0282918, 2017/0167063, 2018/0320291, or 2010/0291213, which are each incorporated herein by reference.

A composition comprising insoluble alpha-glucan particles herein can be a film or coating, for example. A film or coating can be a dried film or coating in some aspects, comprising less than about 3, 2, 1, 0.5, or 0.1 wt % water, for example. In some aspects, a film or coating can comprise about 20-40, 20-35, 20-30, 25-40, 25-35, or 25-30 wt % insoluble alpha-glucan particles, where the balance of material optionally is water, an aqueous solution, and/or a plasticizer. The amount of insoluble alpha-glucan particles comprised in a film or coating herein can be about, or at least about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, or 99.9 wt %, for example.

A film or coating herein can have a thickness of about, at least about, or up to about, 0.5, 0.6, 0.7, 0.8, 0.9, 1.0, 1.1, 1.2, 1.3, 1.4, 1.5, 2, 2.5, 5, 7.5, 10, 15.5, 15, 17.5, 20, 22.5, 25, 30, 35, 40, 45, 50, 75, 100, 150, 200, 0.5-1.5, 0.8-1.5, 1.0-1.5, 0.5-1.4, 0.8-1.4, or 1.0-1.4 mil (1 mil=0.001 inch), for instance. In some aspects, such thickness is uniform, which can be characterized by having a contiguous area that (i) is at least 20%, 30%, 40%, or 50% of the total film/coating area, and (ii) has a standard deviation of thickness of less than about 0.06, 0.05, or 0.04 mil. A film or coating herein can be characterized as thin (e.g., <2 mil) in some aspects. A film herein is typically a cast film.

A film or coating herein can exhibit various degrees of transparency as desired. For example, a film/coating can be highly transparent (e.g., high light transmission, and/or low haze). Optical transparency as used herein can, for example, refer to a film or coating allowing at least about 10-99% light transmission, or at least about 50%, 60%, 70%, 80%, 90%, 95%, 96%, 97%, 98%, or 99% light transmission, and/or less than 30%, 25%, 20%, 15%, 10%, 5%, 2.5%, 2%, or 1% haze. High optical transparency can optionally refer to a film/coating having at least about 90% light transmittance and/or a haziness of less than 10%. Light transmittance of a film/coating herein can be measured following test ASTM D1746 (2009, *Standard Test Method for Transparency of Plastic Sheeting*, ASTM International, West Conshohocken, PA), for example, which is incorporated herein by reference. Haze of a film/coating herein can be measured following test ASTM D1003-13 (2013, *Standard Test Method for Haze and Luminous Transmittance of Transparent Plastics*, ASTM International, West Conshohocken, PA), for example, which is incorporated herein by reference. It is notable, for example, that a film/coating herein with about 20-40, 20-35, 20-30, 25-40, 25-35, or 25-30 wt % insoluble alpha-glucan particles (e.g., balance is water or aqueous solution) has high optical transparency (e.g., >90% light transparency and/or less than 10% haze), whereas a film/coating with an otherwise same amount of insoluble alpha-glucan (e.g., non-hydrolyzed) of DPw>200 (e.g., DPw≥~700 or ~800), crystallinity <0.65 (e.g., ≤0.60), and/or D50 diameter of 5-50 microns typically does not exhibit this beneficial feature (e.g., latter type of film/coating can be hazy).

A film or coating herein can optionally further comprise a plasticizer such as glycerol, propylene glycol, ethylene glycol, and/or polyethylene glycol. In some aspects, other film components (in addition to insoluble alpha-glucan particles herein) can be as disclosed in U.S. Patent. Appl. Publ. No. 2011/0151224, 2015/0191550, or 20190153674, U.S. Pat. No. 9,688,035 or 3,345,200, or International Patent Appl. Publ. No. WO2018/200437, all of which are incorporated herein by reference.

A film or coating, or any suitable solid composition herein (e.g., composite), in some aspects can further comprise at least one crosslinking agent. Insoluble alpha-glucan particles in the composition can be crosslinked (covalently) to each other and/or to at least one other component (e.g., polymer, active agent) of the composition, or to a component of a substrate if the composition is applied to the substrate. Yet, in some aspects, insoluble alpha-glucan particles are not crosslinked in any manner, but one or more other components of the composition are crosslinked. Crosslinking can (i) enhance the tensile strength of, and/or (ii) plasticize, film or coating compositions, for example. Crosslinking can link a film or coating to a substrate in some aspects. In some cases, a crosslinking agent such as a di- or poly-carboxylic acid, aldehyde, or polyphenol can be used to impart both plasticity and linking-to-substrate features. Suitable crosslinking agents for preparing a composition herein with crosslinking as above include are contemplated to include phosphoryl chloride ($POCl_3$), polyphosphate, sodium trimetaphosphate (STMP), boron-containing compounds (e.g., boric acid, diborates, tetraborates such as tetraborate decahydrate, pentaborates, polymeric compounds such as Polybor®, alkali borates), polyvalent metals (e.g., titanium-containing compounds such as titanium ammonium lactate, titanium triethanolamine, titanium acetylacetonate, or polyhydroxy complexes of titanium; zirconium-containing compounds such as zirconium lactate, zirconium carbonate, zirconium acetylacetonate, zirconium triethanolamine, zirconium diisopropylamine lactate, or polyhydroxy complexes of zirconium), glyoxal, glutaraldehyde, aldehyde, polyphenol, divinyl sulfone, epichlorohydrin, polyamide-epichlorohydrin (PAE), di- or poly-carboxylic acids (e.g., citric acid, malic acid, tartaric acid, succinic acid, glutaric acid, adipic acid), dichloro acetic acid, polyamines, diethylene glycol dimethyl ether (diglyme), and ethylene glycol diglycidyl ether (EGDE). Still other examples of suitable crosslinking agents are described in U.S. Pat. Nos. 4,462,917, 4,464,270, 4,477,360 and 4,799,550, and U.S. Patent Appl. Publ. No. 2008/0112907, which are all incorporated herein by reference. Yet, in some aspects, a crosslinking agent is not a boron-containing compound (e.g., as described above). Insoluble alpha-glucan herein can be crosslinked, such as with any crosslinker as presently disclosed, in other contexts besides a film or coating (e.g., in a dispersion or other composition disclosed herein).

One or more conditioning agents can be comprised in a film of coating, for example, to enhance the haptics of the film or coating. A conditioning agent can be an anionic softener such as sulphated oil, soap, sulphated alcohol, and/or oil emulsion; a cationic softener such as a quaternary ammonium compound; a nonionic softener such as a polyoxyethylene derivative, polyethylene emulsion, wax emulsion, and/or silicon softener; natural fatty acid; oil; monoglyceride; diglyceride; polyglyceride; citric acid ester; lactic acid ester; and/or sugar ester such as a sucrose ester and/or sorbitan ester. Also disclosed are articles comprising an adhesive, film, coating, or binder comprising insoluble alpha-glucan particles herein in a dry form. Such articles (optionally, "coated articles") comprise a substrate having at least one surface on which is disposed/deposited the coating, adhesive, film, or binder, in a substantially continuous or discontinuous manner. In some aspects, an article comprises paper, leather, wood, metal, polymer, fibrous material, masonry, drywall, plaster, and/or an architectural surface. An "architectural surface" herein is an external or internal surface of a building or other man-made structure. In some aspects, an article comprises a porous substrate such as in paper, cardboard, paperboard, corrugated board, a cellulosic substrate, a textile, or leather. Yet, in some aspects, an article can comprise a polymer such as polyamide, polyolefin, polylactic acid, polyethylene terephthalate (PET), poly(trimethylene terephthalate) (PTT), aramid, polyethylene sulfide (PES), polyphenylene sulfide (PPS), polyimide (PI), polyethylene imine (PEI), polyethylene naphthalate (PEN), polysulfone (PS), polyether ether ketone (PEEK), polyethylene, polypropylene, poly(cyclic olefins), poly(cyclohexylene dimethylene terephthalate), poly(trimethylene furandicarboxylate) (PTF), or cellophane. In some aspects, an article comprising a fibrous substrate is a fiber, yarn, fabric, fabric blend, textile, non-woven, paper, or carpet. A fibrous substrate can contain natural and/or synthetic fibers, such as cotton, cellulose, wool, silk, rayon, nylon, aramid, acetate, polyurethane urea, acrylic, jute, sisal, sea grass, coir, polyamide, polyester, polyolefin, polyacrylonitrile, polypropylene, polyaramid, or blends thereof.

A film, coating, or other composition (e.g. composite) herein can have grease/oil and/or oxygen barrier properties in some aspects. Such a composition can comprise, along with insoluble alpha-glucan particles herein, one or more components as disclosed in U.S. Patent. Appl. Publ. No. 20190153674 or International Patent Appl. Publ. No. WO2018/200437, which are each incorporated herein by reference. For example, a film, coating, or other composition herein can comprise, optionally as a binder, one or more of polyvinyl alcohol, polyvinyl acetate, partially saponified polyvinyl acetate, silanol-modified polyvinyl alcohol, butenediol vinyl alcohol co-polymer (BVOH), polyurethane, starch, corn dextrin, carboxymethyl cellulose, cellulose ethers, hydroxyethyl cellulose, hydroxypropyl cellulose, ethyl hydroxyethyl cellulose, methyl cellulose, alginates, sodium alginate, xanthan, carrageenan, casein, soy protein, guar gums, synthetic polymers, styrene butadiene latex, and/or styrene acrylate latex. A composition for preparing a film, coating, or other composition in some aspects can comprise about 50, 55, 60, 65, 70, 75, 80, 85, 90, 95, 65-85, 65-80, 70-85, or 70-80 wt % of a binder or compound such as polyvinyl alcohol (or any other of the above-referenced compounds), and about 50, 45, 40, 35, 30, 25, 20, 15, 10, 5, 2.5, 15-35, 20-35, 15-30, or 20-30 wt % insoluble alpha-glucan particles as presently disclosed. In some aspects, a composition for preparing a film, coating, or other composition can comprise a ratio of binder or compound (e.g., any of the above-referenced compounds such as polyvinyl alcohol or starch) to insoluble alpha-glucan herein of about 7:3, 7.5:2.5, 8:2, 8.5:1.5, or 9:1, based on the wt % of each of these components in the composition. In some aspects, a film, coating, or other composition does not comprise starch, while in other aspects such as an oxygen barrier, starch can be included (e.g., as disclosed in U.S. Patent Appl. Publ. No. 2011/0135912 or U.S. Pat. No. 5,621,026 or 6,692,801, which are incorporated herein by reference). Grease/oil barrier properties of a coating or film composition herein can be evaluated using a standard "KIT" type test following Technical Association of the Pulp and Paper Industry (TAPPI) Test Method T-559 cm-02 (Grease resistance test for paper and paperboard, TAPPI Press, Atlanta, GA, USA; incorporated herein by reference), for example. Good grease/oil barrier/resistance function is indicated in this test by values closer to 12 on a scale of 1 to 12. Grease/oil barrier properties, as well as water/aqueous liquid barrier properties, can be evaluated by Cobb test as disclosed in Example 8, if desired. A barrier herein typically has a Cobb index value of less than 20, 17.5, 15, 12.5, 10, 7.5, or 5. The Cobb index value of a barrier with one or more of the above-referenced compounds and insoluble alpha-glucan herein can be about, or at least about, 10%, 20%, 30%, 40%, 50%, or 60% lower, for example, than the Cobb index value of the barrier that is otherwise the same but lacking the insoluble alpha-glucan. Oxygen barrier properties of a coating or film composition herein can be evaluated by measuring the oxygen transmission rate (OTR) of the coating; OTR can be determined, for example, according to ASTM F-1927-07 (2007, *Standard Test Method for Determination of Oxygen Gas Transmission Rate, Permeability and Permeance at Controlled Relative Humidity Through Barrier Materials Using a Coulometric Detector*, ASTM International, West Conshohocken, PA), which is incorporated herein by reference. OTR can be determined under relative humidity conditions of about 50%-80%, 30%-55%, 35%-50%, or 30%-80%, and/or a temperature of about, or at least about, 15, 20, 25, 30, 35, 40, 45, 15-40, 15-35, 15-30, 15-25, 20-40, 20-35, 20-30, or 20-25° C., for example. Examples of substrates herein that can take advantage of a grease/oil and/or oxygen barrier coating include any of the foregoing substrates/surfaces, including a substrate comprising cellulose (e.g., paper, paperboard, cardboard, corrugated board, textile), polyethylene, polypropylene, poly lactic acid, poly (ethylene terephthalate) (e.g., MYLAR), poly(trimethylene terephthalate), polyamide, polybutylene succinate, polybutylene adipate terephthalate, polybutylene succinate adipate, poly(trimethylene furandicarboxylate), a synthetic and/or petrol-based substrate, or a bio-based substrate. Grease/oil and/or oxygen barrier activity of a coated material herein can be increased by about, or at least about 5%, 10%, 15%, or 20%, for example, compared to the grease/oil and/or oxygen barrier activity of the material that (i) is uncoated or (ii) contains a coating that differs from the foregoing coating by lacking the insoluble alpha-glucan particles component. Any of the foregoing film, coating, or other compositions can be in the form of a laminate or extruded product, for example, and that is optionally situated on any of the foregoing substrates.

A film, coating, or other composition (e.g., dispersion, foam, masterbatch) comprising insoluble alpha-glucan particles herein can further comprise polyurethane (e.g., any as disclosed herein) in some aspects. Such a composition can comprise about 1, 5, 10, 15, 20, 35, 30, 35, 40, 45, 50, 55, 60, 5-60, 5-50, 5-45, 5-40, 5-35, 5-30, 10-60, 10-50, 10-45, 10-40, 10-35, or 10-30 wt % of insoluble alpha-glucan herein, for example; the balance can be comprised mostly of (e.g., be over 90% or 95% of) one or more polyurethanes. Such a composition can be wet (e.g., a dispersion of glucan and polyurethane), or dry (e.g., a masterbatch, film/coating, laminate, foam, or extruded composite of glucan and polyurethane). A polyurethane herein can be of a molecular weight that is about, or at least about, 1000, 1500, 2000, 2500, 3000, 3500, 4000, 1000-3000, 1500-3000, 1000-2500, or 1500-2500, for example. Such a composition can, in some instances, be hydrolytically aged (e.g., exposed to 45-55 or ~50° C., and/or 90-98% or ~95% relative humidity, for a period of 2-4 or 3 days). A polyurethane film, coating, or other composition herein can have, or be within plus/minus 5% or 10% of, any of the features/values (e.g., tensile stress at break, % elongation at break, tensile stress at 50% elongation, tensile stress at 300% elongation, area under the curve) listed in Tables 9 and 10 below (Example 10), for example. In some aspects, a polyurethane composition with insoluble alpha-1,3-glucan herein can be heat- and/or pressure-processable; application of heat and/or pressure for pressing, molding, extruding, or any other related processing step can be at about, or at least about, 90, 95, 100, 105, 110, 115, 120, 130, 140, 95-115, or 100-110° C., and/or at a pressure of at least about 5000, 10000, 15000, 20000, or 25000 psi, for example. Such application of heat and/or pressure can be for a time of at least about 1, 2, 3, 4, 5, 6, 7, 8, 9, 10, 15, or 30 minutes, for example. A pressed polyurethane composition in some aspects such as a film can be about, or at least about, 70%, 75%, 80%, 85%, 90%, 95%, 98%, 99%, or 100% transparent or translucent. In some aspects, any polyurethane composition presently disclosed can be made by a process that comprises providing an aqueous polyurethane dispersion, and mixing insoluble alpha-glucan particles herein with the polyurethane dispersion (e.g., by adding an aqueous dispersion of the glucan particles). The resulting aqueous dispersion can be used directly to make a composition (e.g., a film or coating), or it can be dried to a masterbatch that is then used to prepare a composition (e.g., by melt-processing).

A film or coating in some aspects can be in the form of an edible film or coating. Such a material can, in some aspects, comprise insoluble alpha-glucan particles herein and one or more components as described in U.S. Pat. Nos. 4,710,228, 4,543,370, 4,820,533, 4,981,707, 5,470,581, 5,997,918, 8,206,765, or 8,999,413, or U.S. Patent Appl. Publ. No. 2005/0214414, which are incorporated herein by reference. In some aspects, insoluble alpha-glucan particles replace starch and/or starch derivatives in an edible film or coating, optionally as disclosed in any of the foregoing references. An edible film or coating can be on potato products (e.g., potato strips such as French fries), other vegetables or vegetable products (e.g., zucchini, squash, sweet potatoes, onions, okra, peppers, string beans, tomatoes, cucumbers, lettuce, cabbage, carrots, broccoli, cauliflower, brussel sprouts, bean sprouts, onions, any fresh cut version of a vegetable), mushrooms, fruits (e.g., berries such as raspberries, strawberries, or blue berries, avocados, kiwis, kumquats, oranges, tangerines, apples, pears, bananas, grapefruit, cherries, papaya, lemons, limes, mangos, peaches, cantaloupe, any fresh cut version of a fruit), and/or nuts (peanuts, walnuts, almonds, pecans, cashews, filberts/hazel nuts, Brazil nuts, macadamias), for example. Any other food disclosed herein, as appropriate, can have an edible coating, for example. These and other food products having an edible film or coating herein can be fried or baked in some aspects, and/or the film or coating provides tenderness, moisture retention, protection from moisture, crispness, dietary fiber (in place of digestible starch), oxygen barrier, freshness, and/or anti-ripening. Anti-ripening in some aspects can be measured by the degree to which a coating lowers (e.g., by at least 25%, 50%, 75%, 80%, 85%, or 90%) the emission of a gaseous ripening hormone, such as ethylene, by a plant-based product (e.g., at 15-30, 15-25, or 20-25° C.), and/or by the degree to which plant product softening and/or sweetening is decreased by a coating. An edible coating in some aspects can be prepared by applying an aqueous dispersion comprising insoluble alpha-glucan herein (e.g., at 5-15, 5-12, 5-10, 7.5-15, 7.5-12, or 7.5-10 wt % in water or aqueous solution) to a food product and drying the dispersion (e.g., by air drying, forced air drying, vacuum drying, and/or heating).

A coating composition in some aspects, which can be used to prepare a coating herein, can comprise any of the foregoing components/ingredients/formulations. In some aspects, a coating composition is a latex composition, such as described below.

A composition comprising insoluble alpha-glucan particles herein can be a latex composition. Examples of latex compositions herein include paint (e.g., primer, finishing/decorative), adhesives, films, coatings, and binders. Formulations and/or components (in addition to insoluble alpha-glucan particles herein) of a latex composition herein can be as described in, for example, U.S. Pat. Nos. 6,881,782, 3,440,199, 3,294,709, 5,312,863, 4,069,186 and 6,297,296, and International Patent Appl. Publ. No. WO2019046123, which are all incorporated herein by reference.

Insoluble alpha-glucan particles as presently disclosed can be present in a latex composition in any useful amount, such as about, or at least about, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 40%, 45%, 50%, 55%, 60%, 65%, 70%, 75%, 0.01%-75% 0.01%-5%, 5%-20%, 20%-50% or 50%-75% based on the weight of all the dispersed polymer solids of the latex.

A latex composition in some aspects can comprise a polymer polymerized from at least one ethylenically unsaturated monomer (e.g., monoethylenically unsaturated monomer); polyurethane; epoxy, and/or a rubber elastomer. Examples of monoethylenically unsaturated monomers herein include vinyl monomers, acrylic monomers, allylic monomers, acrylamide monomers, monocarboxylic unsaturated acids and dicarboxylic unsaturated acids.

Examples of suitable vinyl monomers of a polymer in a latex composition herein include any compounds having vinyl functionality (i.e., ethylenic unsaturation) such as vinyl esters (e.g., vinyl acetate, vinyl propionate, vinyl laurate, vinyl pivalate, vinyl nonanoate, vinyl decanoate, vinyl neodecanoate, vinyl butyrates, vinyl benzoates, vinyl isopropyl acetates), vinyl aromatic hydrocarbons (e.g., styrene, methyl styrenes and similar lower alkyl styrenes, chlorostyrene, vinyl toluene, vinyl naphthalene, divinyl benzene), vinyl aliphatic hydrocarbons (e.g., vinyl chloride; vinylidene chloride; alpha olefins such as ethylene, propylene and isobutylene; conjugated dienes such as 1,3-butadiene, methyl-2-butadiene, 1,3-piperylene, 2,3-dimethyl butadiene, isoprene, cyclohexene, cyclopentadiene, and dicyclopentadiene) and vinyl alkyl ethers (e.g., methyl vinyl ether, isopropyl vinyl ether, n-butyl vinyl ether, isobutyl vinyl ether), but excluding compounds having acrylic functionality (e.g., acrylic acid, methacrylic acid, esters of such acids, acrylonitrile, acrylamides). In some aspects, a latex composition herein comprises a vinyl acetate-ethylene copolymer, carboxylated vinyl acetate-ethylene copolymer, and/or or polyvinyl acetate.

Examples of suitable acrylic monomers of a polymer in a latex composition herein include alkyl acrylates, alkyl methacrylates, acrylate acids, methacrylate acids, aromatic derivatives of acrylic and methacrylic acid, acrylamides, and acrylonitrile. Typically, alkyl acrylate and methacrylate monomers (also referred to as alkyl esters of acrylic or methacrylic acid) have an alkyl ester portion containing from 1 to about 18 carbon atoms per molecule, or from 1 to about 8 carbon atoms per molecule. Suitable acrylic monomers include, for example, methyl acrylate and methacrylate, ethyl acrylate and methacrylate, butyl acrylate and methacrylate, propyl acrylate and methacrylate, 2-ethyl hexyl acrylate and methacrylate, cyclohexyl acrylate and methacrylate, decyl acrylate and methacrylate, isodecyl acrylate and methacrylate, benzyl acrylate and methacrylate, isobornyl acrylate and methacrylate, neopentyl acrylate and methacrylate, and 1-adamantyl methacrylate. If acid functionality is desired, acids such as acrylic acid or methacrylic acid can also be used.

A latex composition in some aspects comprises a polyurethane polymer. Examples of suitable polyurethane polymers are those comprising polysaccharides as disclosed in International Patent Appl. Publ. No. WO2018/017789, which is incorporated herein by reference. A latex comprising a polyurethane can be prepared, for example, as disclosed in U.S. Patent Appl. Publ. No. 2016/0347978, which is incorporated herein by reference, and/or comprise the reaction product of one or more polyisocyanates with one or more polyols. Useful polyols include polycarbonate polyols, polyester polyols and polyether polyols, for example. Polycarbonate polyurethane herein can be formed as the reaction product of a polyol such as 1,3-propanediol, 1,4-butanediol, 1,6-hexanediol, diethylene glycol, or tetraethylene glycol, with a diaryl carbonate such as diphenyl carbonate or phosgene. At least one polyisocyanate herein can be an aliphatic polyisocyanate, aromatic polyisocyanate, or polyisocyanate that has both aromatic and aliphatic groups. Examples of polyisocyanates include 1,6-hexamethylene diisocyanate, isophorone diisocyanate, 2,4-toluene diisocyanate, 2,6-toluene diisocyanate, mixtures of 2,4- and 2,6-toluene diisocyanate, bis(4-isocyanatocyclohexyl) methane, 1,3-bis(1-isocyanato-1-methylethyl)benzene, bis(4-isocyanatophenyl)methane, 2,4'-diphenylmethane diisocyanate, 2,2'-diphenylmethane diisocyanate, 2,4-diisocyanatotoluene, bis(3-isocyanatophenyl)methane, 1,4-diisocyanatobenzene, 1,3-diisocyanato-o-xylene, 1,3-diisocyanato-p-xylene, 1,3-diisocyanato-m-xylene, 2,4-diisocyanato-1-chlorobenzene, 2,4-diisocyanato-1-nitrobenzene, 2,5-diisocyanato-1-nitrobenzene, m-phenylene diisocyanate, hexahydrotoluene diisocyanate, 1,5-naphthalene diisocyanate, 1-methoxy-2,4-phenylene diisocyanate, 4,4'-biphenylmethane diisocyanate, 4,4'-biphenylene diisocyanate, 3,3'-dimethyl-4,4'-diphenylmethane, diisocyanate, 3,3'-4,4'-diphenylmethane diisocyanate, and 3,3'-dimethyldiphenylmethane-4,4'-diisocyanate. Also useful herein are polyisocyanate homopolymers comprising allophanate, biuret, isocyanurate, iminooxadiazinedione, or carbodiimide groups, for example. A polyol herein can be any polyol comprising two or more hydroxyl groups, for example, a C2 to C12 alkane diol, ethylene glycol, 1,2-propylene glycol, 1,3-propylene glycol, isomers of butane diol, pentane diol, hexane diol, heptane diol, octane diol, nonane diol, decane diol, undecane diol, dodecane diol, 2-methyl-1,3-propane diol, 2,2-dimethyl-1,3-propane diol (neopentyl glycol), 1,4-bis(hydroxymethyl)cyclohexane, 1,2,3-propane triol (glycerol), 2-hydroxymethyl-2-methyl-1,3-propanol (trimethylolethane), 2-ethyl-2-hydroxymethyl-1,3-propanediol (trimethylolpropane), 2,2-bis(hydroxymethyl)-1,3-propane diol (pentaerythritol); 1,4,6-octanetriol; chloropentanediol; glycerol monoalkyl ether; glycerol monoethyl ether; diethylene glycol; 1,3,6-hexanetriol; 2-methylpropanediol; 2,2,4-trimethyl-1,3-pentanediol, cyclohexanedimethanol, polymeric polyols, for example, polyether polyols or polyester polyols. In some aspects, a polyol herein can be poly(oxytetramethylene) glycol, polyethylene glycol, or poly 1,3-propane diol. A polyol in some aspects can be polyester polyol, such as one produced by transesterification of aliphatic diacids with aliphatic diols. Suitable aliphatic diacids include, for example, C3 to C10 diacids, malonic acid, succinic acid, glutaric acid, adipic acid, pimelic acid, suberic acid, azelic acid, sebacic acid. In some aspects, aromatic and/or unsaturated diacids can be used to form a polyester polyol.

A latex composition in some aspects comprises an epoxy polymer/resin (polyepoxide), such as bisphenol A epoxy resin, bisphenol F epoxy resin, Novolac epoxy resin, aliphatic epoxy resin, or glycidylamine epoxy resin.

A latex composition in some aspects comprises a rubber elastomer. In some aspects, a rubber elastomer can include one or more diene-based sulfur-vulcanizable elastomers having a glass transition temperature (Tg) below −30° C., as determined, for example, by dynamic mechanical analysis. In further examples, a rubber elastomer herein includes natural rubber, synthetic polyisoprene, polybutadiene rubber, styrene/butadiene copolymer rubber, ethylene propylene diene monomer rubber, hydrogenated nitrile butadiene rubber, neoprene, styrene/isoprene/butadiene terpolymer rubber, butadiene/acrylonitrile rubber, polyisoprene rubber, isoprene/butadiene copolymer rubber, nitrile rubber, ethylene-acrylic rubber, butyl and halobutyl rubber, chlorosulfonated polyethylene, fluoroelastomer, hydrocarbon rubber, polybutadiene, and silicone rubber.

A latex composition herein comprises insoluble alpha-glucan particles dispersed in a dispersion (other polymers such as above can optionally be dispersed along with the alpha-glucan particles) or emulsion, where the liquid component of the latex can be water or an aqueous solution. An aqueous solution of a latex in some aspects can comprise an organic solvent that is either miscible or immiscible with water. Suitable organic solvents herein include acetone, methyl ethyl ketone, butyl acetate, tetrahydrofuran, methanol, ethanol, isopropanol, diethyl ether, glycerol ethers, hexane, toluene, dimethyl acetamide, dimethylformamide, and dimethyl sulfoxide.

A latex composition herein can further comprise one or more additives in some aspects. Examples of additives herein include dispersants, rheological aids, antifoams, foaming agents, adhesion promoters, flame retardants, bactericides, fungicides, preservatives, optical brighteners, fillers, anti-settling agents, coalescing agents, humectants, buffers, pigments/colorants (e.g., metallic oxides, synthetic organic pigments, carbon black), viscosity modifiers, antifreeze, surfactants, binders, crosslinking agents, anticorrosion agents, hardeners, pH regulators, salts, thickeners, plasticizers, stabilizers, extenders, and matting agents. Examples of pigments herein include titanium dioxide ($TiO_2$), calcium carbonate, diatomaceous earth, mica, hydrated aluminum oxide, barium sulfate, calcium silicate, clay, silica, talc, zinc oxide, aluminum silicate, nepheline syenite, and mixtures thereof. In some aspects, a latex composition is essentially free from (e.g., less than 1, 0.5, 0.1, or 0.01 wt % of component) starch, starch derivative (e.g., hydroxyalkyl starch), cellulose, and/or cellulose derivative (e.g., carboxymethyl cellulose).

A latex composition in the form of a paint or other coloring agent herein can have a pigment volume concentration (PVC) of about 3% to about 80% in some aspects. As examples, a flat paint can have a PVC in the range of about 55-80%, a primer or undercoat can have a PVC in the range of about 30-50%, and/or a gloss colored paint can have a PVC in the range of about 3-20%. A paint or other coloring agent in some aspects can have a PVC of about 55%, 60%, 65%, 70%, 75%, 80%, 55-80%, 55-75%, 55-70%, 60-80%, 60-75%, 60-70%, 63-67%, 64-66%, 65-80%, 65-75%, or 65-70%. A PVC value herein can be that of a particular pigment (or mix of pigments) such as those disclosed above (e.g., titanium dioxide), for instance. It is notable that insoluble alpha-glucan particles of the present disclosure can act as a pigment extender (see below Examples). For example, insoluble alpha-glucan particles can be used to replace a portion the amount of pigment in a paint (e.g., reduce pigment by about, or at least about, 1%, 2.5%, 5%, 7.5%, 10%, 12.5%, 15%, 17.5%, 20%, 22.5%, 25%, 27.5%, 30%, 5-15%, 5-20%, 5-25%, 5-30%, 10-15%, 10-20%, 10-25%, 10-30%, 15-20%, 15-25%, 15-30%), while optionally simultaneously increasing the opacity of the paint (despite there being less pigment) by about, or at least about, 1%, 1.25%, 1.5%, 1.75%, 2, 2.25%, 1-2.25%, 1-2%, or 1-1.75%. Replacement of pigment with insoluble alpha-glucan particles herein can be on a basis of about 0.9-1.1 (e.g., 1.0) parts pigment to about 0.5-0.7 (e.g., 0.6 parts) insoluble alpha-glucan particles, for example. Aside from these advantages (opacity, less pigment needed), insoluble alpha-glucan particles of the present disclosure are believed to provide one or more other physical properties to a latex composition (e.g., for use as a paint or other coloring agent): increased hardness, reduced tackiness, decreased gloss (i.e., providing a matte effect), increased shear strength, better abrasion resistance, improved dry time, improved fade resistance, lower blistering, and/or improved hand (a less tacky feel), for example, as compared to a latex composition that only differs by not comprising the insoluble alpha-glucan particles.

A latex composition herein can be applied to the substrate of an article (above) using any method known in the art. Typically, after application of the latex composition, at least a portion of the aqueous solution is removed, for example by drying, to provide an adhesive, film, coating, or binder comprising the latex composition in a dry or semi-dry form. Suitable application methods include air knife coating, rod coating, bar coating, wire bar coating, spray coating, brush coating, cast coating, flexible blade coating, gravure coating, jet applicator coating, short dwell coating, slide hopper coating, curtain coating, flexographic coating, size-press coating, reverse roll coating, and transfer roll coating. A latex composition can be applied on at least a portion of a substrate, and can be in one or more coats/applications, for example.

Some aspects herein are drawn to a pigment-comprising composition. A pigment-comprising composition can be in a liquid form (e.g., an aqueous or non-aqueous composition herein) or solid form (e.g., a dry composition herein). Examples of a pigment-comprising composition herein include any of such compositions disclosed elsewhere herein (e.g., paint, primer, stain), ink, dye (e.g., food-coloring dye, fabric-coloring dye), resin, sunscreen, and cosmetics (e.g., mascara, blush, nail varnish/polish, lipstick, gloss, eyeliner, foundation, eye shadow, skin decoration composition). A pigment-comprising composition can be in a liquid form (e.g., an aqueous or non-aqueous composition herein) or solid form (e.g., a dry composition herein). A pigment in a pigment-comprising composition can be any pigment herein, for example. Examples of a pigment for these and/or other aspects herein include oxides of titanium (e.g., titanium dioxide), zinc, iron, zirconium, cerium, and chromium; manganese violet; ultramarine blue; chromium hydrate; Prussian Blue; zinc sulfide; nitroso, nitro, azo, xanthene, quinoline, anthraquinone and/or phthalocyanine compounds; metal complex compounds; and isoindolinone, isoindoline, quinacridone, perinone, perylene, diketopyrrolopyrrole, thioindigo, dioxazine, triphenylmethane and/or quinophthalone compounds. Further pigment examples useful herein are disclosed in U.S. Patent. Appl. Publ. No. 2006/0085924, which is incorporated herein by reference.

In some aspects, a composition comprising insoluble alpha-glucan particles can be in the form of a composite (e.g., rubber composite or polyurethane composite) such as disclosed in International Patent Appl. Publ. Nos. WO2018/081263 or WO2018/017789, or U.S. Patent Appl. Publ. Nos. 2019/0225737 or 2017/0362345, all of which are incorporated herein by reference. It can optionally be stated that a composite as presently disclosed comprises at least one polymer in addition to insoluble alpha-glucan particles. One or more of the above components (e.g., a rubber or polyurethane) of a latex composition can optionally be an additional polymer in such a composite. An additional polymer of a composite herein can be rubber, polyurethane, thermoplastic polymer, polyethylene, polypropylene, ethylene copolymer, polyvinyl butyrate, polylactic acid, polyvinyl alcohol, polyamide, polyether thermoplastic elastomer, polyester, polyether ester, ethylene vinyl alcohol copolymer, starch, cellulose, or any suitable polymer as disclosed above for latex components.

Rubber in some aspects can be one or more of natural rubber, synthetic rubber, polyisoprene, polybutadiene, styrene-butadiene copolymer, styrene-isoprene copolymer, butadiene-isoprene copolymer, styrene-butadiene-isoprene terpolymer, ethylene propylene diene monomer rubber, hydrogenated nitrile butadiene rubber, silicone rubber, or neoprene, for instance. Examples of composites herein comprising rubber include tires (e.g., auto/bicycle; pneumatic tire; including tire treads and/or sidewalls), belts (e.g., conveyor belts, power transmission belts), hoses, gaskets, footwear (e.g., shoes, sneakers, boots; soles, cushioning, and/or aesthetic features), coatings, films, and adhesives. Rubber composites herein typically are vulcanized. Notably, the inclusion of insoluble alpha-glucan particles herein in a composite comprising rubber can provide advantages such as lower cost, lower density, lower energy consumption during processing, and/or better or equal performance as compared to use of an incumbent filler such as carbon black or silica (e.g., increased wet traction, reduced rolling resistance, lighter weight, and/or mechanical strength); such performance enhancements can be with tires in some aspects. In some aspects, insoluble alpha-glucan particles herein replace about, or at least about, 25, 30, 35, 40, 45, 50, 55, 60, 65, 70, 75, 80, 85, 90, 95, or 100 wt % of an incumbent filler (e.g., carbon black, or silica) that is typically used in a rubber composite such as a tire. It is noted that rubber composite tires currently on the market (that do not comprise insoluble alpha-glucan particles herein) typically comprise up to about 30 wt % of an incumbent filler such as carbon black. Thus, a rubber composite herein such as a tire can comprise about, or at least about, 5, 10, 15, 20, 25, or 30 wt % insoluble alpha-glucan particles as presently disclosed, for example. A rubber composition comprising insoluble alpha-glucan particles herein can have a low minimum elastic torque ($M_L$) (e.g., less than, or about, 0.10, 0.08, 0.06, 0.04, 0.03, or 0.02 dNm [deciNewton-meter]) in some aspects, and so a method of mixing a rubber composition during its preparation is disclosed. A rubber composition comprising insoluble alpha-glucan particles herein can have, or be within plus/minus 5% or 10% of, any of the features/values (e.g., density, tensile strength, elongation, modulus, tan delta, cure time, elastic torque) listed in Table 5 below (Example 9), for example. A rubber composition comprising insoluble alpha-glucan particles as a filler herein can have any of the other non-filler ingredients/components listed in Table 4 below (Example 9) (optionally within plus/minus 5% or 10% of the listed content thereof), and/or have the listed content of (or plus/minus 5% or 10% thereof) insoluble alpha-glucan particles, for example.

The present disclosure also concerns a composition comprising at least two different phases and insoluble alpha-glucan particles herein, wherein the particles are at the interface of the two phases. Typically, the particles can modify (e.g., reduce) the interfacial tension between the two phases. One phase can be hydrophilic (e.g., be an aqueous composition herein such as water, aqueous solution, or aqueous dispersion), while another phase can be hydrophobic (e.g., oil and/or other organic liquid), for example. While insoluble alpha-glucan particles herein are located at the interfacial surface of the two phases, particles can optionally also be present in at least one of the different phases (e.g., hydrophilic phase). Interfacial tension can be measured in units of mN/m (milli-Newtons per meter). In some aspects, insoluble alpha-glucan particles can reduce interfacial tension by about, or at least about, 2, 3, 4, 5, 6, 7, 8, 9, 10, 15, 20, 25, 30, 35, 40, 5-30, 5-25, 5-20, 5-15, 5-10, 10-30, 10-25, 10-20, or 10-15 mN/m.

Non-limiting examples of compositions and methods disclosed herein include:

1a. A composition comprising insoluble alpha-glucan particles having a degree of crystallinity of at least about 0.65, wherein the insoluble alpha-glucan has a weight-average degree of polymerization (DPw) of at least 15, and at least 50% of the glycosidic linkages of the insoluble alpha-glucan are alpha-1,3 glycosidic linkages.

2a. The composition embodiment 1a, wherein at least about 90% of the glycosidic linkages of the insoluble alpha-glucan are alpha-1,3 linkages.

3a. The composition of embodiment 1a, wherein at least about 99% of the glycosidic linkages of the insoluble alpha-glucan are alpha-1,3 linkages.

4a. The composition of embodiment 1a, 2a, or 3a, wherein the DPw of the insoluble alpha-glucan is at least about 35 or 40, or is about 35 or 40 to about 100.

5a. The composition of embodiment 1a, 2a, or 3a, wherein the DPw of the insoluble alpha-glucan is about 35 or 40 to about 60.

6a. The composition of embodiment 1a, 2a, 3a, 4a, or 5a, wherein the composition is an aqueous composition (e.g., dispersion, emulsion).

7a. The composition of embodiment 6a, wherein the aqueous composition is a dispersion.

8a. The composition of embodiment 7a, wherein the insoluble alpha-glucan particles are dispersed through at least about 90% of the volume of the dispersion.

9a. The composition of embodiment 6a, 7a, or 8a, wherein the aqueous composition has a pH of about 0.0 to about 5.0.

10a. The composition of embodiment 6a, 7a, or 8a, wherein the aqueous composition has a pH of about 0.0 to about 1.0, or about 0.0 to about 2.0.

11a. The composition of embodiment 6a, 7a, or 8a, wherein the aqueous composition has a pH of about 2.0 to about 4.0, optionally wherein this pH range provides an anti-microbial effect to the composition (e.g., kills, or inhibits growth/proliferation of, microbes such as bacteria, yeast, or algae).

12a. The composition of embodiment 1a, 2a, 3a, 4a, 5a, 6a, 7a, 8a, 9a, 10a, or 11a, wherein at least 70% by weight of the insoluble alpha-glucan particles have a diameter of less than 1.0 micron.

13a. The composition of embodiment 1a, 2a, 3a, 4a, 5a, 6a, 7a, 8a, 9a, 10a, or 11a, wherein 45-55% by weight of the insoluble alpha-glucan particles have a diameter of less than 0.35 micron.

14a. The composition of embodiment 1a, 2a, 3a, 4a, 5a, 6a, 7a, 8a, 9a, 10a, 11a, 12a, or 13a, wherein the temperature of the composition is up to about 125° C.

15a. The composition of embodiment 1a, 2a, 3a, 4a, 5a, 6a, 7a, 8a, 9a, 10a, 11a, 12a, 13a, or 14a, wherein the insoluble alpha-glucan particles having a degree of crystallinity of at least about 0.7.

16a. The composition of embodiment 1a, 2a, 3a, 4a, 5a, 6a, 7a, 8a, 9a, 10a, 11a, 12a, 13a, 14a, or 15a, wherein at least 80 wt % of the particles are in the form of plates.

17a. The composition of embodiment 1a, 2a, 3a, 4a, 5a, 6a, 7a, 8a, 9a, 10a, 11a, 12a, 13a, 14a, 15a, or 16a, wherein the composition is a household care product, personal care product, industrial product, ingestible product (e.g., food product), or pharmaceutical product.

18a. The composition of embodiment 1a, 2a, 3a, 4a, 5a, 6a, 7a, 8a, 9a, 10a, 11a, 12a, 13a, 14a, 15a, 16a, or 17a, wherein the composition is: (a) a latex composition, such as paint or adhesive; (b) a pigment-comprising composition such as paint or sunscreen; (c) a film or coating, such as an edible film or coating, (d) a detergent composition; (e) a composite comprising at least one polymer in addition to the insoluble alpha-glucan particles, optionally wherein the additional polymer is polyurethane, rubber, or a thermoplastic polymer; or (f) an encapsulant that encapsulates a composition comprising a compound, optionally wherein the encapsulant allows for controlled release of the compound.

19a. The composition of embodiment 1a, 2a, 3a, 4a, 5a, 6a, 7a, 8a, 9a, 10a, 11a, 12a, 13a, 14a, 15a, 16a, 17a, or 18a, wherein the composition further comprises at least one additive that modifies the mechanical properties of the composition, optionally wherein the additive is selected from a crosslinker, plasticizer, conditioning agent, dispersing agent, or wetting agent, optionally further wherein the composition is a film or coating.

20a. The composition of embodiment 1a, 2a, 3a, 4a, 5a, 6a, 7a, 8a, 9a, 10a, 11a, 12a, 13a, 14a, 15a, 16a, 17a, 18a, or 19a, wherein the composition comprises at least two different phases, and said insoluble alpha-glucan particles are at the interface of the two different phases.

21a. A method of producing insoluble alpha-glucan particles (e.g., as recited in any of embodiments 1a-5a, 12a, 13a, 15a, or 16a), the method comprising: (a) providing insoluble alpha-glucan as produced in an enzymatic reaction comprising at least water, sucrose and a glucosyltransferase enzyme that synthesizes the insoluble alpha-glucan, wherein the insoluble alpha-glucan has a weight-average degree of polymerization (DPw) of at least about 200 and at least 50% of the glycosidic linkages of the insoluble alpha-glucan are alpha-1,3 glycosidic linkages; (b) hydrolyzing the insoluble alpha-glucan to insoluble alpha-glucan particles with a DPw of about 35 or 40 to about 100, wherein the hydrolyzing is performed under aqueous conditions at a pH of 2.0 or less, and (c) optionally isolating the insoluble alpha-glucan particles produced in step (b).

Non-limiting examples of compositions and methods disclosed herein also include:

1b. A composition comprising insoluble alpha-glucan particles, wherein at least 80 wt % of the particles are in the form of plates and at least 50% of the glycosidic linkages of the insoluble alpha-glucan are alpha-1,3 glycosidic linkages, and: (i) at least 70% by weight of the insoluble alpha-glucan particles have a diameter of less than 1.0 micron, and/or (ii) 45-55% by weight of the insoluble alpha-glucan particles have a diameter of less than 0.35 micron.

2b. The composition of claim 1b, wherein at least about 90% of the glycosidic linkages of the insoluble alpha-glucan are alpha-1,3 linkages.

3b. The composition of claim 1b, wherein at least about 99% of the glycosidic linkages of the insoluble alpha-glucan are alpha-1,3 linkages.

4b. The composition of claim 1b or 2b, wherein the insoluble alpha-glucan particles have a degree of crystallinity of at least about 0.65.

5b. The composition of claim 4b, wherein the insoluble alpha-glucan particles have a degree of crystallinity of at least about 0.7.

6b. The composition of claim 1b, 2b, 3b, 4b, or 5b, wherein the weight-average degree of polymerization (DPw) of the insoluble alpha-glucan is at least 15.

7b. The composition of claim 6b, wherein the DPw of the insoluble alpha-glucan is at least about 35 or 40, or is about 35 or 40 to about 100.

8b. The composition of claim 6b, wherein the DPw of the insoluble alpha-glucan is about 35 or 40 to about 60.

9b. The composition of claim 1b, 2b, 3b, 4b, 5b, 6b, 7b, or 8b, wherein the composition is an aqueous composition (e.g., dispersion, emulsion).

10b. The composition of claim 9b, wherein the aqueous composition is a dispersion.

11b. The composition of claim 10b, wherein the insoluble alpha-glucan particles are dispersed through at least about 90% of the volume of the dispersion.

12b. The composition of claim 9b, 10b, or 11b, wherein the aqueous composition has a pH of about 0.0 to about 5.0.

13b. The composition of claim 9b, 10b, or 11b, wherein the aqueous composition has a pH of about 0.0 to about 1.0, or about 0.0 to about 2.0.

14b. The composition of claim 9b, 10b, or 11b, wherein the aqueous composition has a pH of about 2.0 to about 4.0, optionally wherein this pH range provides an anti-microbial effect to the composition (e.g., kills, or inhibits growth/proliferation of, microbes such as bacteria, yeast, or algae).

15b. The composition of claim 1b, 2b, 3b, 4b, 5b, 6b, 7b, 8b, 9b, 10b, 11b, 12b, 13b, or 14b, wherein the temperature of the composition is up to about 125° C.

16b. The composition of claim 1b, 2b, 3b, 4b, 5b, 6b, 7b, 8b, 9b, 10b, 11b, 12b, 13b, 14b, or 15b, wherein the composition is a household care product, personal care product, industrial product, ingestible product (e.g., food product), or pharmaceutical product.

17b. The composition of claim 1b, 2b, 3b, 4b, 5b, 6b, 7b, 8b, 9b, 10b, 11b, 12b, 13b, 14b, 15b, or 16b, wherein the composition is: (a) a latex composition, such as paint or adhesive; (b) a pigment-comprising composition such as paint or sunscreen; (c) a film or coating, such as an edible film or coating, (d) a detergent composition; (e) a composite comprising at least one polymer in addition to the insoluble alpha-glucan particles, optionally wherein the additional polymer is polyurethane, rubber, or a thermoplastic polymer; or (f) an encapsulant that encapsulates a composition comprising a compound, optionally wherein the encapsulant allows for controlled release of the compound.

18b. The composition of claim 1b, 2b, 3b, 4b, 5b, 6b, 7b, 8b, 9b, 10b, 11b, 12b, 13b, 14b, 15b, 16b, or 17b, wherein the composition further comprises at least one additive that modifies the mechanical properties of the composition, optionally wherein the additive is selected from a crosslinker, plasticizer, conditioning agent, dispersing agent, or wetting agent, optionally further wherein the composition is a film or coating.

19. The composition of claim 1b, 2b, 3b, 4b, 5b, 6b, 7b, 8b, 9b, 10b, 11b, 12b, 13b, 14b, 15b, 16b, 17b, or 18b, wherein the composition comprises at least two different phases, and said insoluble alpha-glucan particles are at the interface of the two different phases.

20b. A method of producing insoluble alpha-glucan particles (e.g., as recited in any of embodiments 1b-8b), the method comprising: (a) providing insoluble alpha-glucan as produced in an enzymatic reaction comprising at least water, sucrose and a glucosyltransferase enzyme that synthesizes the insoluble alpha-glucan, wherein the insoluble alpha-glucan has a weight-average degree of polymerization (DPw) of at least about 200 and at least 50% of the glycosidic linkages of the insoluble alpha-glucan are alpha-1,3 glycosidic linkages, (b) hydrolyzing the insoluble alpha-glucan to insoluble alpha-glucan particles with a DPw of up to about 100, wherein the hydrolyzing is performed under aqueous conditions at a pH of 2.0 or less, and (c) optionally isolating the insoluble alpha-glucan particles produced in step (b).

EXAMPLES

The present disclosure is further exemplified in the following Examples. It should be understood that these Examples, while indicating certain aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

Example 1

Producing Highly Crystalline Insoluble Alpha-Glucan

This Example describes preparing crystalline alpha-glucan in the form of insoluble plates. In particular, plates of insoluble alpha-1,3-glucan were prepared by subjecting enzymatically synthesized alpha 1,3 glucan to hydrolysis.

Insoluble alpha-1,3-glucan used in this Example was first prepared by enzymatic synthesis in a manner similar to what is described in U.S. Patent Appl. Publ. Nos. 2018/0340199 and 2019/0078063, which are both incorporated herein by reference. In general, a glucan synthesis reaction was performed comprising water, sucrose, buffer, filtrate from an earlier glucan synthesis reaction (contains, e.g., gluco-oligosaccharide byproducts of the earlier glucan synthesis reaction), and an amino acid-modified, high product-yielding glucosyltransferase enzyme. Following the reaction, the alpha-1,3-glucan product (insoluble, ~100% alpha-1,3 linkages, DPw of about 800) was filtered and washed to remove most fructose and other residual soluble sugars (e.g., glucose, sucrose, leucrose, DP2-DP8 gluco-oligosaccharides). Samples of the washed product were then either collected into wet cakes (never-dried) of about 20-40 wt % solids or dried in a rotary dryer to powders of about 88-95 wt % solids.

Samples of both never-dried and dried insoluble alpha-1,3-glucan were then subjected to hydrochloric acid hydrolysis procedures at a pH of almost 0 at 80° C. to produce reduced molecular weight insoluble alpha-1,3-glucan. Each hydrolysis reaction as initiated contained 8 wt % alpha-1,3-glucan. Procedures disclosed in U.S. Patent Appl. Publ. No. 2013/0244287 (incorporated herein by reference), which describes mineral acid hydrolysis of insoluble alpha-1,3-glucan to soluble alpha-1,3-glucan, can be applied with appropriate modification to hydrolyze alpha-1,3-glucan to a lower molecular weight, but insoluble, form. Hydrolysis reactions were allowed to proceed for 1 hour, 8 hours, 1 day, or 3 days before being neutralized. Each hydrolyzed, insoluble alpha-1,3-glucan product was then analyzed for molecular weight. FIG. 1 shows that insoluble alpha-1,3-glucan with a weight-average degree of polymerization (DPw) of roughly 40-60 was produced after one day of hydrolysis of either never-dried or dried insoluble alpha-1,3-glucan. Notably, this molecular weight was stable, remaining at a similar DPw for the duration of hydrolysis under the very low pH conditions (FIG. 1). In a separate hydrolysis, insoluble alpha-1,3-glucan with a DPw of about 39 was produced (data not shown).

Crystallinity (or crystallinity index [CI]) of the alpha-1,3-glucan samples was measured by wide-angle X-ray scattering (WAXS) as follows. Glucan powder samples were dried for a minimum of two hours or overnight (but sometimes over the weekend) in a vacuum oven set at 60° C. Immediately before starting the diffraction scan, each sample was removed from the oven and transferred into a stainless steel holder with a well of about 1.5 cm wide by 4 cm long by 4 mm deep. The well was open at the side such that powder could be poured in through the side, with a glass plate clipped onto the top of the holder. The powder was packed down several times throughout the filling process by hitting the opposite side of the holder against the table repeatedly. Finally, the holder was turned right-side-up, the glass plate was removed, and the holder was loaded into a diffractometer. The time from the opening of the oven to the start of the scan was five minutes or less. An X'PERT MPD POWDER diffractometer (PANalytical B.V., The Netherlands) in reflection mode was used to measure the X-ray diffraction pattern of each powder sample. The X-ray source was a Cu X-ray tube line source with an optical focusing mirror and a $\frac{1}{16}°$ narrowing slit. X-rays were detected with a 1-D detector and an anti-scatter slit set at $\frac{1}{8}°$. Data were collected in the range of 4 to 60 degrees of two-theta at 0.1 degrees per step. The scan took about 46 minutes in total. The resulting X-ray pattern was then analyzed by subtracting a linear baseline from 7.2 to 30.5 degrees, subtracting the XRD pattern of a known amorphous alpha-1,3-glucan sample that had been scaled to fit the current data, and then fitting the remaining crystal peaks in that range with a series of Gaussian curves corresponding to known dehydrated alpha-1,3-glucan crystal reflections. The area corresponding to the crystal peaks was then divided by the total area under the baseline-subtracted curve to yield a crystallinity index.

Figure 2:
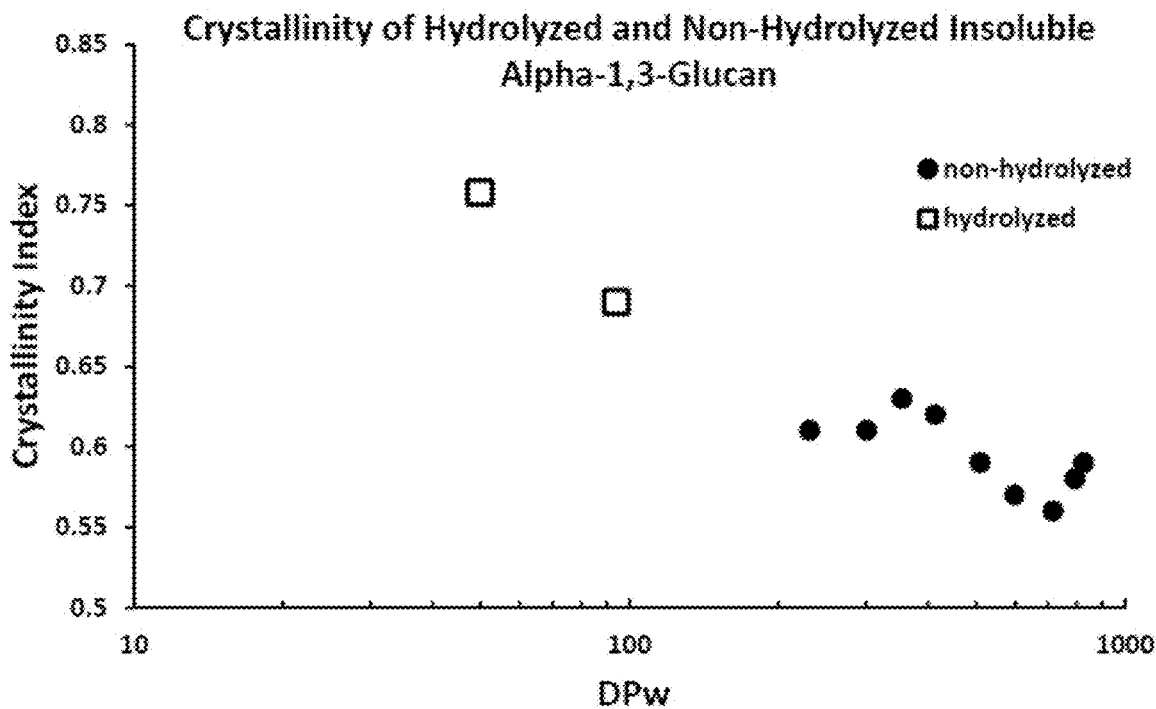
FIG. 2: Shown is the crystallinity of hydrolyzed (DPw 50) and non-hydrolyzed (DPw~800) alpha-1,3-glucan. Refer to Example 1.

The crystallinity of the alpha-1,3-glucan samples prepared above by hydrolysis was compared to the crystallinity of enzymatically polymerized alpha-1,3-glucan that was not subjected to hydrolysis. FIG. 2 shows that hydrolyzed alpha-1,3-glucan has substantially greater crystallinity (over 0.65) compared to non-hydrolyzed alpha-1,3-glucan. In particular, hydrolyzed alpha-1,3-glucan with a DPw of 50 (made by acid-hydrolyzing, as above, wet cake for 48 hours at 40° C.) had a crystallinity of about 0.76 (FIG. 2, left square). A sample of hydrolyzed alpha-1,3-glucan with a DPw of 94 (made by acid-hydrolyzing, as above, wet cake for 1 hour at 40° C.) had a crystallinity of about 0.69 (FIG. 2, left square). However, samples of non-hydrolyzed alpha-1,3-glucan (~100% alpha-1,3 linkages) produced enzymatically and having DPw's ranging from ~230 to ~830 had lower crystallinities (FIG. 2, filled circles) (the molecular weight of alpha-1,3-glucan as produced enzymatically can be modulated to be within the range of DPw 230-830 using a technique as described in, for example, U.S. Patent Appl. Publ. No. 2015/0064748, which is incorporated herein by reference).

Using electron microscopy, the microstructure of hydrolyzed alpha-1,3-glucan (DPw 50, 0.76 CI, 1.2 PDI) was compared to that of non-hydrolyzed alpha-1,3-glucan (DPw~800) (as produced above) (FIGS. 3A-D). The glucan samples were imaged by dry-cast electron microscopy using phosphotungstate as a contrast agent, as follows. Slurries of DPw 50 and DPw~800 alpha-1,3-glucan were purified by multiple rounds of centrifugation and redispersion into DI water. The final purified glucan samples were diluted 100-fold and then sonicated for 3 minutes. Once sonication was completed, supernatant from each preparation was isolated to prepare a dry-cast transmission electron microscopy (TEM) sample on a copper mesh TEM grid. Phosphotungstic acid was then used for negative contrast staining, after which TEM imaging was performed. The captured TEM images usually were from sections located at the edge of a larger thick sample deposited on the TEM grid. The hydrolyzed alpha-1,3-glucan (DPw 50) exhibited two-dimensional structures (>about 90 wt % of material that was not aggregated was in the form of plates) (FIGS. 3B and 3D), whereas the non-hydrolyzed alpha-1,3-glucan (DPw~800) exhibited larger, three-dimensional fibrillar structures (FIGS. 3A and 3C). TEM imaging of non-hydrolyzed alpha-1,3-glucan (~100% alpha-1,3 linkages) produced enzymatically and having a DPw of about 260 showed a microstructure very similar to that of non-hydrolyzed alpha-1,3-glucan (DPw~800) (data not shown).

Figure 4:
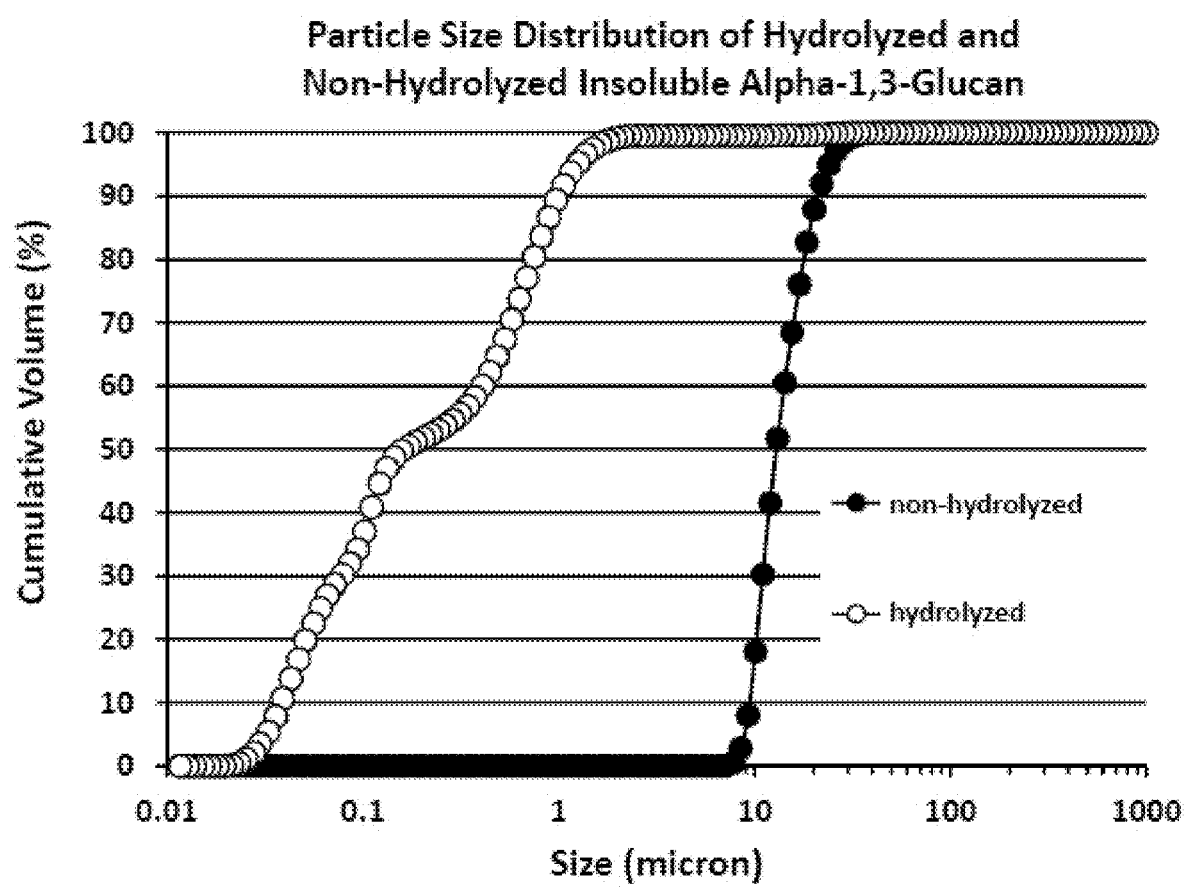
FIG. 4: Shown are particle size distributions of hydrolyzed (DPw 50) and non-hydrolyzed (DPw~800) alpha-1,3-glucan in aqueous dispersions. Refer to Example 1.

Particle size measurement by light scatter analysis of aqueous dispersions indicated that the hydrolyzed alpha-1,3-glucan (DPw 50) had a particle size distribution in which ~90% by weight of all particles were under 1 micron in size (D50 value ranged from about 0.15 to 0.2 micron, but can range from about 0.1 to 1.0 micron), while the non-hydrolyzed alpha-1,3-glucan (DPw~800) had a particle size distribution in which >80% by weight of all particles were over 10 microns (D50 value ranged from about 10 to 20 microns, but can range from about 5 to 50 microns) (FIG. 4).

Example 2

Aqueous Dispersions of Highly Crystalline Insoluble Alpha-Glucan are Stable Across Changes in pH This Example describes the effects of lowering pH on the viscosities of aqueous dispersions of highly crystalline insoluble alpha-glucan or non-crystalline alpha-glucan. In particular, dispersions of insoluble alpha-1,3-glucan (DPw 50, 0.76 CI) retained a stable viscosity profile under low pH conditions, whereas dispersions of insoluble alpha-1,3-glucan (DPw~800) exhibited changes in viscosity under the same conditions.

Figure 5A:
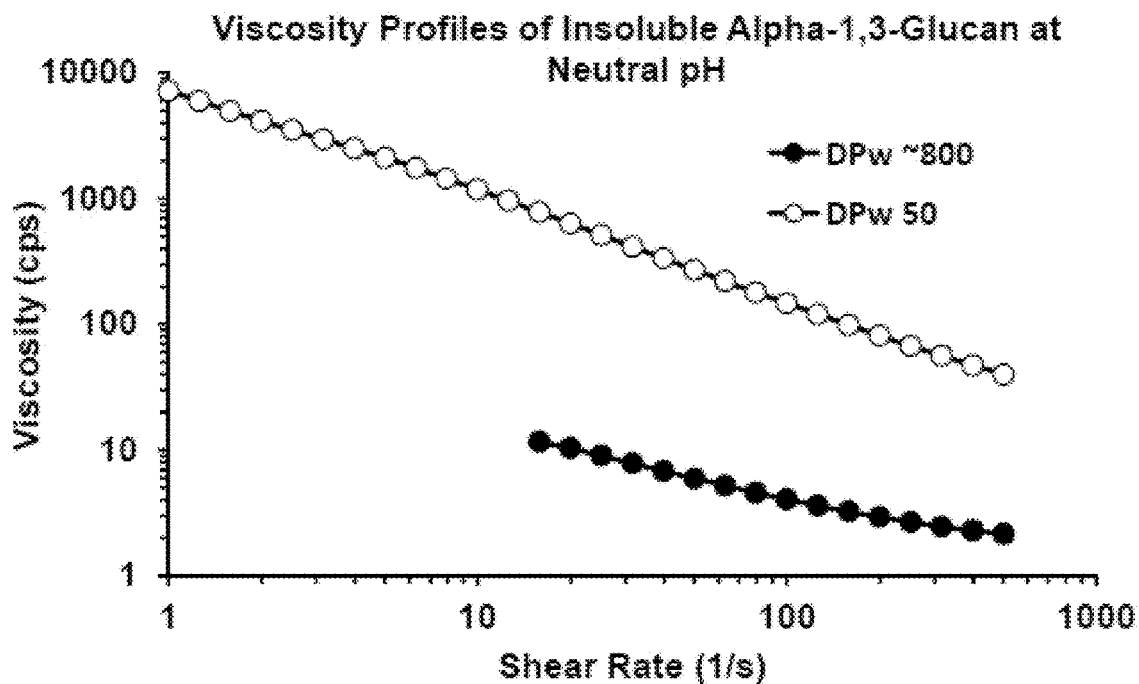
FIG. 5A: Shown are the viscosity profiles of 5 wt % aqueous dispersions of DPw 50 alpha-1,3-glucan (0.76 CI) or DPw~800 alpha-1,3-glucan at a neutral pH of 6.4. Refer to Example 2.
Figure 5B:
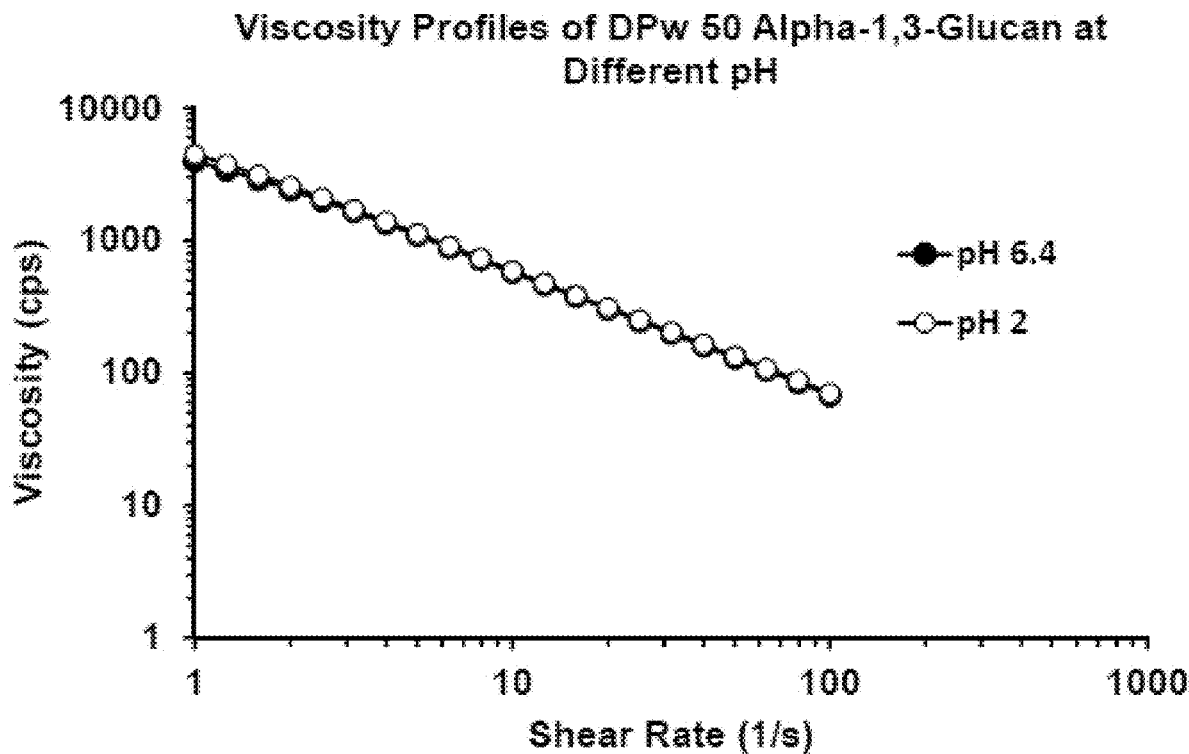
FIG. 5B: Shown are the viscosity profiles of 5 wt % aqueous dispersions of alpha-1,3-glucan (DPw 50, 0.76 CI) at pH 2.0 or pH 6.4. Refer to Example 2.

Aqueous dispersions (5 wt %, room temperature) of insoluble alpha-1,3-glucan (DPw 50, 0.76 CI, as prepared in Example 1) or insoluble alpha-1,3-glucan (DPw~800, as prepared in Example 1) were prepared and adjusted to pH 2.0 or 6.4. The aqueous dispersions were then analyzed for viscosity (using a BROOKFIELD viscometer at shear rates between 1-1000 s$^{-1}$) (FIGS. 5A-B). At pH 6.4, dispersions of the DPw 50 alpha-1,3-glucan exhibited about a two orders of magnitude higher viscosity profile as compared to the viscosity profile of dispersions of the DPw~800 alpha-1,3-glucan (FIG. 5A). Also of note, dispersions of the DPw 50 alpha-1,3-glucan at pH 2.0 exhibited no change in viscosity profile compared to the neutral condition of pH 6.4 (FIG. 5B). This unaltered viscosity profile is unique, since other polysaccharides such as nanocellulose and microcrystalline cellulose exhibit significant drops in viscosity in low pH conditions (U.S. Pat. No. 2,978,446, incorporated herein by reference).

Figure 6:
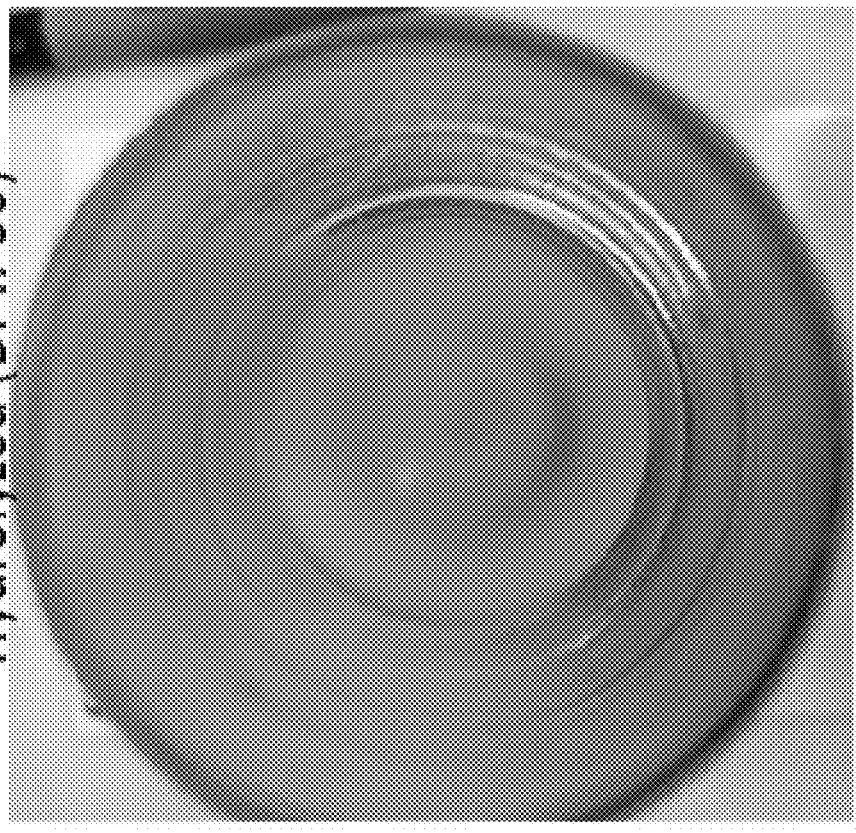
FIG. 6: Shown are aqueous preparations (room temperature, pH 4.0) initially set up as dispersions comprising 4 wt % of DPw 50 (0.76 CI) or DPw~800 alpha-1,3-glucan and 14 wt % vinyl acetate/ethylene (VAE) latex. While DPw 50 alpha-1,3-glucan remained dispersed, DPw~800 alpha-1,3-glucan settled out. Refer to Example 2.
Figure 6:
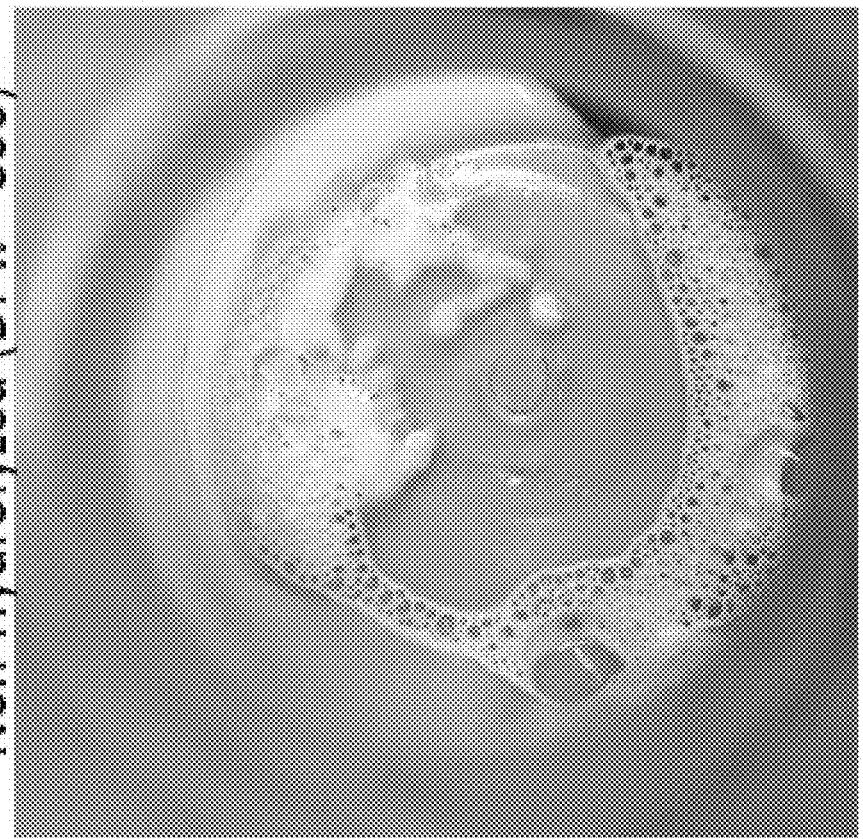

The unique high viscosity at low concentration (5 wt %, above) of insoluble alpha-1,3-glucan (DPw 50, 0.76 CI), and its pH-stability, allowed for good compatibility when mixed into a low pH latex dispersion. In particular, FIG. 6 compares aqueous preparations that were initially set up as dispersions (room temperature, pH 4.0) comprising 4 wt % alpha-1,3-glucan (either DPw 50 or DPw~800 glucan from above) and 14 wt % vinyl acetate/ethylene (VAE) latex. While VAE dispersions with DPw 50 alpha-1,3-glucan remained stable for at least 3 weeks (the dispersions were discarded after this period) and are believed to be stable for at least 6-12 months, DPw~800 alpha-1,3-glucan settled out of VAE dispersions (FIG. 6) in under one hour. Typically, latex dispersions are pH-stabilized at either pH 3-4 or pH 8-9, but the low pH condition of pH 3-4 makes it challenging for using polysaccharides in latex dispersions under this pH-stabilization regimen. While DPw~800 alpha-1,3-glucan has been shown to be somewhat stable in such low pH dispersions at higher concentrations (data not shown), its instability at 4 wt % as shown here suggests its use at low concentrations (e.g., >5 wt %) is problematic. Thus, it is notable that insoluble alpha-1,3-glucan (DPw 50) was stably dispersible under these conditions.

Example 3

Highly Crystalline Insoluble Alpha-Glucan can be Used as a Pigment Extender in Paint Compositions This Example describes using highly crystalline insoluble alpha-glucan as a pigment extender in paint compositions. In particular, insoluble alpha-1,3-glucan (DPw 50, 0.76 CI) was used to replace titanium dioxide (TiO$_2$) pigment in paint, and enhanced the opacity function of this pigment. This enhancement was coupled with being able to reduce the amount of TiO$_2$ used in paint.

TiO$_2$ is the most widely used white pigment in paint due to its high refractive index. An issue with using TiO$_2$ as pigment is the inherent colloidal instability of TiO$_2$ particles. TiO$_2$ particles are usually coated with SiO$_2$ to address this problem. However, even with an SiO$_2$-coated structure, the efficiency of TiO$_2$ particles as a pigmenting agent is decreased if TiO$_2$ particles are not spaced adequately (ideal spacing is ~200 nm).

TiO$_2$ particle-spacing additives are referred to as TiO$_2$ extenders. It was found in this Example that insoluble alpha-1,3-glucan (DPw 50, 0.76 CI) can be used as an efficient TiO$_2$ extender in paint, as follows. White paint formulations were generally prepared as follows. A control paint formulation (no alpha-1,3-glucan added) contained 65 pigment volume concentration (PVC) TiO$_2$ pigment, while experimental paint formulations contained insoluble alpha-1,3-glucan (either of the DPw 50 or DPw~800 samples, above) in replacement of a certain portion of the $TiO_2$ pigment component. This replacement was based on a ratio of $TiO_2$ to alpha-1,3-glucan of 1.0 to 0.6 (based on PVC in the formulation). The formulated paints were applied using a 3-mil bird bar and dried overnight at about 70° C. and 50% humidity, after which L* (whiteness) and opacity (Y) levels of the dried paint were measured (Table 1) as described in International Patent Appl. Publ. No. WO2019046123, which is incorporated herein by reference.

TABLE 1

Performance of Paint Comprising Insoluble Alpha-1,3-Glucan in Replacement of $TiO_2$ Pigment

| % $TiO_2$ Reduction | Insoluble Alpha-1,3-Glucan [a] | | | |
|---|---|---|---|---|
| | DPw ~800 | | DPw 50 (0.76 CI) | |
| | L* [b] | Opacity (Y) [c] | L* [b] | Opacity (Y) [c] |
| 0% | 95.3 | 88.6 | 95.3 | 88.6 |
| 8% | 95.4 | 88.7 | 95.6 | 89.5 |
| 15% | 95.4 | 89.1 | 95.5 | 89.6 |
| 23% | 95.2 | 88.2 | 95.6 | 89.7 |
| 30% | 95.2 | 88.4 | 95.6 | 90.1 |

[a] Insoluble alpha-1,3-glucan used to replace listed percentage of $TiO_2$ in paint formulation, based on a ratio of 1.0 parts $TiO_2$ to 0.6 parts alpha-1,3-glucan.
[b] L* value denotes whiteness (L* = 0 indicates black and L* = 100 indicates diffuse white).
[c] Opacity (Y): higher numbers equate to better opacity, or hiding power.

Notably, as shown in Table 1, as $TiO_2$ was replaced with DPw 50 alpha-1,3-glucan, continuous performance increases in whiteness (L*) and opacity were obtained.

Example 4

Highly Crystalline Insoluble Alpha-Glucan has Unique Optical Properties

This Example describes preparing an optically transparent product using crystalline insoluble alpha-glucan. In particular, a material comprising insoluble alpha-1,3-glucan (DPw 50, 0.76 CI) exhibited high optical clarity, whereas material comprising insoluble alpha-1,3-glucan (DPw~800) exhibited much lower optical clarity.

Figure 7:
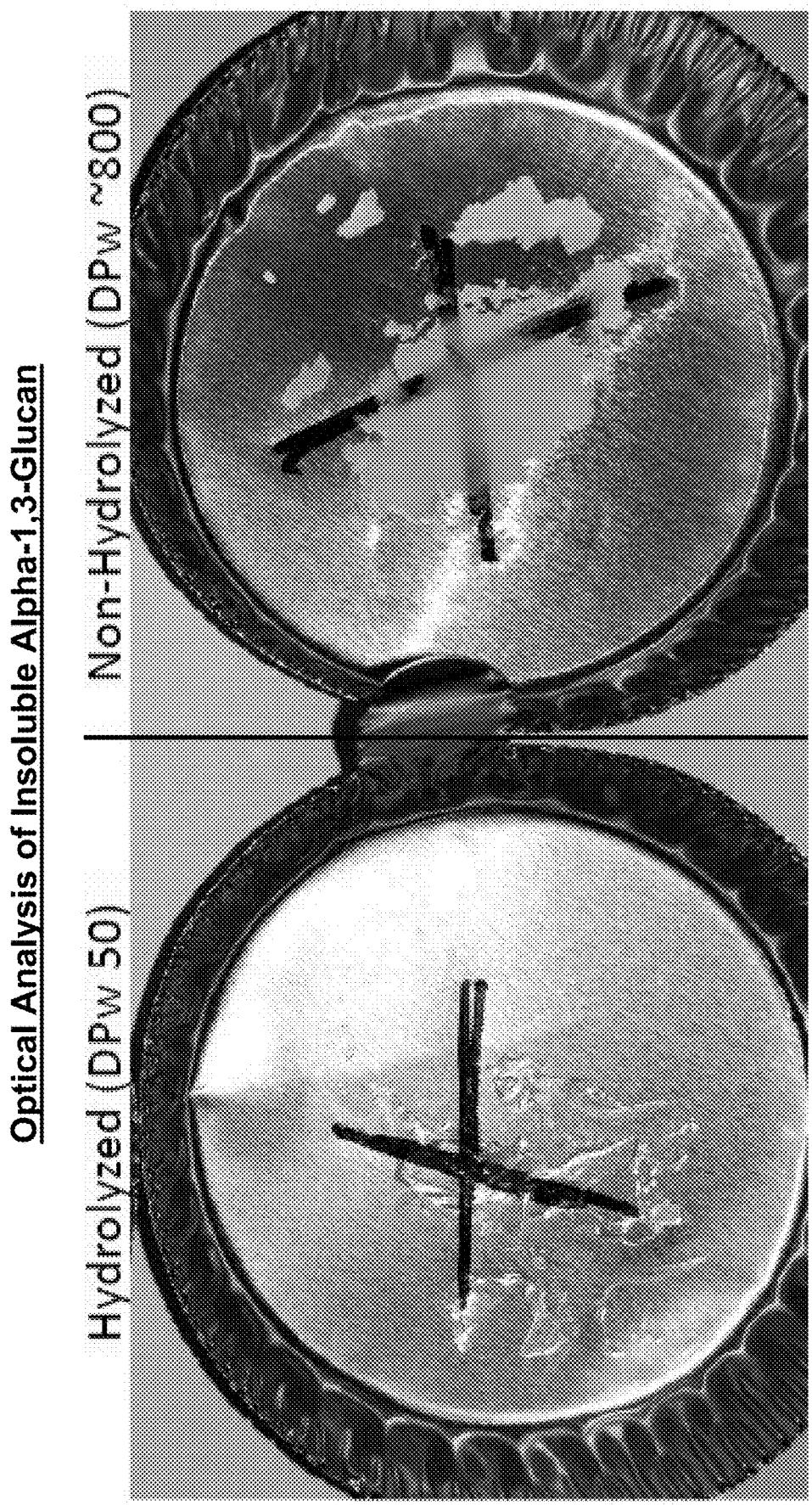
FIG. 7: Shown are individual layers of either DPw 50 (0.76 CI) alpha-1,3-glucan (as 28.3 wt % solids in dispersion) or DPw~800 alpha-1,3-glucan (as 33.7 wt % solids in dispersion) over "X" markings. The dried DPw 50 alpha-1,3-glucan was clear, whereas the dried DPw~800 alpha-1,3-glucan was hazy white. Refer to Example 4.

Wet cakes of DPw 50 or DPw~800 alpha-1,3-glucan (above) were prepared comprising about 28.3 wt % or 33.7 wt % of the glucan, respectively. Single layers of about 1-5 mm thick of either of these wet cakes in paste form were then spread onto aluminum pans and then photographed before drying. Notably, the DPw 50 alpha-1,3-glucan composition was optically transparent at a visual level, whereas the DPw~800 alpha-1,3-glucan composition lacked such clarity (FIG. 7). In particular, a black "X" mark could clearly be seen underneath the DPw 50 alpha-1,3-glucan material, which was not the case for the ~800 alpha-1,3-glucan material (FIG. 7), which was hazy.

Example 5

Aqueous Dispersions of Highly Crystalline Insoluble Alpha-Glucan are Stable

This Example describes the effects of drying (prior to glucan dispersal) on the viscosities of aqueous dispersions of highly crystalline insoluble alpha-glucan or non-crystalline alpha-glucan. In particular, dispersions of dried insoluble alpha-1,3-glucan (DPw 50, 0.76 CI) showed a viscosity profile similar to that of never-dried material, whereas dispersions of dried insoluble alpha-1,3-glucan (DPw~800) showed significantly reduced viscosity formation compared to its never-dried form. The viscosity-forming ability the DPw 50 alpha-1,3-glucan, even when in dry form, represents another advantage of this material.

Wet cakes of DPw 50 or DPw~800 alpha-1,3-glucan (above) were prepared comprising about 40 wt % glucan. Samples of each of these were then dried at 40-110° C. to powders of about 88-95 wt % solids. Samples of each of the wet cakes and dry powders were individually mixed with deionized water (room temperature, neutral pH) by hand-shaking (no automated device used) at 10 wt % solids. Each of these preparations was then processed at room temperature with a hand-held rotor stator (IKA T-25) at 10000 rpm (revolutions per minute) for 10 minutes. The resulting preparations, which manifested as dispersions for all but one of the preparations (see below), were then assessed for viscosity as described in Example 2.

Figure 8:
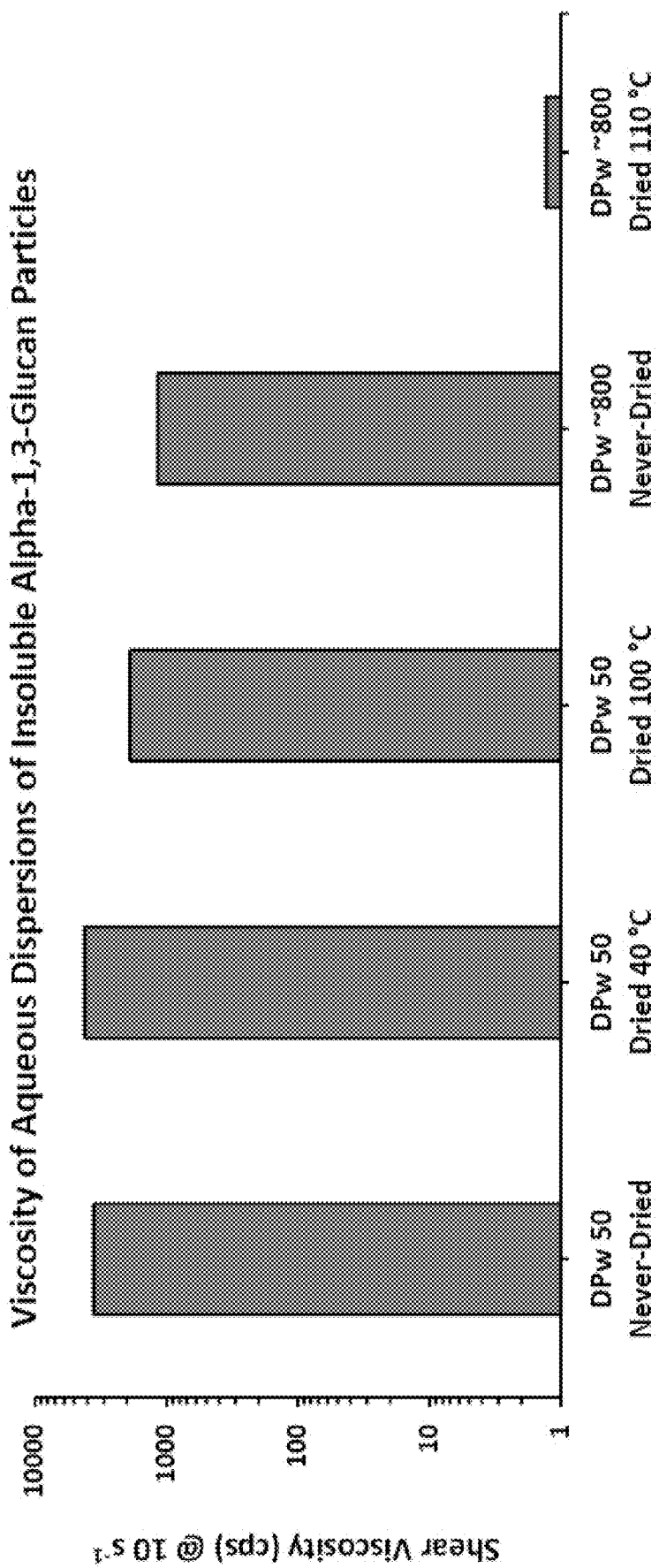
FIG. 8: Shown are the viscosities (at 10 s$^{-1}$) of 10 wt % aqueous preparations (neutral pH) of never-dried or dried alpha-1,3-glucan (DPw 50, 0.76 CI; or DPw~800). Refer to Example 5.

As shown in FIG. 8, the preparation of dried DPw~800 alpha-1,3-glucan in water had a viscosity level that was substantially less than the viscosity of the preparation of its never-dried form; its viscosity was less than 0.15% of the viscosity of the never-dried material. This result was consistent with the observation that the dispersion formed by the latter preparation was stable, whereas the former preparation hardly formed a dispersion at all (data not shown). Notably, the dispersions of dried DPw 50 alpha-1,3-glucan had viscosity levels that were comparable (within about 20-50%) to the viscosity of its never-dried form in dispersion (FIG. 8). Also, dispersions of either the dried or never-dried DPw 50 alpha-1,3-glucan were stable (data not shown).

Example 6

Emulsion Stabilization with Highly Crystalline Insoluble Alpha-Glucan

This Example shows that highly crystalline insoluble alpha-glucan can stabilize emulsions. In particular, insoluble alpha-1,3-glucan (DPw 50, 0.76 CI) demonstrated a stabilization effect on emulsions having a narrow droplet size distribution.

DPw 50 (0.76 CI) alpha-1,3-glucan was added to 0.5 or 2.0 wt % concentrations in 50:50 mixtures of dodecane and water. DPw~800 alpha-1,3-glucan (never-dried, 40 wt % wet cake) and alpha-1,3-glucan fibrids (prepared according to U.S. Pat. Appl. Publ. No. 2018/0119357, incorporated herein by reference) were similarly added to dodecane:water mixtures. Each preparation was then homogenized using a rotor stator homogenizer (Pro Scientific Pro 250) at 35000 rpm for 2 minutes. The resulting emulsions, which contained dodecane droplets dispersed in water, were analyzed for droplet size and stability. Droplet size was measured using a confocal laser scanning microscope where the dodecane phase was colored using a dye (perylene, 0.01 mg/mL) for contrast. Rheology of each emulsion was measured using a stress-controlled rotational rheometer (Anton Paar MCR-302) having a parallel plate geometry and a gap size of 1 mm.

Droplet size measurements were made directly on each emulsion to calculate average emulsion droplet size. Rheology measurement of the emulsions was used to calculate their average storage moduli (Avg. G') in the viscoelastic region. The results of these analyses are listed in Table 2 below. The effectiveness of emulsion stabilization (i.e., Avg. G', emulsion droplet size) was different for each of the alpha-1,3-glucan materials tested. The DPw 50 alpha-1,3-glucan sample was unique compared to the DPw~800 and fibrid alpha-1,3-glucan samples as it was able to stabilize the emulsion droplet size (small droplet size with low standard deviation—i.e., uniformly small droplets) and build elasticity (increased Avg. G' indicates increased elasticity). Thus, highly crystalline insoluble alpha-1,3-glucan of the present disclosure (e.g., DPw 50, 0.76 CI) can be used by itself as an emulsion stabilizer or can be combined with other stabilizers (e.g., alpha-1,3-glucan fibrids).

TABLE 2

Properties of Emulsions Stabilized by Insoluble Alpha-1,3-Glucan

| Insoluble Alpha-1,3-Glucan | | Emulsion | Emulsion Droplets | |
|---|---|---|---|---|
| Sample | wt % | Avg. G' (Pa) | Avg. Size (μm) | Std. Dev. (μm) |
| DPw 50 (0.76 CI) | 0.5 | 53 | 29.8 | 8 |
| DPw 50 (0.76 CI) | 2.0 | 102 | 29.1 | 7.1 |
| Fibrids | 0.5 | 70 | 141.3 | 74.6 |
| Fibrids | 2.0 | 200 | 171.6 | 93.5 |
| DPw ~800 [a] | 0.5 | 19 | 33.7 | 19.4 |
| DPw ~800 [a] | 2.0 | 148 | 49.3 | 41.8 |

[a] This glucan was never-dried and in the form of a 40 wt % wet cake prior to use in emulsion formation.

Example 7

Encapsulation with Highly Crystalline Insoluble Alpha-Glucan

This Example shows that highly crystalline insoluble alpha-glucan can be used to form dry emulsions. The constituent particles of these emulsions contain a core of stabilized material that is encapsulated by a shell of the insoluble alpha-glucan. In particular, insoluble alpha-1,3-glucan (DPw 50, 0.76 CI) was used to encapsulate an oil (shea nut butter), thereby forming particles with a hydrophobic core.

A mixture of DPw 50 (0.76 CI) alpha-1,3-glucan with water and shea nut butter was prepared at a ratio of 2 (glucan):20 (water):11 (shea nut butter). The mixture was heated to 60° C. under agitation to melt the shea nut butter. To form a liquid emulsion of the mixture, the mixture was homogenized using a rotor stator homogenizer (Ultra-Turrax T25, IKA) at 20 krpm for 5 minutes. Stability of the emulsion was confirmed visually.

The emulsion was freeze-dried or spray-dried to produce dry powder forms of the emulsion. To freeze-dry, the emulsion was rapidly cooled using dry ice and dried under vacuum at −50° C. for 48 hours.

To spray-dry, the emulsions were spray-dried using a spray-drier (Yamato Pulvis GB22) fitted with an external peristatic pump (Cole-Palmer Masterflex L/S) with #14 silicon tubing (Precision Pump). Atomization was done with a two-fluid nozzle and used air at 7 psi as the atomization gas. The drying air flow rate was 0.68 m$^3$/min, the dry inlet temperature was 120° C., and the outlet temperature was 50° C.

Figure 9:
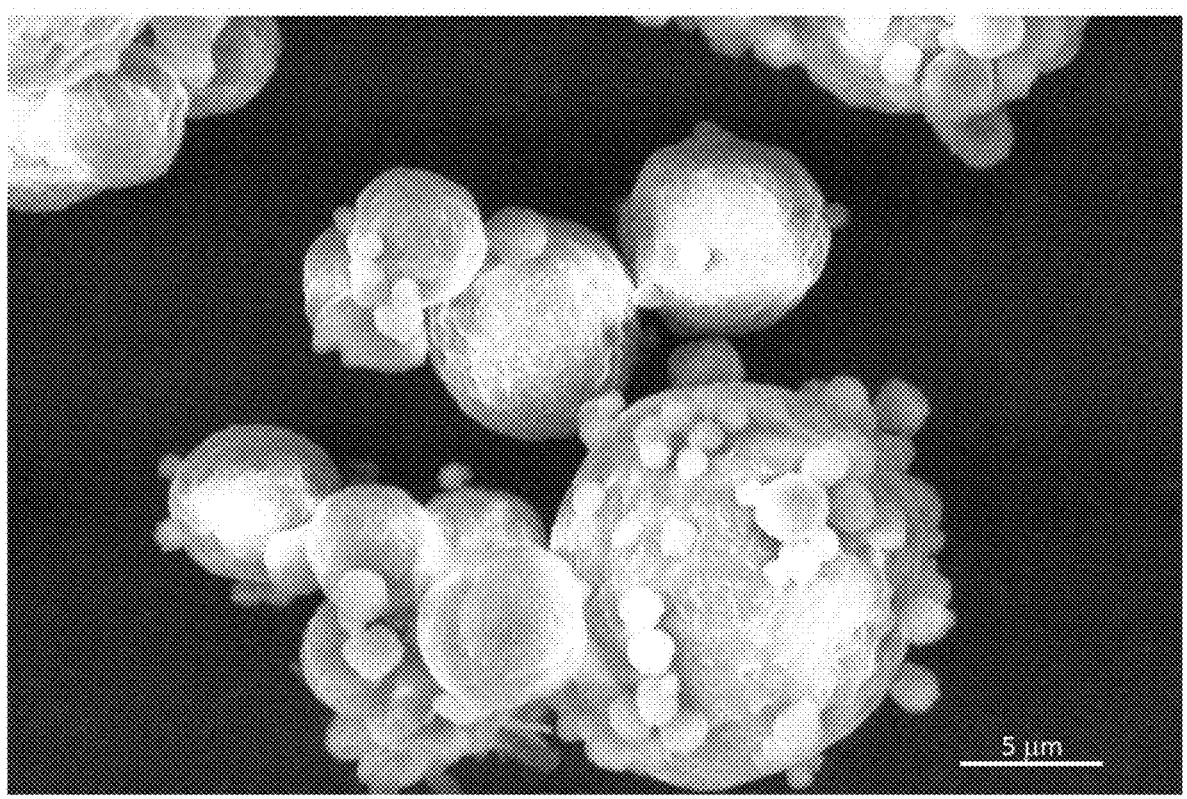
FIG. 9: Shown is an SEM image of a dry emulsion in which alpha-1,3-glucan encapsulates a hydrophobic core. White bar (inset), 5 μm. Refer to Example 7.

Each powder, produced by either freeze-drying or spray-drying, was imaged at 5000× by scanning electron microscopy (SEM). SEM was conducted with an FEI QUANTA 650 unit operating between 0.8 and 1 mbar and 10 kV of acceleration voltage. It was observed that each of the dried powder emulsions contained particles having a shea nut butter core and an alpha-1,3-glucan protective shell (e.g., see FIG. 9).

Example 8

Edible Coatings Comprising Highly Crystalline Insoluble Alpha-Glucan

This Example shows that highly crystalline insoluble alpha-glucan can be used in edible coatings on foods such as fruits and vegetables. Such edible coatings can be used, for example, to increase the shelf life of food. In particular, insoluble alpha-1,3-glucan (DPw 50, 0.76 CI) was used in edible coatings on avocados. Compared to uncoated samples, coating with the insoluble glucan inhibited fruit ripening, as determined by two different analyses.

Unripened avocados were dip-coated with a dispersion of 6-9 wt % insoluble alpha-1,3-glucan (DPw 50, 0.76 CI) (in water) and stored at 5 or 20° C. under 85% relative humidity (RH) for 1 week. The ripeness of the coated avocado samples was compared to the ripeness of uncoated avocado samples stored under the same conditions. Ripeness was classified using a five stage ready-to-eat (RTE) classification, as follows:

Stage 1: RTE insufficient, too hard (this stage generally characterizes the unripened avocado samples as entered to these analyses).
Stage 2: RTE sufficient, but some hardness.
Stage 3: RTE sufficient.
Stage 4: RTE sufficient, but some softness.
Stage 5: RTE insufficient, too soft.

The results of these analyses were as follows, indicating that coatings with insoluble alpha-1,3-glucan herein can prevent fruit ripening:

Uncoated sample, 5° C.: RTE Stage 1-2.
Uncoated sample, 20° C.: RTE Stage 3-4.
Coated sample, 20° C.: RTE Stage 1.

Also, the release of ethylene from the avocado samples (in duplicate) at 20° C. was tracked over time by gas chromatography. Ethylene production was tracked over four days (in parts-per-million [ppm]). Coated avocados showed a significantly lower amount of ethylene production, as shown in Table 3. This result is consistent with the above results that coatings with insoluble alpha-1,3-glucan herein can prevent fruit ripening.

TABLE 3

Ethylene Emission by Avocado Samples

| | Uncoated Avocado | | Avocado Coated with Insoluble Alpha-1,3-Glucan | |
|---|---|---|---|---|
| Day | Duplicate 1 | Duplicate 2 | Duplicate 1 | Duplicate 2 |
| 1 | 20.01 ppm | 14.74 ppm | 2.04 ppm | 5.50 ppm |
| 2 | 17.60 ppm | 19.36 ppm | 2.65 ppm | 6.98 ppm |
| 3 | 15.00 ppm | 18.02 ppm | 2.81 ppm | 7.21 ppm |
| 4 | 13.53 ppm | 16.04 ppm | 3.16 ppm | 6.87 ppm |

Example 8

Barrier Coatings Comprising Highly Crystalline Insoluble Alpha-Glucan

This Example shows that highly crystalline insoluble alpha-glucan can be used in barrier coatings for products. These barriers can provide protection against hydrophobic substances such as oil. In particular, aqueous preparations comprising insoluble alpha-1,3-glucan (DPw 50, 0.76 CI)

and other components were used to coat paper; these paper coatings resisted absorption of oil.

Insoluble alpha-1,3-glucan (DPw 50, 0.76 CI) was dispersed in aqueous solutions of 10 wt % water-soluble cationic alpha-1,3-glucan (WSCG), polyvinyl alcohol (PVOH, Mw 31 kDa, Sigma Aldrich), or starch (soluble potato starch, Sigma-Aldrich) at two different ratios: 8 parts or 5 parts of WSCG, PVOH, or starch to 2 parts or 5 parts of the insoluble alpha-1,3-glucan, respectively (these ratios were based on the wt %'s of each component in the final preparation). Each preparation was then coated onto a paper substrate using an automatic film applicator (ZAA2600 ZEHNTNER, RDS 3 rod). As controls, preparations with 10 wt % WSCG, PVOH, or starch, without any added insoluble alpha-1,3-glucan, were coated onto paper. The coated paper was dried and cut into 25-cm² sheets and analyzed using a Cobb tester (inside area 10 cm²). In particular, the coated paper was exposed to 10 mL of either water or castor oil for 60 seconds. At the 45-second mark, the contents were flipped out and the paper was carefully removed from the clamp. Each paper sample (weight thereof provided as "$m_{dry}$") was then blotted and rolled with a 10 kg roller at the 60-second mark to remove excess water or oil. The end weight of the paper ("$m_{exposed}$") was measured immediately. The following equation was used to calculate the Cobb value (g/m²) for each sample:

$$\text{Cobb value} = \frac{m_{exposed} - m_{dry}}{10 \times 10^4}$$

The Cobb value (Cobb index value) provides a measure of absorption by paper of an applied liquid, the higher the value, the higher the absorption. The following Cobb index value ranges were used to characterize the degree of water or oil absorption by paper in the above tests:

| Cobb Index Value | Barrier Property Classification |
|---|---|
| >20 | Not Good |
| 10-20 | Medium |
| 5-10 | Good |
| <5 | Excellent |

The Cobb index values measured for the above samples are listed in Table 4 below.

TABLE 4

Cobb Index Values of Coated Paper Exposed to Oil or Water

| | Cobb Index Value | |
|---|---|---|
| Coating Composition | Oil | Water |
| WSCG | 5 | 21.5 |
| WSCG/Insoluble Alpha-1,3-Glucan (8:2) | 5.4 | 20.5 |
| WSCG/Insoluble Alpha-1,3-Glucan (5:5) | 7.2 | 28.9 |
| PVOH | 15 | 25 |
| PVOH/Insoluble Alpha-1,3-Glucan (8:2) | 5.8 | 23.2 |
| PVOH/Insoluble Alpha-1,3-Glucan (5:5) | 16.7 | 28.1 |

TABLE 4-continued

Cobb Index Values of Coated Paper Exposed to Oil or Water

| | Cobb Index Value | |
|---|---|---|
| Coating Composition | Oil | Water |
| Starch | 6.6 | 43.6 |
| Starch/Insoluble Alpha-1,3-Glucan (8:2) | 4.8 | 37.6 |
| Starch/Insoluble Alpha-1,3-Glucan (5:5) | 7.2 | 29.4 |

Based on the data in Table 4, it is apparent that addition of insoluble alpha-1,3-glucan herein, especially at a ratio of 2 parts glucan to 8 parts of incumbent barrier material, can enhance the barrier properties of PVOH and starch against hydrophobic substances such as oil. The above results similarly characterize what is observed when cardboard or flex paper is used as the paper substrate for coating (data not shown).

Example 9

Reinforcement of Rubber Composites Using Highly Crystalline Insoluble Alpha-Glucan This Example shows that insoluble alpha-glucan herein can provide reinforcement to the physical and dynamic properties of rubber composites. In particular, rubber compositions comprising insoluble alpha-1,3-glucan (DPw 50, 0.76 CI) were produced and analyzed. Based on this analysis, it is contemplated that insoluble alpha-glucan of the present disclosure can be used to reinforce rubber-containing products such as tires.

To incorporate insoluble alpha-1,3-glucan (DPw 50, 0.76 CI) into rubber composites, a masterbatch of this insoluble alpha-glucan (30 wt % loading) in natural rubber (NR) was prepared. An aqueous dispersion of the insoluble alpha-glucan particles (7 wt %) and an NR latex (60 wt %) were mixed together into a slurry and coagulated with formic acid (5 vol %). The coagulum was divided into smaller parts, dried and milled. The dried coagulum (i.e., masterbatch) (<3% moisture) was used for rubber compounding.

The above-prepared masterbatch was mixed with rubber additives in an internal mixer in two passes according to the formulation in Table 5 below. In the first pass, the mixer was heated to 120° C. and the masterbatch with all the additives excluding sulfur and CBS were added. The temperature was increased to 150° C. during mixing and held for two minutes at 150° C. As comparative examples, NR masterbatches having silica or carbon black, in place of the insoluble alpha-glucan, were added in the first pass. In the second pass, the mixer was heated to 80° C. and the mixed rubber from the 1 st pass, sulfur and CBS were added. Each rubber preparation was mixed until the temperature reached 95 Once each rubber preparation cooled, it was milled in a two-roll mill, and then compression-molded and cured into test specimens for characterization.

TABLE 5

Formulation of Rubber Composites

| Component/Additive | | phr [a] |
|---|---|---|
| Polymer | SMR CV 60 [a] | 100 |
| Filler | 1. Insoluble alpha-1,3-glucan. | 40 |
| | 2. Silica - Ultrasil 7000 GR. | |
| | 3. Carbon black - N234. | |
| Aromatic Processing Oil (TDAE [a]) | HYPRENE L2000 | 5 |
| Curative | zinc oxide | 2.5 |
| Curative | stearic acid | 2 |
| Antidegradant | SANTOFLEX 6PPD | 2 |
| Antioxidant | WINGSTAY 100 | 0.5 |
| Processing Aid | STRUKTOL KK49 | 2 |
| Accelerator | CBS [a] | 1.70 |
| Curative | sulfur | 1.50 |
| Coupling Agents | Si69 [a] | 8 phf [a] (silica) |

[a] Abbreviations or meanings: phr, parts-per-hundred resin. SMR CV 60, a crosslinked natural rubber. Si69, bis(3-triethoxysilylpropyl)-tetrasulfide (only used for the silica-filled composite. TDAE, treated distillate aromatic extract. CBS, N-cyclohexyl-2-benzothiazolesulfenamide. phf, parts per 100 parts of filler.

The natural rubber composite containing insoluble alpha-1,3-glucan as a filler, and the comparative natural rubber composites that contained conventional fillers (carbon black or silica) were tested for physical and dynamic properties. A natural rubber composite that did not contain a filler was similarly tested. The results of these analyses are summarized in Table 6 below.

TABLE 6

Summary of Key Physical and Dynamic Properties of Rubber Composites

| | Filler | | | |
|---|---|---|---|---|
| Key Properties | None | Carbon Black | Silica | Insoluble Alpha-1,3-glucan |
| Shore A Hardness | 42 | 63 | 47 | 52 |
| Density (g/cm$^3$) | 1.00 | 1.08 | 1.10 | 1.06 |
| Tensile Strength (MPa) | 13.3 | 30.0 | 15.0 | 20.8 |
| Ultimate Elongation (%) | 573 | 580 | 633 | 550 |
| DIN Abrasion Loss (mm$^3$) | 1336 | 170 | 1430 | 281 |
| $t_{90}$ Cure Rate (min) | 11.18 | 5.86 | 18.80 | 8.44 |
| Modulus @ 100% Elongation (MPa) | 0.91 | 2.11 | 0.86 | 1.80 |
| Modulus @ 300% Elongation (MPa) | 2.22 | 10.98 | 3.11 | 6.83 |
| Minimum Elastic Torque ($M_L$), Min S' (dNm) | 0.39 | 1.43 | 0.09 | 0.02 |
| Maximum Elastic Torque ($M_H$), Max S' (dNm) | 6.97 | 16.26 | 6.58 | 10.11 |
| Tan delta @ 60° C. | 0.015 | 0.069 | 0.045 | 0.032 |

The following conclusions can be drawn from Table 6:

Insoluble alpha-1,3-glucan NR composites have a lower density compared to incumbent fillers. Thus, insoluble alpha-1,3-glucan as disclosed herein is suitable for light-weighting purposes, for example.

Insoluble alpha-1,3-glucan as a filler demonstrates overall improvement in physical properties (tensile strength, elongation, modulus) compared with high performance silica (Ultrasil GR 7000) filler, all without the need for a silane coupling agent (Si69).

Insoluble alpha-1,3-glucan NR composites have the lowest tan delta at 60° C. Thus, tires with insoluble alpha-1,3-glucan as disclosed herein will have good rolling resistance, as compared to using silica or carbon black instead.

Insoluble alpha-1,3-glucan mixes have a comparable cure time as that of N234 carbon black, and much lower $M_L$ for good processing.

Example 10

Enhancement of Polyurethane Films with Highly Crystalline Insoluble Alpha-Glucan This Example shows that insoluble alpha-glucan herein can enhance the mechanical and tensile properties polyurethane-based compositions. In particular, polyurethane films comprising insoluble alpha-1,3-glucan (DPw 50, 0.76 CI) were produced and analyzed.

Insoluble alpha-1,3-glucan (DPw 50, 0.76 CI) particles were blended with a propanediol (PDO)-sebacate polyol-based polyurethane dispersion (PUD) (Troy Polymers Inc) at different loading levels to make various one-component polyurethane dispersions (1 K-PUD). Formulation details of the PUD before are shown in Table 7 below.

TABLE 7

Formulation of Polyurethane Dispersion

| Component | Amount |
|---|---|
| PDO-Sebacate Polyol (2000 MW) | 100.00 g |
| Dimethylol Propionic Acid (DMPA) | 6.72 g |
| DABCO T-12 (dibutyltin dilaurate) | 0.09 g |
| Isophorone diisocyanate (IPDI) | 35.00 g |
| Triethylamine | 4.92 g |
| Water | 270.00 g |
| Ethylenediamine | 3.43 g |

Different amounts of insoluble alpha-1,3-glucan particles (provided as 10 wt % dispersion in water) were loaded to samples of the PUD to provide preparations with 1 to 50 wt % (relative to total solids) insoluble alpha-glucan. All of these PUD preparations were stable with no signs of phase separation. Each formulation was then blade-coated onto a polypropylene sheet using a drawdown wire rod #40, and allowed to form a film. The contents of these formulations (pre-coating), and the insoluble alpha-glucan content of the dried films, are listed in Table 8 below.

TABLE 8

Contents of PUD Preparations with Insoluble Alpha-1,3-Glucan, and of Films Prepared Therewith

| | | | | | |
|---|---|---|---|---|---|
| Insoluble alpha-1,3-glucan, 10 wt % solids in water (g)[a] | 0.6 | 6.9 | 26.8 | 41.6 | 62.4 |
| PDO-Sebacate PUD (Table 7), 31.2% solids in water (g)[a] | 20.0 | 20.0 | 20.0 | 20.0 | 20.0 |
| Total solids in water (wt %) | 30.6 | 25.8 | 19.1 | 16.9 | 15.1 |
| Insoluble alpha-1,3-glucan, after coating - dry film (wt %) | 1.0 | 10.0 | 30.0 | 40.0 | 50.0 |

[a]Gram amount of dispersion added.

The tensile properties of each film was then measured using an INSTRON instrument. The results of this analysis are shown in Table 9 below.

TABLE 9

Tensile Features of Films Formed from Polyurethane Dispersions Containing Insoluble Alpha-1,3-Glucan

| | Reference[a] | Insoluble Alpha-1,3-Glucan (wt % in film) | | | | |
|---|---|---|---|---|---|---|
| | | 1% | 10% | 30% | 40% | 50% |
| Tensile stress at break (psi) | 5146 ± 265 | 4569 ± 318 | 5283 ± 328 | 7862 ± 393 | 6940 ± 474 | 3534 ± 353 |
| Elongation at break (%) | 794 ± 59 | 751 ± 56 | 765 ± 16 | 566 ± 21 | 291 ± 33 | 44 ± 9 |
| Tensile stress at 50% elongation (psi) | 826 ± 99 | 739 ± 75 | 902 ± 30 | 2392 ± 72 | 4524 ± 220 | — |
| Tensile stress at 300% elongation (psi) | 1731 ± 160 | 1606 ± 163 | 2014 ± 110 | 4655 ± 477 | — | — |
| Area under the curve (ksi) | 20.7 ± 3.2 | 16.8 ± 1.6 | 20.5 ± 1.6 | 25.5 ± 2.3 | 15.5 ± 2.4 | 0.9 ± 0.2 |

[a]Control film with no insoluble alpha-1,3-glucan component.

The films were further analyzed after hydrolytic aging (50° C., 95% RH, 3 days) as shown in Table 10 below.

TABLE 10

Tensile Features of Hydrolytically Aged Films Formed from Polyurethane Dispersions Containing Insoluble Alpha-1,3-Glucan

| | Reference[a] | Insoluble Alpha-1,3-Glucan (wt % in film) | | | | |
|---|---|---|---|---|---|---|
| | | 1% | 10% | 30% | 40% | 50% |
| Tensile stress at break (psi) | 5702 ± 348 | 5334 ± 157 | 5839 ± 340 | 5928 ± 390 | 5363 ± 689 | 3532 ± 237 |
| Elongation at break (%) | 936 ± 72 | 991 ± 18 | 983 ± 51 | 797 ± 42 | 521 ± 20 | 286 ± 22 |
| Tensile stress at 50% elongation (psi) | 616 ± 14 | 531 ± 33 | 672 ± 44 | 1273 ± 96 | 2271 ± 244 | 2827 ± 143 |
| Tensile stress at 300% elongation (psi) | 1280 ± 17 | 1146 ± 57 | 1478 ± 66 | 2666 ± 180 | 3732 ± 396 | — |
| Area under the curve (ksi) | 23.3 ± 3.6 | 23.6 ± 0.9 | 27.0 ± 2.8 | 26.2 ± 3.3 | 18.4 ± 2.6 | 8.0 ± 1.3 |

[a]Control film with no insoluble alpha-1,3-glucan component.

Addition of insoluble alpha-1,3-glucan as presently disclosed into films prepared from polyurethane dispersions resulted in positive improvements in the mechanical properties of the films. These improvements occurred with or without hydrolytic aging of the films (Tables 9 and 10).

The films were also tested for hardness (ASTM D3363-20, Standard Test Method for Film Hardness by Pencil Test, ASTM International, 2020) and adhesion (ASTM D3359-17, Standard Test Methods for Rating Adhesion by Tape Test, ASTM International, 2017) (both ASTM tests are incorporated herein by reference). Films containing 10 wt % and 30 wt % insoluble alpha-1,3-glucan exhibited improved hardness from H to 2H (ASTM D3363), and improved adhesion from 4A to 5A (ASTM D3359).

Example 11

Melt-Processable Polyurethane Compositions Comprising Highly Crystalline Insoluble Alpha-Glucan This Example shows that a water-free masterbatch comprising insoluble alpha-glucan herein and polyurethane is melt-processable.

A dispersion of insoluble alpha-1,3-glucan particles (DPw 50, 0.76 CI) (8 wt % in water) was blended with a polyurethane dispersion (same formulation as listed in Table 7 of Example 10) at a ratio of 50/50 using an overhead mixer at 200 rpm for 5 minutes. The blended formulation (10 wt % solids) was dried in a vacuum oven at 80° C. for 48 hours to completely remove water. This drying rendered a hard, whitish, crumbly masterbatch preparation that could be molded with application of heat. For example, a clear film was prepared by heat-pressing the masterbatch dry powder at 105° C. and 20000 psi for 5 minutes. The high optical clarity (transparency) of the film indicated that the insoluble alpha-1,3-glucan component was well dispersed in the polyurethane matrix, and that the glucan has a unique particle size and morphology that does not create opaqueness.

Example 12

Gas Barrier Coatings Comprising Highly Crystalline Insoluble Alpha-Glucan

This Example shows that highly crystalline insoluble alpha-glucan can be used in barrier coatings to protect products from gaseous elements. In particular, barriers formed from aqueous preparations comprising insoluble alpha-1,3-glucan (DPw 50, 0.76 CI) particles had reduced oxygen transmission rates.

Films were casted comprising insoluble alpha-1,3-glucan (DPw 50, 0.76 CI) particles, butenediol vinyl alcohol copolymer (BVOH), and glycerol. To do so, a solution of BVOH and glycerol in water was prepared and divided into aliquots, after which the insoluble alpha-1,3-glucan particles were mixed into each aliquot at different concentrations. One aliquot did not receive any insoluble glucan (blank/control). Each of these preparations was then used to cast individual films, which were then dried. The blank/control film comprised about 90 wt % BVOH and about 10 wt % glycerol, while the other films contained increasing contents of the insoluble glucan (5, 10, or 20 wt %). Each film was then tested for its oxygen transmission rate (OTR) using 100% $O_2$ at 23° C. with 35% or 50% relative humidity (RH); the results of this analysis are shown in Table 11 below.

It is known that BVOH has relatively good OTR properties, and that this quality changes as a function of RH. At low RH, BVOH has good oxygen barrier properties (i.e., low OTR), but this benefit decreases at higher RH (i.e., OTR increases). The data in Table 11 indicate that including insoluble alpha-1,3-glucan as presently disclosed in films containing BVOH significantly enhances the oxygen barrier capacity of the films at both of the tested RH conditions. Thus, insoluble alpha-1,3-glucan particles herein can be used to enhance the oxygen barrier properties of compositions such as films, while also providing benefits of increased bio-content and biodegradability.

TABLE 11

Oxygen Transmission Rates (OTR) of Films Comprising BVOH and Insoluble Alpha-1,3-Glucan

| Insoluble Alpha-1,3-Glucan Content in Film | Thickness (µm) | OTR[a] (mL $O_2$/m² · day · bar) | |
|---|---|---|---|
| | | RH: 35% | RH: 50% |
| 0 wt % (blank) | 61.4 | 0.140 | 0.966 |
| 5 wt % | 84.0 | 0.003 | 0.738 |

TABLE 11-continued

Oxygen Transmission Rates (OTR) of Films Comprising
BVOH and Insoluble Alpha-1,3-Glucan

| Insoluble Alpha-1,3-Glucan Content in Film | Thickness (μm) | OTR[a] (mL O$_2$/m$^2$ · day · bar) | |
|---|---|---|---|
| | | RH: 35% | RH: 50% |
| 10 wt % | 79.8 | 0.008 | 0.693 |
| 20 wt % | 75.6 | 0.051 | 0.615 |

[a]OTR was normalized/corrected with respect to a film thickness of 100 μm.

Example 13

Using Highly Crystalline Insoluble Alpha-Glucan as a Binder in Non-Wovens

This Example shows that highly crystalline insoluble alpha-glucan can be used as a binder/strengthening agent in non-woven products, and that this effect can be enhanced when the glucan is crosslinked. In particular, the tensile strengths of non-wovens of two different types of pulp fiber were increased by treatment with insoluble alpha-1,3-glucan (DPw 50, 0.76 CI) particles that were crosslinked or non-crosslinked.

Air-laid non-woven sheets comprised of 100% fluff pulp (Georgia-Pacific) were sprayed with dispersions of insoluble alpha-1,3-glucan (DPw 50, 0.76 CI) particles that were either crosslinked or non-crosslinked, and then dried in a heated oven at 140° C. for 5 minutes. Alpha-1,3-glucan particle crosslinking was done using glyoxal, citric acid, or polyamideamine-epichlorohydrin (PAE). Upon drying the non-woven sheets, sheets receiving glucan particles comprised 80 wt % pulp and (i) 20 wt % glucan (non-crosslinked particles) or (ii) 16 wt % glucan and 4 wt % crosslinker. The dried nonwoven sheets were then analyzed for their dry and wet tensile strength properties using the EDANA standard NWSP 110.1.R0 (incorporated herein by reference). The above procedures/analyses were also conducted with wet-laid nonwoven sheets comprised of 100% northern bleached softwood kraft (NBSK) pulp (Domtar). These results of this work are listed in Table 12 below.

TABLE 12

Tensile Strengths of Non-Woven Products Comprising Insoluble
Alpha-1,3-Glucan Binder (Crosslinked or Non-Crosslinked)

| Non-Woven Composition (wt %) | Web Forming Process | Dry Tensile Strength (N/5 cm) | Wet Tensile Strength (N/5 cm) |
|---|---|---|---|
| 100% Fluff Pulp | Air-laid | <0.05 | <0.05 |
| 80% Fluff Pulp 20% Alpha-1,3-Glucan | Air-laid | 15.43 | <0.05 |
| 80% Fluff Pulp 16% Alpha-1,3-Glucan 4% Glyoxal | Air-laid | 26.32 | 3.73 |
| 80% Fluff Pulp 16% Alpha-1,3-Glucan 4% Citric Acid | Air-laid | 18.75 | 0.73 |
| 80% Fluff Pulp 16% Alpha-1,3-Glucan 4% PAE | Air-laid | 23.00 | 1.78 |
| 100% NBSK Pulp | Wet-laid | <0.05 | <0.05 |
| 80% NBSK Pulp 20% Alpha-1,3-Glucan | Wet-laid | 140.68 | 4.68 |
| 80% NBSK Pulp 16% Alpha-1,3-Glucan 4% Glyoxal | Wet-laid | 133.40 | 80.34 |

The data in Table 12 indicate that both non-crosslinked and crosslinked insoluble alpha-1,3-glucan particles of the present disclosure can strengthen non-woven materials.

Example 14

Light Scattering by Highly Crystalline Insoluble Alpha-Glucan

This Example discloses that insoluble alpha-glucan particles of the present disclosure have light scattering properties, and thus can be used as a light-scattering additive in compositions such as liquids. In particular, dispersions of insoluble alpha-1,3-glucan (DPw 50, 0.76 CI) particles in water were shown to scatter light.

Dispersions of insoluble alpha-1,3-glucan (DPw 50, 0.76 CI) particles in water at different concentrations (0.008, 0.08, 0.8, 8.0 wt %) were measured for scattering of 500 nm wavelength light. A CARY 100 UV-VIS spectroscope was used to measure the amount of light scattered in arbitrary units (a.u.). The data listed in Table 13 below indicate that the dispersed alpha-glucan particles can effectively scatter light. Even at 0.08 wt % loading levels, the dispersed particles exhibited a significant amount of light scattering. Further, it was found that the dispersed insoluble alpha-1,3-glucan does not absorb any light in the visible spectrum (i.e., the particles form a white dispersion).

TABLE 13

Light Scattering by Dispersions of Insoluble
Alpha-1,3-Glucan Particles in Water

| Alpha-1,3-Glucan Concentration | Light Scattering (a.u.) |
|---|---|
| 8 wt % | 2.778 |
| 0.8 wt % | 1.7573 |
| 0.08 wt % | 0.1762 |
| 0.008 wt % | 0.002 |

What is claimed is:

1. A method of producing insoluble alpha-glucan particles, said method comprising:
   (a) providing insoluble alpha-glucan as produced in an enzymatic reaction comprising at least water, sucrose and a glucosyltransferase enzyme that synthesizes the insoluble alpha-glucan, wherein the insoluble alpha-glucan has a weight-average degree of polymerization (DPw) of at least about 200 and at least 50% of the glycosidic linkages of the insoluble alpha-glucan are alpha-1,3 glycosidic linkages; and
   (b) hydrolyzing the insoluble alpha-glucan to insoluble alpha-glucan particles, wherein said hydrolyzing is performed under aqueous conditions at a pH of 2.0 or less;

wherein the insoluble alpha-glucan particles produced in step (b) have a degree of crystallinity of at least about 0.65 and a DPw of at least 15, and at least 50% of the glycosidic linkages of the insoluble alpha-glucan particles are alpha-1,3 glycosidic linkages.

2. The method of claim 1, further comprising a step of isolating the insoluble alpha-glucan particles produced in step (b).

3. The method of claim 1, wherein the alpha-glucan particles produced in step (b) have a DPw of about 35 to about 100.

4. The method of claim 1, wherein the alpha-glucan particles produced in step (b) have a DPw of about 35 to about 60.

5. The method of claim 1, wherein at least 80% of the glycosidic linkages of the alpha-glucan particles produced in step (b) are alpha-1,3 glycosidic linkages.

6. The method of claim 1, wherein at least 90% of the glycosidic linkages of the alpha-glucan particles produced in step (b) are alpha-1,3 glycosidic linkages.

7. The method of claim 1, wherein at least 99% of the glycosidic linkages of the alpha-glucan particles produced in step (b) are alpha-1,3 glycosidic linkages.

8. The method of claim 1, wherein the alpha-glucan particles produced in step (b) have a degree of crystallinity of at least about 0.75.

9. The method of claim 1, wherein the alpha-glucan particles produced in step (b) have a degree of crystallinity of at least about 0.70.

10. The method of claim 1, wherein at least 80 wt % of the alpha-glucan particles produced in step (b) are in the form of plates.

11. The method of claim 1, wherein step (b) is performed using acid hydrolysis.

12. The method of claim 11, wherein the acid hydrolysis is hydrochloric acid hydrolysis.

13. The method of claim 11, wherein the acid hydrolysis is nitric acid hydrolysis.

14. The method of claim 11, wherein the acid hydrolysis is sulfuric acid hydrolysis.

* * * * *